US 10,538,546 B2

United States Patent
Beaucage et al.

(10) Patent No.: US 10,538,546 B2
(45) Date of Patent: Jan. 21, 2020

(54) SOLID-PHASE PURIFICATION OF SYNTHETIC NUCLEIC ACID SEQUENCES

(71) Applicant: The United States of America, as represented by the Secretary, Department of Health and Human Services, Silver Spring, MD (US)

(72) Inventors: Serge L. Beaucage, Silver Spring, MD (US); Andrzej Grajkowski, Kensington, MD (US)

(73) Assignee: The United States of America, as represented by the Secretary, Department of Health and Human Services, Silver Spring, MD (US)

( * ) Notice: Subject to any disclaimer, the term of this patent is extended or adjusted under 35 U.S.C. 154(b) by 0 days.

(21) Appl. No.: 16/312,445

(22) PCT Filed: Jun. 28, 2017

(86) PCT No.: PCT/US2017/039720
§ 371 (c)(1),
(2) Date: Dec. 21, 2018

(87) PCT Pub. No.: WO2018/005630
PCT Pub. Date: Jan. 4, 2018

(65) Prior Publication Data
US 2019/0241596 A1    Aug. 8, 2019

Related U.S. Application Data

(60) Provisional application No. 62/356,214, filed on Jun. 29, 2016.

(51) Int. Cl.
| | |
|---|---|
| C07H 21/00 | (2006.01) |
| C07H 1/06 | (2006.01) |
| C07H 21/04 | (2006.01) |
| B01J 20/10 | (2006.01) |
| B01J 20/32 | (2006.01) |

(52) U.S. Cl.
CPC .............. *C07H 1/06* (2013.01); *B01J 20/103* (2013.01); *B01J 20/3204* (2013.01); *B01J 20/3246* (2013.01); *C07H 21/04* (2013.01)

(58) Field of Classification Search
None
See application file for complete search history.

(56) References Cited

PUBLICATIONS

Fang et al., "Scalable Synthetic Oligodeoxynucleotide Purification with Use of a Catching by Polymerization, Washing, and Releasing Approach," *Organic Letters* 12(16):3720-3723, Aug. 20, 2010.

Grajkowski et al., "Solid-Phase Purification of Synthetic DNA sequences," *The Journal of Organic Chemistry* 81(15):6164-6175, Aug. 5, 2016.
Grajkowski et al., "A High-Throughput Process for the Solid-Phase Purification of Synthetic DNA Sequences: Solid-Phase Purification of Synthetic DNA Sequences," *Current Protocols in Nucleic Acid Chemistry* 69(1):10.17.1-10.17.30, Jun. 19, 2017.
International Search Report dated Oct. 2, 2017 from International Application No. PCT/US2017/039720 (3 pages).
Pokharel et al., "Synthetic oligodeoxynucleotide purification by capping failure sequences with metharcylamide phosphoramidite followed by polymerization," *RSC Advances* 4(17)L8746-8757, Jan. 1, 2014.
Urdea et al., "Solid-Supported Synthesis, Deprotection and Enzymatic Purification of Oligodeoxyribonucleotides," *Tetrahedron Letters* 27(26):2933-2936, Jan. 1, 1986.
Written Opinion dated Oct. 2, 2017 from International Application No. PCT/US2017/039720 (9 pages).

*Primary Examiner* — Patrick T Lewis
(74) *Attorney, Agent, or Firm* — Klarquist Sparkman, LLP

(57) ABSTRACT

The invention provides a compound of the formula:

and a capture support of the formula:

wherein $R^1$, $R^2$, $R^3$, $R^6$, A, B, D, E, J, K, Q, W, and Z are as defined herein. The invention also provides a method of purifying an oligonucleotide or an oligonucleotide analog composed of "b" nucleotides from a mixture comprising the oligonucleotide or oligonucleotide analog and at least one oligonucleotide or oligonucleotide analog composed of "a" nucleotides, wherein b≠a, comprising use of the compound and the capture support.

30 Claims, 25 Drawing Sheets
Specification includes a Sequence Listing.

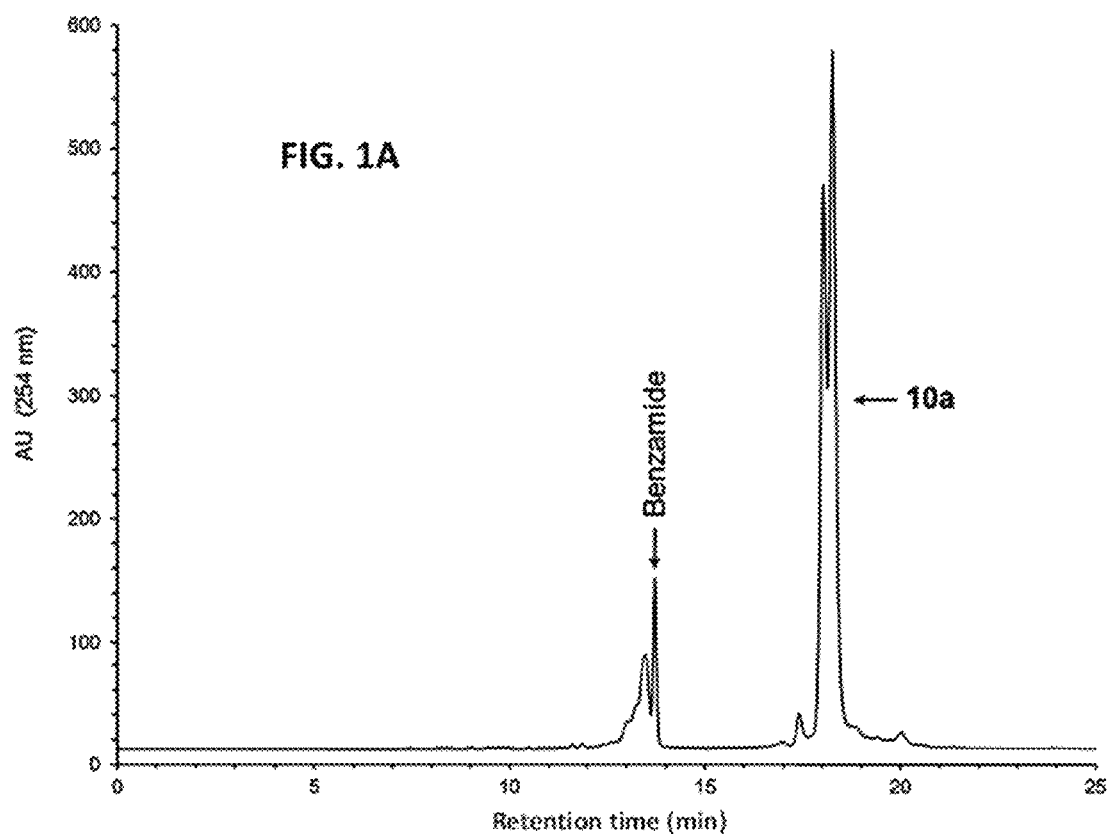
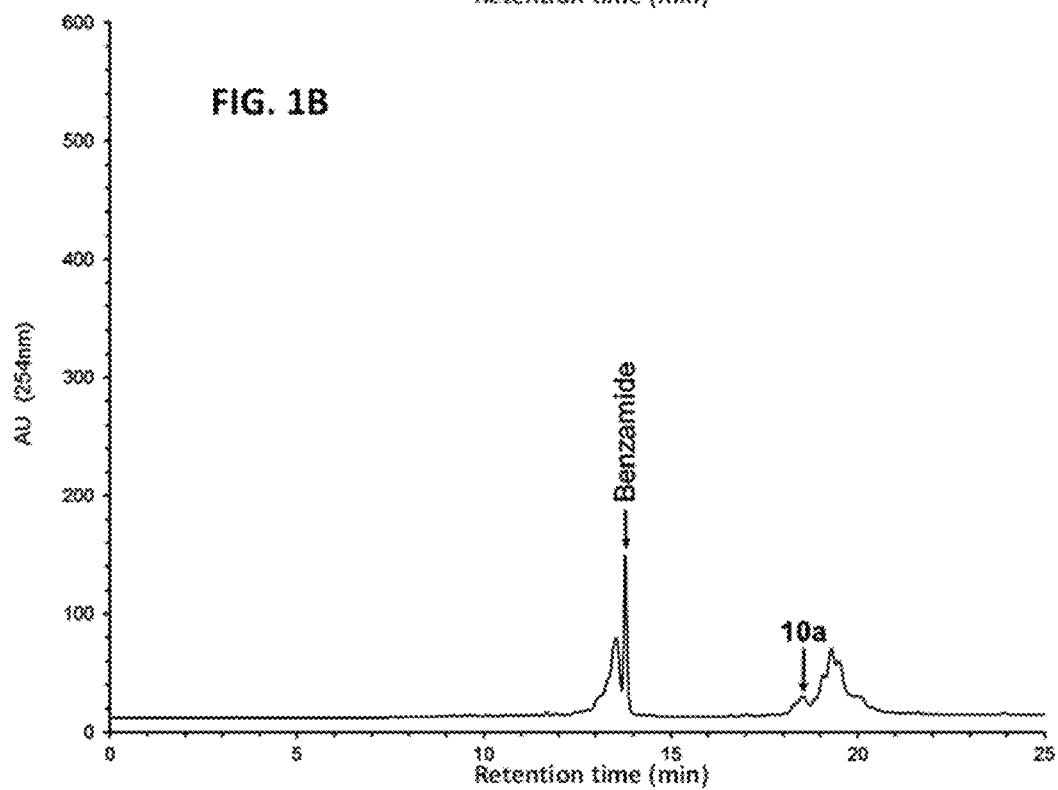

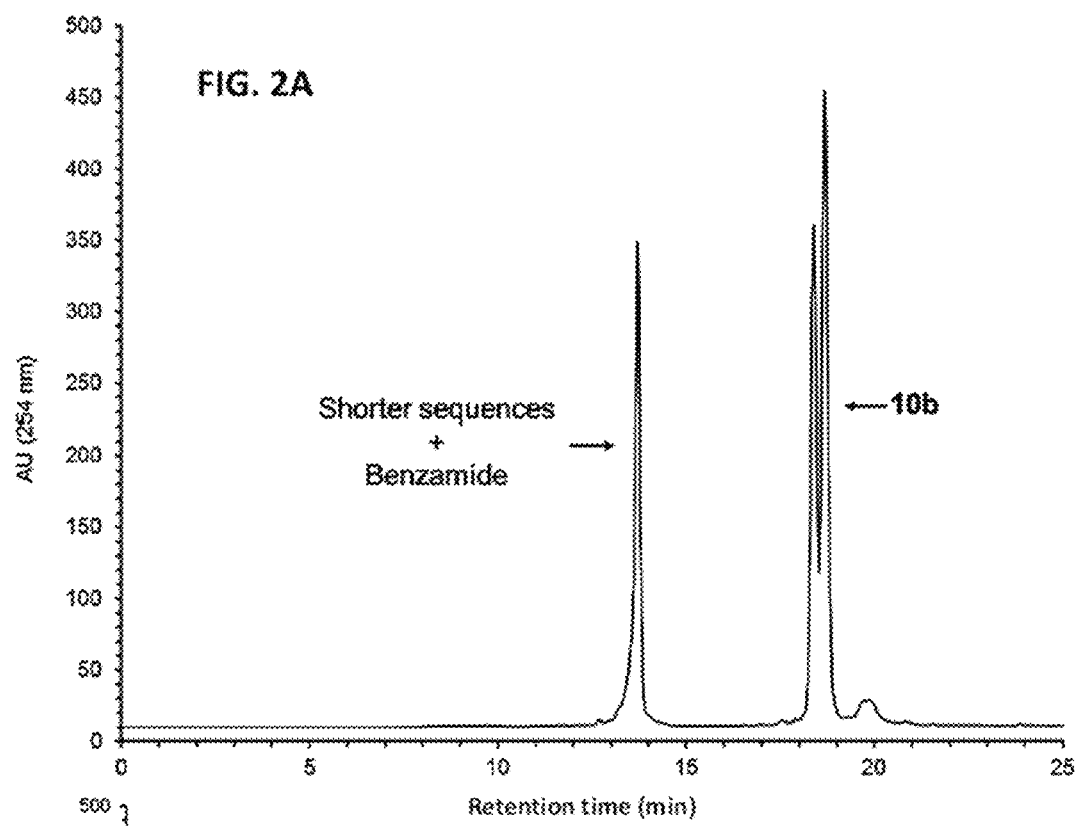
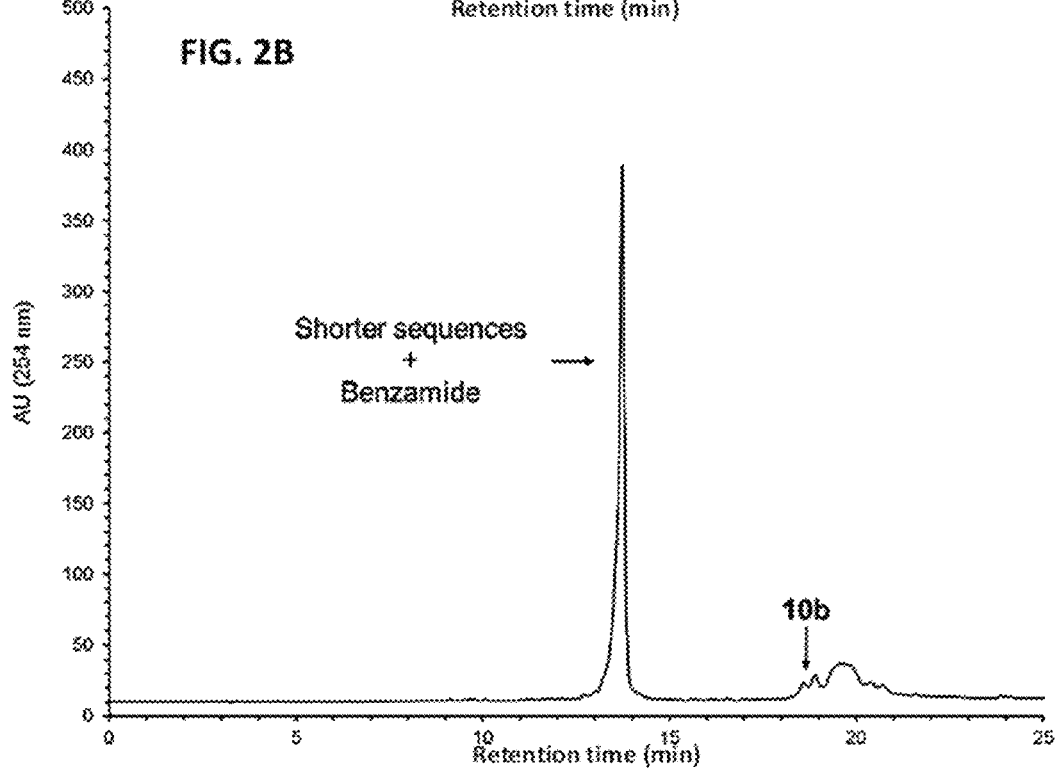

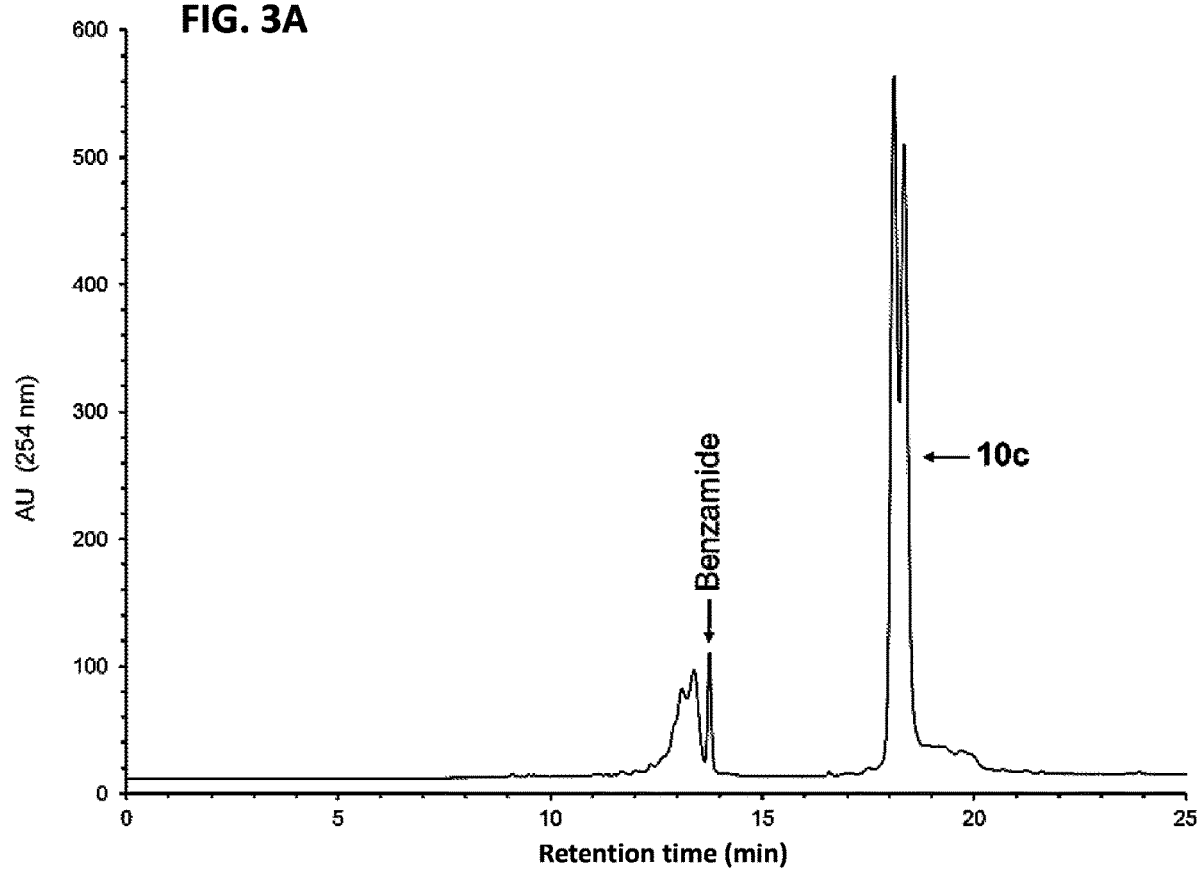
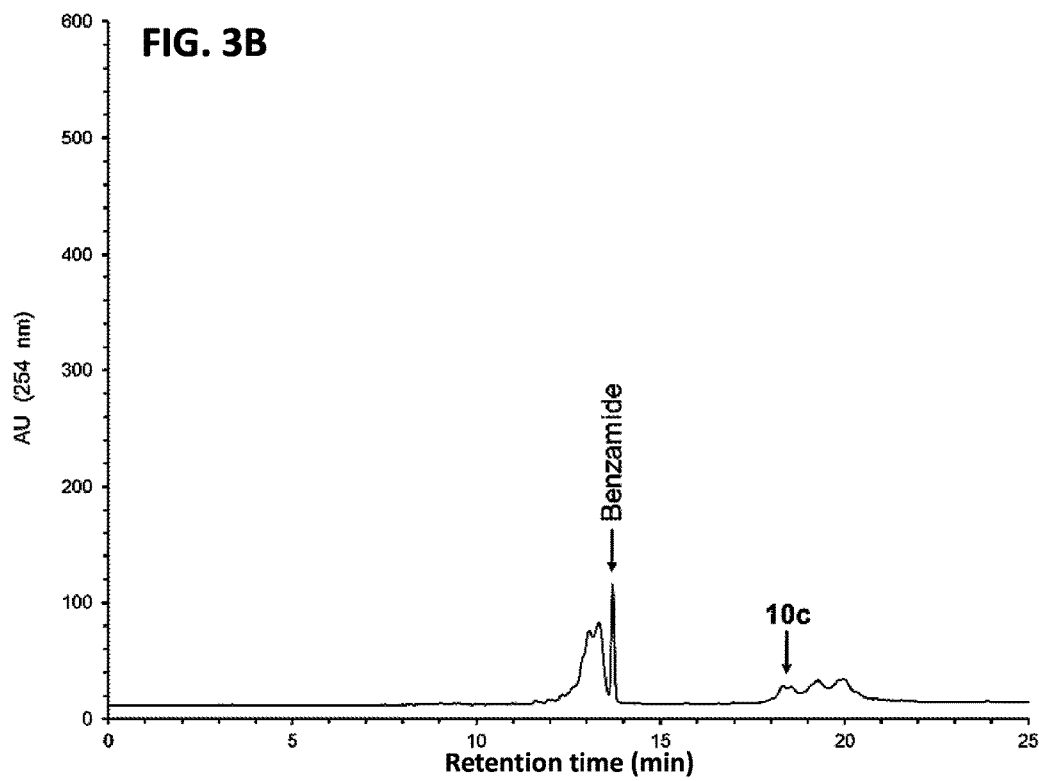

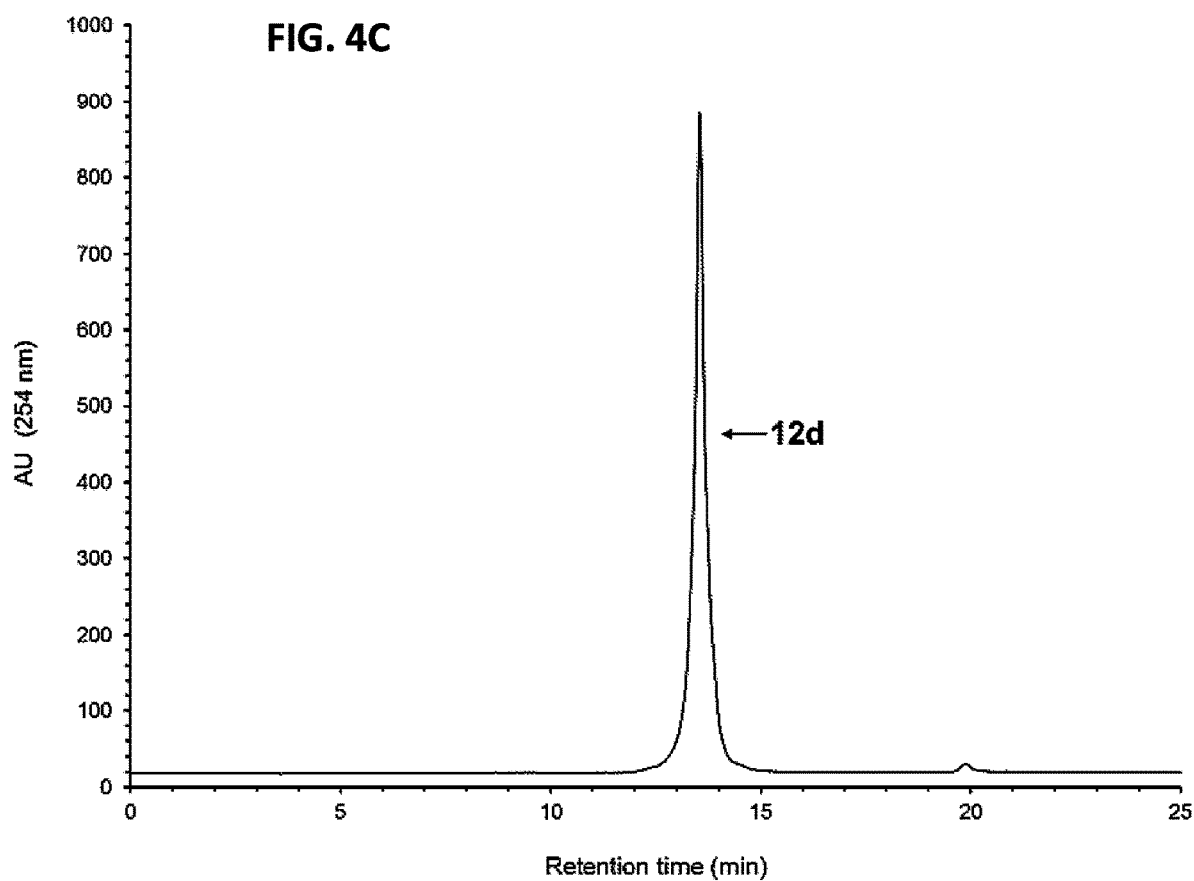

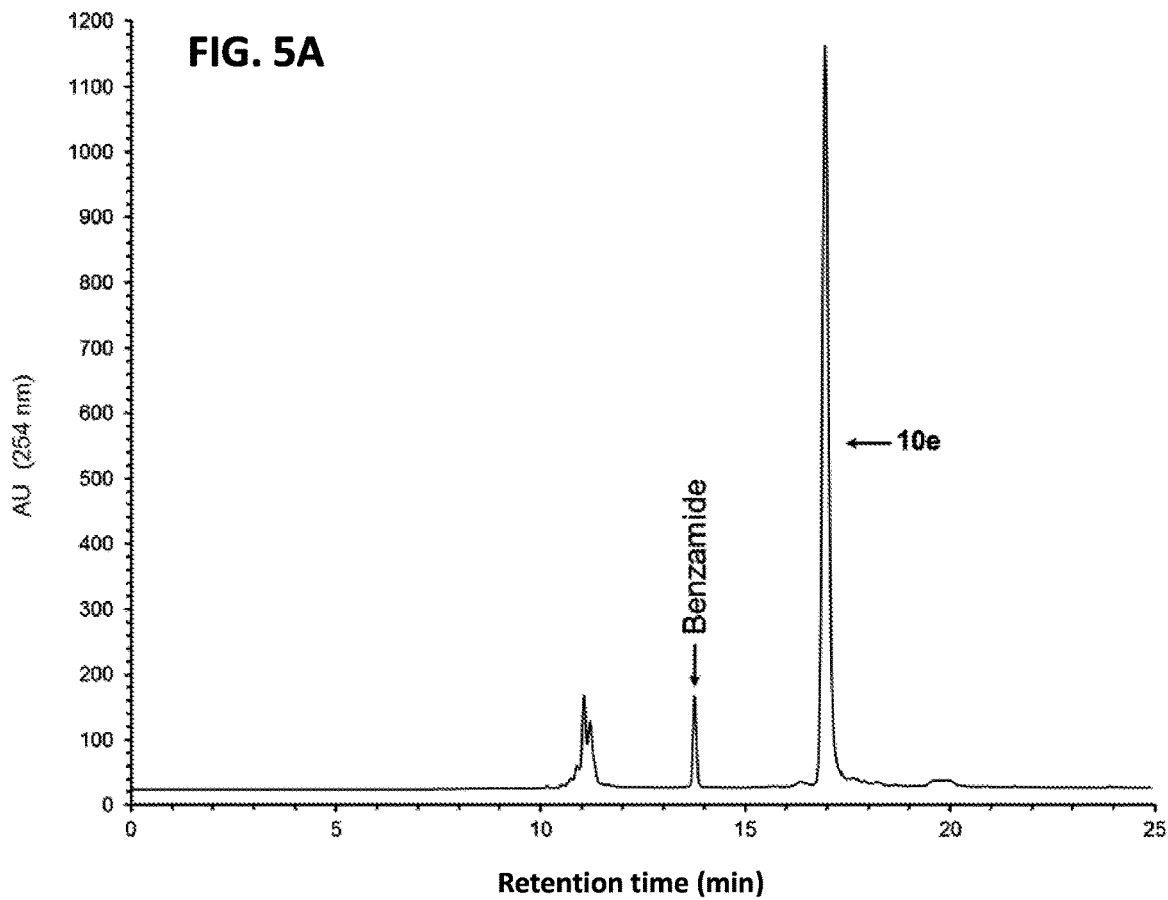
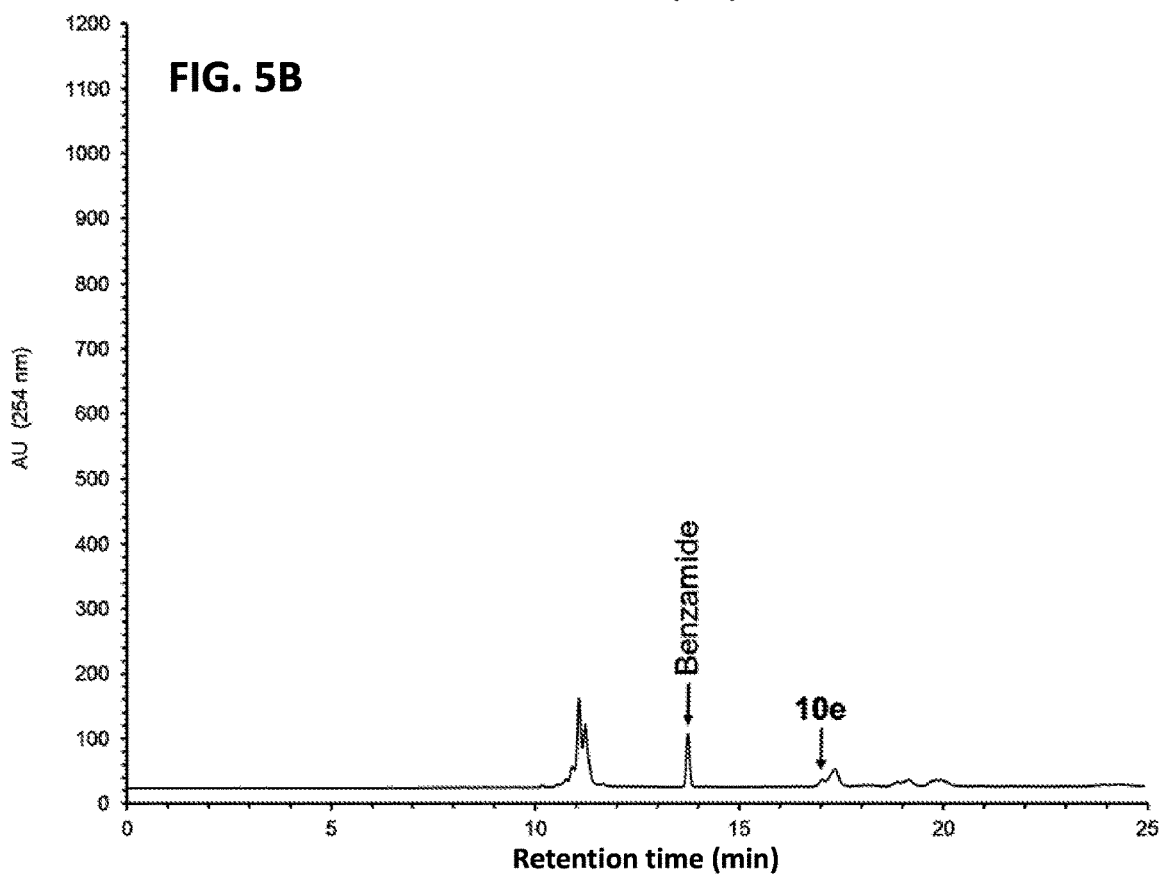

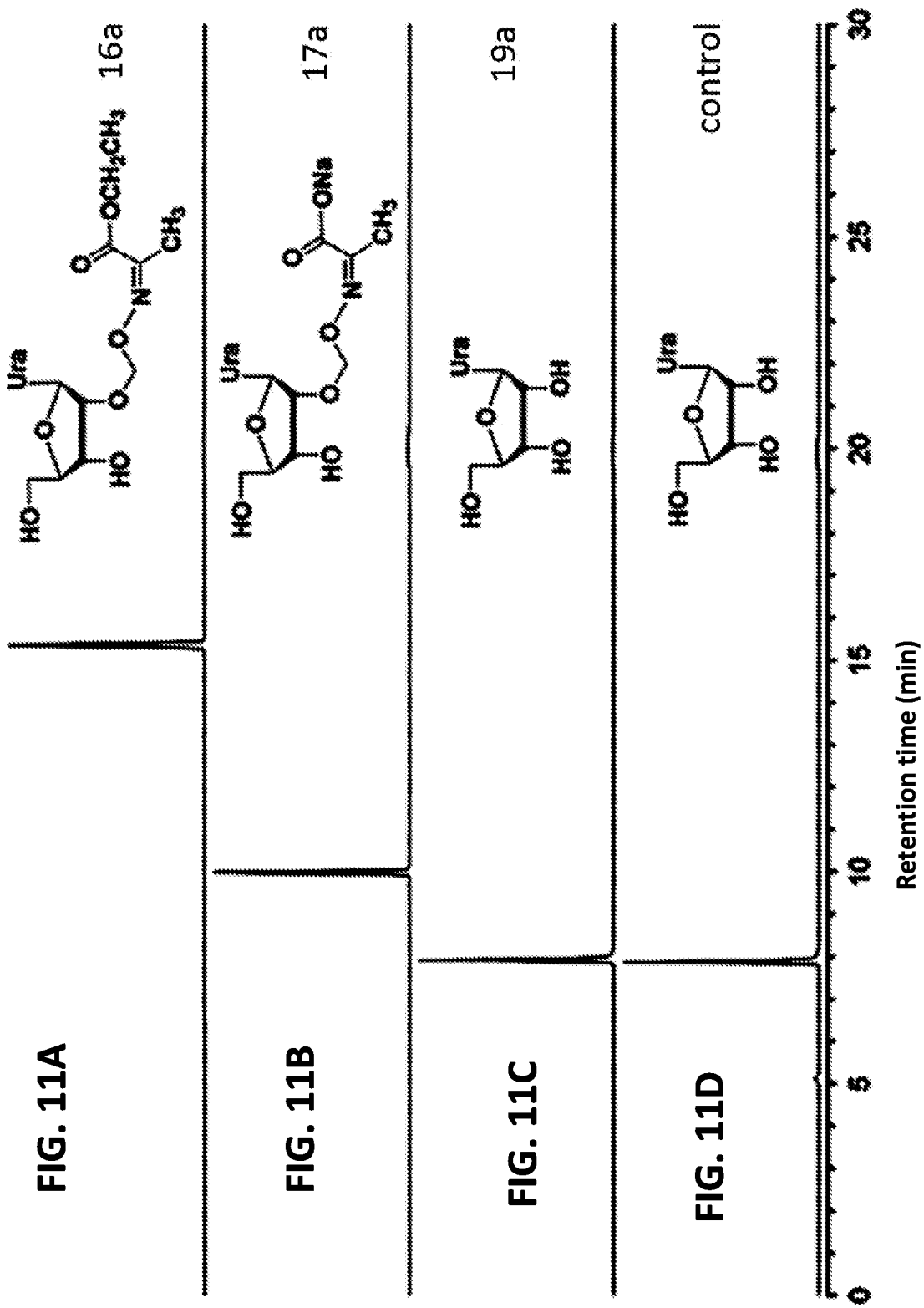

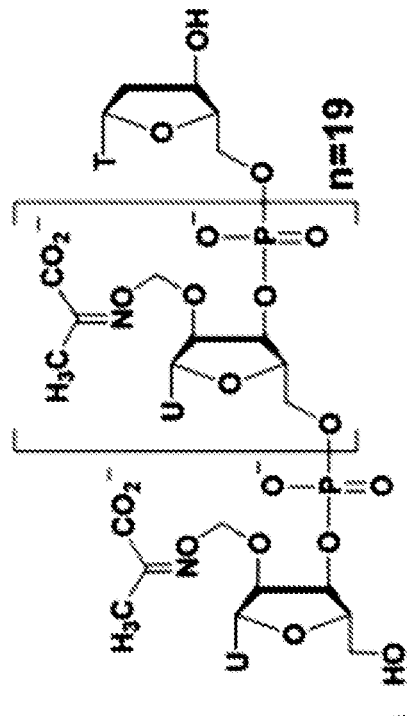
FIG. 15A
FIG. 15B
FIG. 15C

SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence

```
<220> FEATURE:
<223> OTHER INFORMATION: Synthetic
<220> FEATURE:
<221> NAME/KEY: misc_feature
<222> LOCATION: (1)..(20)
<223> OTHER INFORMATION: Nucleotide has phoshorothionate diester
      function
<220> FEATURE:
<221> NAME/KEY: misc_feature
<222> LOCATION: (1)..(1)
<223> OTHER INFORMATION: Nucleotide ketone linker function

<400> SEQUENCE: 1
acactgtgaa tcgatgccat                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: Nucleotide has phoshorothionate diester
      function
<220> FEATURE:
<221> NAME/KEY: misc_feature
<222> LOCATION: (1)..(1)
<223> OTHER INFORMATION: Nucleotide ketone linker function

<400> SEQUENCE: 2
ctccgtacct tacgtcttgt                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: Nucleotide has phoshorothionate diester
      function
<220> FEATURE:
<221> NAME/KEY: misc_feature
<222> LOCATION: (1)..(1)
<223> OTHER INFORMATION: Nucleotide ketone linker function

<400> SEQUENCE: 3
gtgagtagcg aacgtgaagt                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: Nucleotide has phoshorothionate diester
      function
<220> FEATURE:
<221> NAME/KEY: misc_feature
<222> LOCATION: (1)..(1)
<223> OTHER INFORMATION: Nucleotide ketone linker function

<400> SEQUENCE: 4
tatccgtagc taacgtcagt                                                   20
```

```
<210> SEQ ID NO 5
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Nucleotide ketone linker function

<400> SEQUENCE: 5
acactgtgaa tcgatgccat                                               20

<210> SEQ ID NO 6
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Nucleotide ketone linker function

<400> SEQUENCE: 6
tcactgtgaa tcgatgcaat tgcactgtga atcgatgcca tcactgtgaa tcgatgccat   60

<210> SEQ ID NO 7
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: Nucleotide has phoshorothionate diester
      function

<400> SEQUENCE: 7
acactgtgaa tcgatgccat                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: Nucleotide has phoshorothionate diester
      function

<400> SEQUENCE: 8
ctccgtacct tacgtcttgt                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: Nucleotide has phoshorothionate diester
      function
```

```
<400> SEQUENCE: 9
gtgagtagcg aacgtgaagt                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc
<222> LOCATION: (1)..(20)
<223> OTHER INFORMATION: Nucleotide has phoshorothionate diester
      function

<400> SEQUENCE: 10
tatccgtagc taacgtcagt                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
acactgtgaa tcgatgccat                                              20

<210> SEQ ID NO 12
<211> LENGTH: 60
<212> TYPE: DNA
<213> ORGANISM: Artificial Sequence
<220> FEATURE:
<223> OTHER INFORMATION: Synthetic

<400> SEQUENCE: 12
tcactgtgaa tcgatgcaat tgcactgtga atcgatgcca tcactgtgaa tcgatgccat   60

<210> SEQ ID NO 13
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(41)
<223> OTHER INFORMATION: polyuridylic acid

<400> SEQUENCE: 13
uuuuuuuuuu uuuuuuuuuu tuuuuuuuuu uuuuuuuuuu ut                     42
```

SOLID-PHASE PURIFICATION OF SYNTHETIC NUCLEIC ACID SEQUENCES

CROSS REFERENCE TO RELATED APPLICATIONS

This is the U.S. National Stage of International Application No. PCT/US2017/039720, filed on Jun. 28, 2017, which was published in English under PCT Article 21(2), which in turn claims the benefit of U.S. Provisional Application No. 62/356,214, filed on Jun. 29, 2016. Both applications are incorporated herein by reference in their entireties.

FIELD

The application concerns a high-throughput method of purifying synthetic nucleic acid sequences utilizing a solid-phase support.

BACKGROUND

The ability to design and synthesize DNA and RNA sequences has had a huge impact on biotechnology particularly in the rapidly growing fields of synthetic biology and nucleic acid-based drug development. Indeed, the use of synthetic DNA/RNA sequences and their analogues for recognition and binding to messenger RNAs encoding disease-causing proteins has led to the production of nucleic acid-based drugs capable of inhibiting the expression of these proteins through either an antisense or an RNA interference pathway in the potential treatment a wide spectrum of human diseases. Such applications require the production of synthetic nucleic acid sequences in large quantities (e.g., millimoles) and high purity for preclinical and clinical investigations. In contrast, total gene synthesis for synthetic biology applications requires small amounts (e.g., nanomoles) of numerous highly pure synthetic DNA sequences. Although the chemical synthesis of nucleic acid sequences using the phosphoramidite chemistry is efficient and can be scaled up for pharmaceutical production, the purification of these sequences presents a formidable challenge.

Despite the fact that the coupling efficiency of phosphoramidite monomers is near quantitative on controlled-pore glass (CPG) support, the full-length nucleic acid sequences are mixed with shorter sequences resulting from incomplete phosphoramidite coupling at each cycle of the nucleic acid sequence assembly. Other process-related impurities consist of deletion sequences due to failure to quantitatively prevent the growth of shorter than full-length sequences and to completely remove the 5'-hydroxyl protecting group at each step of the nucleic acid sequence assembly. Furthermore, the formation of longer than full-length nucleic acid sequences occurs when the activation of phosphoramidite monomers by a weak acid prompts the premature cleavage of the acid-labile 5'-hydroxyl protecting group of the newly extended nucleic acid sequence. Although these impurities are produced in small amounts, their physicochemical similarity to the desired nucleic acid sequence makes them very difficult to remove.

In the context of large-scale nucleic acid-based drug production, HPLC-based methods including reversed-phase (RP) HPLC and anion exchange HPLC are currently the preferred techniques for the purification of nucleic acid sequences. The methods require high-capacity instruments and accessories (e.g., preparative columns) in addition to large volumes of buffered aqueous and organic elution solvents. This process is neither cost-effective nor amenable to parallel purification processes; only a single nucleic acid sequence can be purified per run unless numerous instruments are available for this purpose. HPLC-based purification processes are time-consuming given that, depending on the nature of individual nucleic acid sequence, more than one purification run may be required to achieve the level of sequence purity required for pharmaceutical applications. One important limitation of any large-scale HPLC purification process is the burdensome removal of large volumes of aqueous solvents produced during purification, which may also depend on the physicochemical properties of each nucleic acid sequence; this operation requires costly equipment as well. In regard to the small-scale purification of DNA and RNA sequences for total gene construction in the realm of synthetic biology applications, HPLC-based methods can also be used for this purpose, but as discussed above, these methods are not amenable to cost-effective parallel purification of nucleic acid sequences. Furthermore, HPLC-based purification methods are time-consuming and often may not completely resolve shorter than full-length sequences from the desired nucleic acid sequences. Although polyacrylamide gel electrophoresis (PAGE) can efficiently separate shorter nucleic acid sequences from full length sequences, recovery of the purified sequences from the gel matrix is cumbersome and laborious with limited potential for parallel purification of nucleic acid sequences. A number of orthogonal methods have, however, been proposed for the purification of nucleic acid sequences. These methods are based on affinity, hydrophobic or ion-pair chromatography and solid-phase removal of shorter than full-length nucleic acid sequences by enzymatic hydrolysis or by hydrophobic retention of the full-length sequences.

All of those techniques are either not amenable to highly parallel or large scale purification of nucleic acid sequences or both. Thus, there remains a need in the art for improved methods for the purification of synthetic DNA and RNA sequences.

SUMMARY

The invention provides a method of purifying an oligonucleotide or an oligonucleotide analog composed of "b" nucleotides from a mixture comprising the oligonucleotide or oligonucleotide analog and at least one oligonucleotide or oligonucleotide analog composed of "a" nucleotides, wherein b≠a, which method comprises:

(i) providing a protected nucleoside or nucleoside analog of formula (I) or (Ia) functionalized with an activatable phosphorus-containing entity:

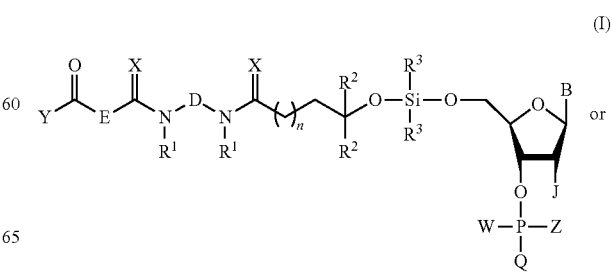

(Ia)

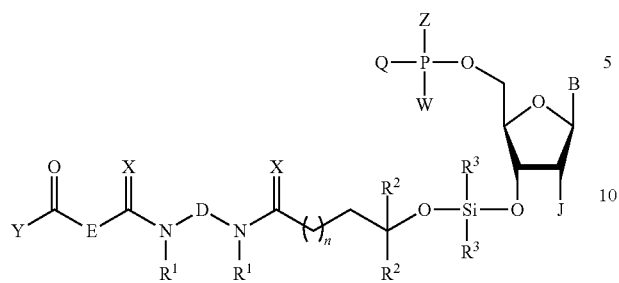

wherein B is an optionally protected nucleobase or an optionally protected nucleobase analog, D and E are independently $C_2$-$C_{10}$ alkanediyl, n is 1 to 4, $R^1$ is $C_1$-$C_6$ linear or branched alkyl or $C_3$-$C_8$ cycloalkyl, $R^2$ is hydrogen or linear or branched $C_1$-$C_6$ alkyl, $R^3$ is linear or branched $C_3$-$C_6$ alkyl, J is H or $OR^7$ wherein $R^7$ is a reversible or permanent hydroxyl protecting group, X is O or S, Y is H or $C_1$-$C_6$ linear alkyl, W is a lone pair of electrons or an oxo function, when W is a lone pair of electrons, Z is $NR^4R^5$ wherein $R^4$ and $R^5$ are individually $C_1$-$C_6$ alkyl, $C_{6-10}$ arylated $C_{1-6}$ alkyl, or $C_3$-$C_8$ cycloalkyl or $R^4$ and $R^5$ taken together with the nitrogen atom to which they are attached form a saturated 3-10 membered heterocyclic ring optionally including one or more additional heteroatoms selected from the group consisting of nitrogen, oxygen and sulfur, and Q is OT wherein T is a reversible or permanent hydroxyl protecting group, and when W is an oxo function, Z is H and Q is $O^-$, (ii) providing a mixture comprising an optionally protected first oligonucleotide or oligonucleotide analog V' composed of b-1 nucleotides or nucleotide analogs and having a free 5'-terminal OH group, wherein the first oligonucleotide V' comprises phosphate or phosphorothioate triester linkages, or a combination thereof, and wherein the first oligonucleotide V' is linked at its 3'-terminus to a solid support, wherein at least one oligonucleotide or oligonucleotide analog composed of "a" nucleotides is also linked to the solid support, (iii) coupling the first oligonucleotide V' with the protected nucleoside or nucleoside analog of formula (I) or (Ia), to provide a second oligonucleotide of the formula (II) or (IIa):

(II)

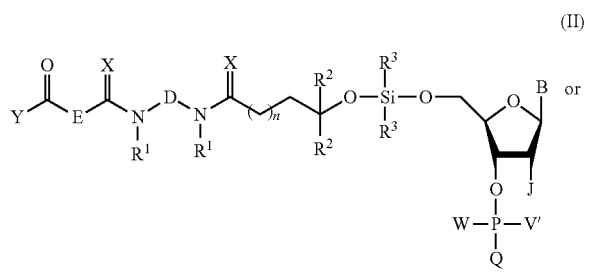

(IIa)

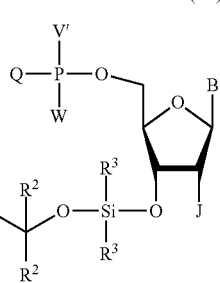

(iv) oxidizing or sulfurizing, optionally deprotecting, and cleaving the second oligonucleotide or oligonucleotide analog of the formula (II) or (IIa) from the solid support to form a mixture comprising a third oligonucleotide of the formula (III) or (IIIa):

(III)

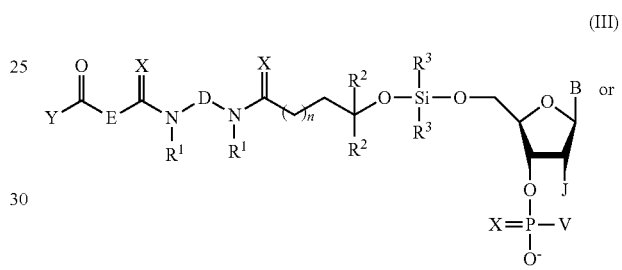

(IIIa)

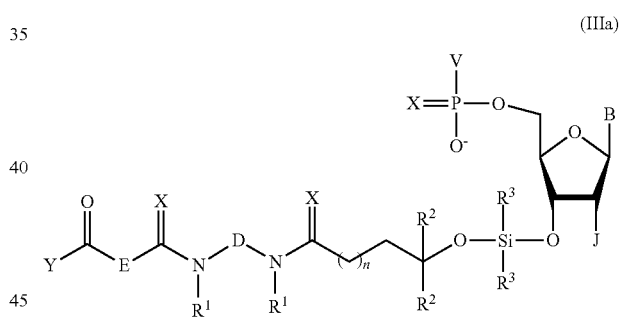

wherein V is the moiety resulting after optional deprotection of the second oligonucleotide or oligonucleotide analog and wherein V is not linked to the solid support, (v) reacting the mixture comprising the third oligonucleotide or oligonucleotide analog of the formula (III) or (IIIa) with a silica-attached linker compound of the formula:

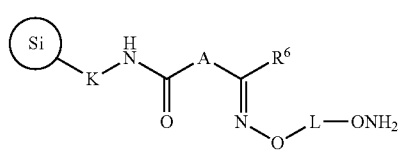

wherein A, K, and L are independently $C_2$-$C_{10}$ alkanediyl and $R^6$ is H, $C_1$-$C_6$ linear or branched alkyl, or $C_3$-$C_8$ cycloalkyl, and wherein

 is silica, to form a linker-attached oligonucleotide or oligonucleotide analog of the formula (IV) or (IVa):

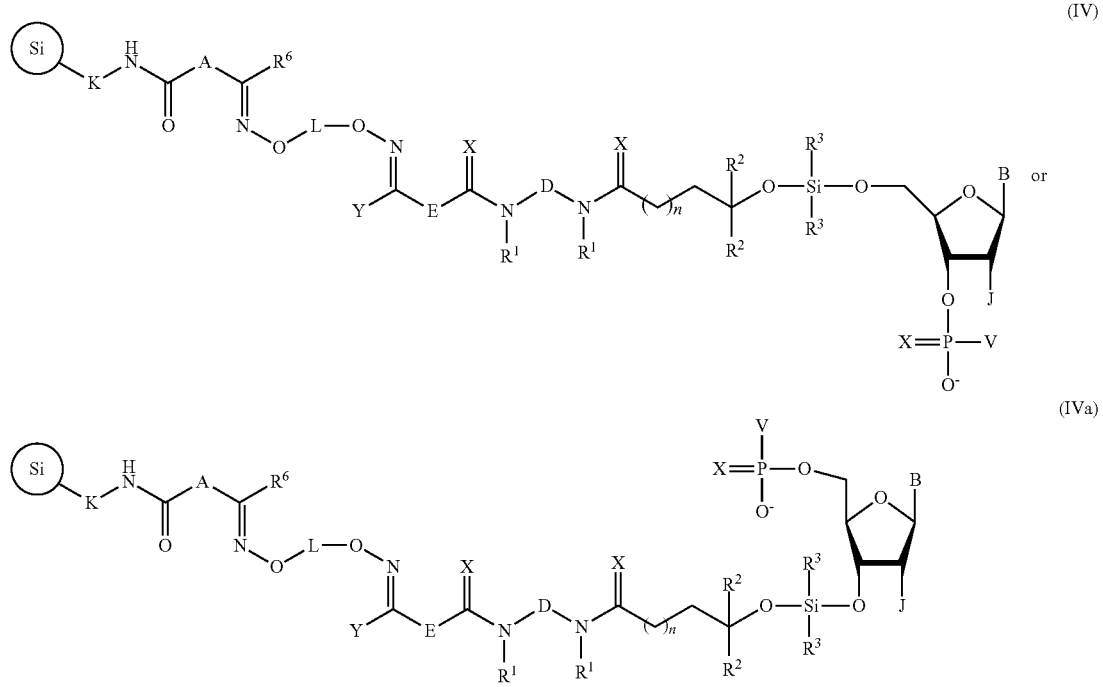

(vi) washing the linker-attached oligonucleotide of the formula (IV) or (IVa) with at least one solvent or mixture of solvents to remove the oligonucleotide(s) or oligonucleotide analog(s) composed of "a" nucleotides, (vii) treating the linker-attached oligonucleotide or oligonucleotide analog of formula (IV) or (IVa) with a desilylation agent, and (viii) isolating the purified oligonucleotide or oligonucleotide analog composed of "b" nucleotides from the product of step (vii).

The invention also provides a compound of the formula:

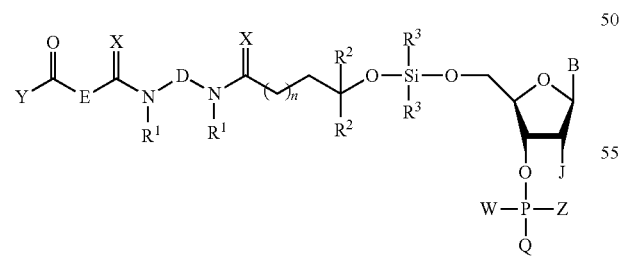

wherein B is an optionally protected nucleobase or optionally protected nucleobase analog, D and E are independently $C_2$-$C_{10}$ alkanediyl, n is 1 to 4, $R^2$ is hydrogen or $C_1$-$C_6$ linear or branched alkyl or $C_3$-$C_8$ cycloalkyl, $R^3$ is linear or branched $C_3$-$C_6$ alkyl, J is H or $OR^7$ wherein $R^7$ is a reversible or permanent hydroxyl protecting group, X is O or S, Y is H or linear $C_1$-$C_6$ alkyl, W is a lone pair of electrons, and Z is $NR^4R^5$ wherein $R^4$ and $R^5$ are individually $C_1$-$C_6$ alkyl, $C_6$-$C_{10}$ arylated $C_1$-$C_6$ alkyl, or $C_3$-$C_8$ cycloalkyl containing 1 to 10 carbon atoms or $R^4$ and $R^5$ taken together with the nitrogen atom to which they are attached form a saturated 3-10 membered heterocyclic ring optionally including one or more additional heteroatoms selected from the group consisting of nitrogen, oxygen and sulfur, and Q is OT wherein T is a reversible or permanent hydroxyl protecting group.

The invention further provides a capture support of the formula (9):

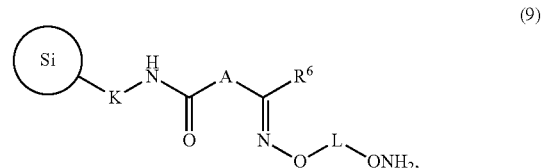

wherein A, K, and L are independently $C_2$-$C_{10}$ alkanediyl and $R^6$ is H, $C_1$-$C_6$ linear or branched alkyl, or $C_1$-$C_6$ cycloalkyl, and wherein

is silica.

The foregoing and other objects, features, and advantages of the invention will become more apparent from the following detailed description, which proceeds with reference to the accompanying figures.

BRIEF DESCRIPTION OF THE DRAWINGS

FIG. 1A shows the RP-HPLC profile of unpurified 10a (5'-functionalized 12a).

FIG. 1B shows the RP-HPLC profile of the phosphorothioate DNA sequence 10a after capture by the support 3.

FIG. 1C shows the RP-HPLC analysis of solid-phase purified 12a that has been released from the support 11a.

FIG. 2A shows the RP-HPLC profile of unpurified 10b (5'-functionalized 12b).

FIG. 2B shows the RP-HPLC profile of remaining unpurified 10b after capture by support 3.

FIG. 3A shows the RP-HPLC profile of unpurified 10c (5'-functionalized 12c).

FIG. 3B shows the RP-HPLC profile of remaining unpurified 10c after capture by support 3.

FIG. 4C shows the RP-HPLC analysis of solid-phase purified 12d that has been released from the capture support 11d.

FIG. 4D shows the purity analysis of the solid-phase purified 12d by PAGE. Left lane: Solid-phase capture of 10d spiked with RP-HPLC purified 14-, 16- and 18-mer phosphorothioate DNA sequences. Middle lane: Solid-phase purified 12d. Right lane: Unpurified DNA sequence 10d spiked with RP-HPLC purified 14-, 16- and 18-mer phosphorothioate DNA sequences.

FIG. 5A shows the RP-HPLC profile of unpurified 10e (5'-functionalized 12e).

FIG. 5B shows the RP-HPLC profile of unpurified 10e after capture by the support 3.

FIG. 6C shows the RP-HPLC analysis of solid-phase purified 12f that has been released from the support 11a.

FIGS. 11A-11D shows RP-HPLC profiles that demonstrate the sequential deprotection of uracil-1-yl ribonucleoside 16a that is protected with a 2'-O-iminooxymethyl propanoate protecting group.

FIG. 11A provides the RP-HPLC profile for the silica-gel-purified 2'-O-protected uridine 16a.

FIG. 11B provides the RP-HPLC profile for the de-esterified 2'-O-protected uridine 17a.

FIG. 11C provides the RP-HPLC profile for the 2'-O-deprotected uridine 19a.

FIG. 11D provides the RP-HPLC profile for a commercial sample of uridine as a control.

FIG. 12A provides the RP-HPLC profile for the silica-gel-purified 2'-O-protected cytosine 16b.

FIG. 12B provides the RP-HPLC profile for the de-esterified 2'-O-protected cytosine 17b.

FIG. 12C provides the RP-HPLC profile for the 2'-O-deprotected cytosine 19b.

FIG. 12D provides the RP-HPLC profile for a commercial sample of cytosine as a control.

FIG. 13A provides the RP-HPLC profile for the silica-gel-purified 2'-O-protected adenine 16c.

FIG. 13B provides the RP-HPLC profile for the de-esterified 2'-O-protected adenine 17c.

FIG. 13C provides the RP-HPLC profile for the 2'-O-deprotected adenine 19c.

FIG. 13D provides the RP-HPLC profile for a commercial sample of adenine as a control.

FIG. 14A provides the RP-HPLC profile for the silica-gel-purified 2'-O-protected guanine 16d.

FIG. 14B provides the RP-HPLC profile for the de-esterified 2'-O-protected guanine 17d.

FIG. 14C provides the RP-HPLC profile for the 2'-O-deprotected guanine 19d.

FIG. 14D provides the RP-HPLC profile for a commercial sample of guanine as a control.

FIGS. 15A-15C provide RP-HPLC analysis of unpurified and desalted chimeric RNA sequences. U: uracil-1-yl; T: thymin-1-yl.

FIG. 15A shows an RP-HPLC profile of an unpurified and desalted chimeric RNA sequence of de-esterified 2'-O-protected $(U_p)_{20}dT$.

FIG. 15B shows an RP-HPLC profile of an unpurified and desalted chimeric RNA sequence of fully 2'-O-deprotected $(U_p)_{20}dT$.

FIG. 15C shows an RP-HPLC profile of an unpurified and desalted chimeric RNA sequence of a fully 2'-O-deprotected $(U_p)_{20}dT$ control sequence.

FIG. 17A shows an RP-HPLC analysis of an unpurified, de-esterified, and desalted 2'-O-protected $(U_p)_{20}dT$ digest.

FIG. 17B shows RP-HPLC analysis of unpurified and desalted 2'-O-deprotected $(U_p)_{20}dT$ digest.

FIG. 17C shows RP-HPLC analysis of unpurified 2'-O-deprotected $(U_p)_{20}dT$ control sequence digest.

SEQUENCE LISTING

Figure 1C:
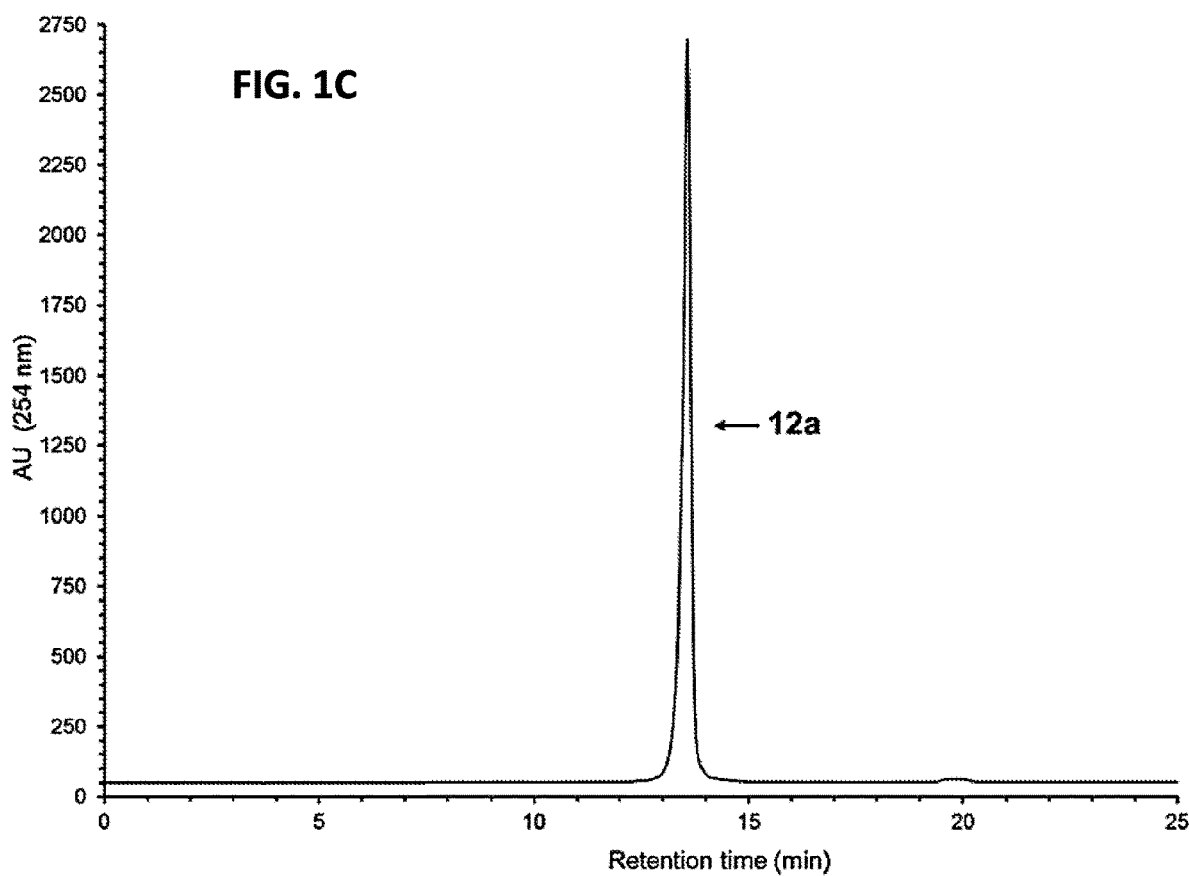
Figure 1D:
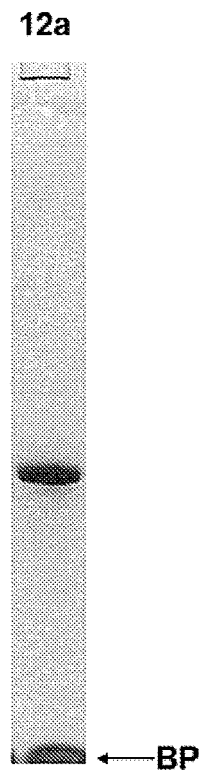
FIG. 1D shows the purity analysis of the solid-phase purified 12a by PAGE.
Figure 2C:
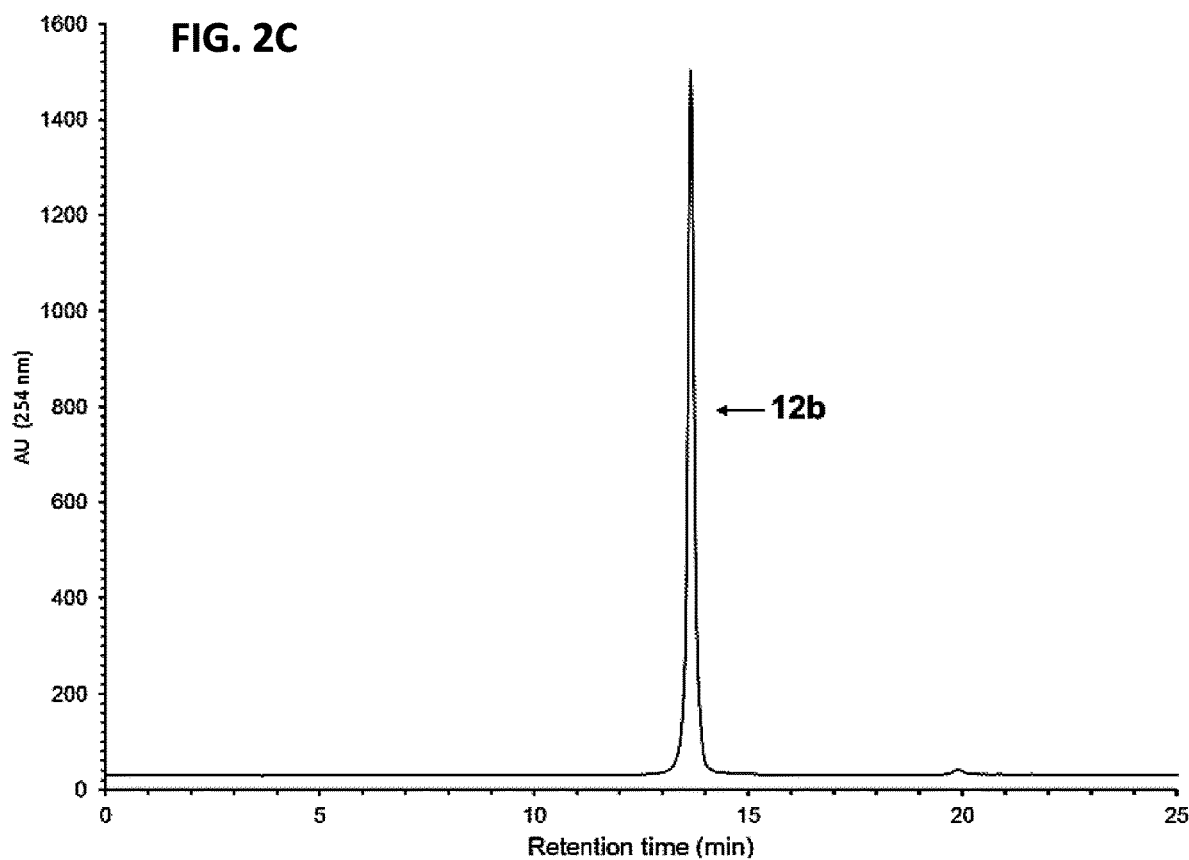
FIG. 2C shows the RP-HPLC analysis of solid-phase purified 12b that has been released from the support 11b.
Figure 2D:
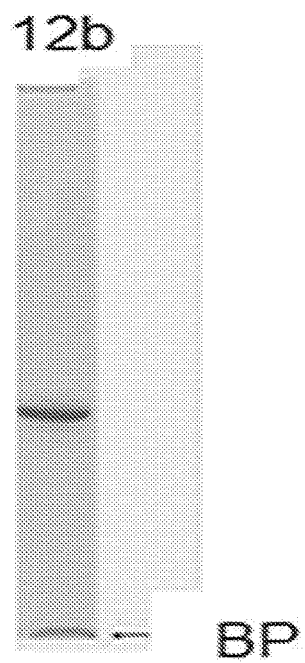
FIG. 2D shows the purity analysis of the solid-phase purified 12b by PAGE.
Figure 3C:
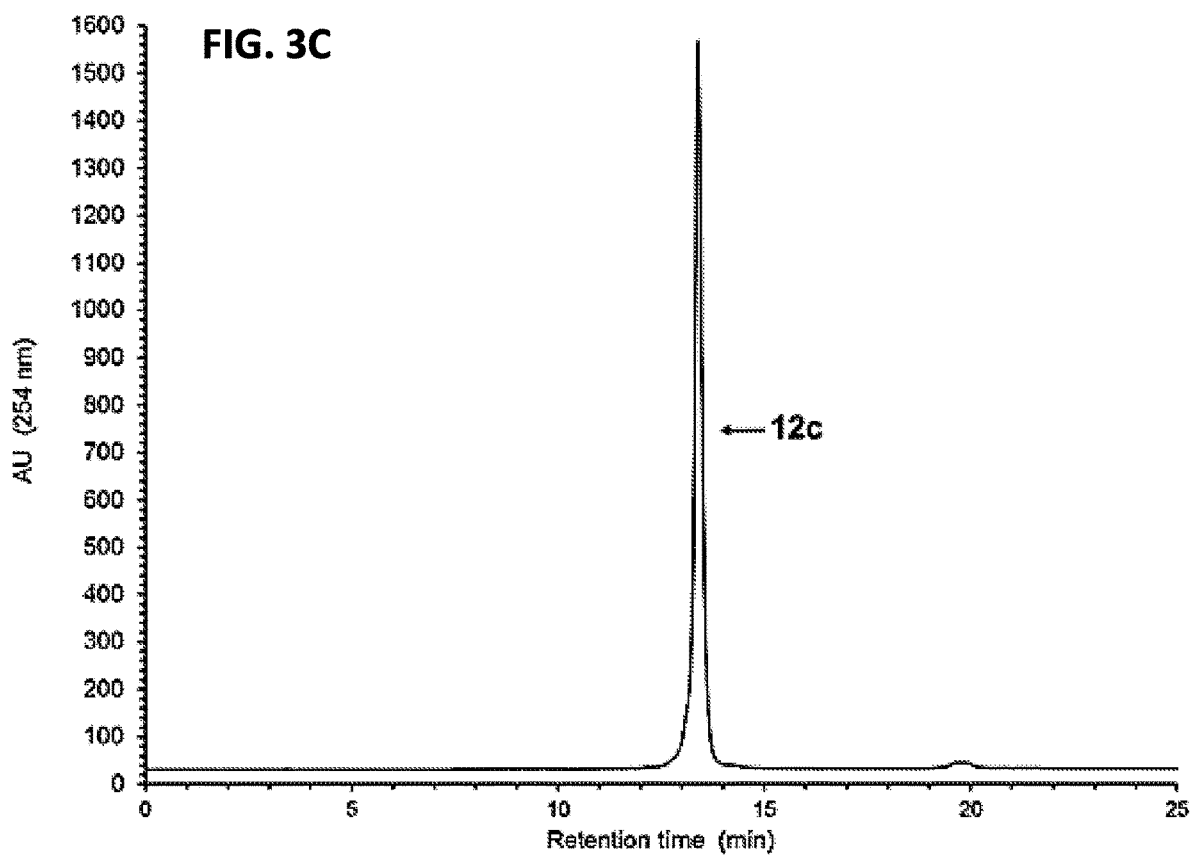
FIG. 3C shows the RP-HPLC analysis of solid-phase purified 12c that has been released from the support 11c.
Figure 3D:
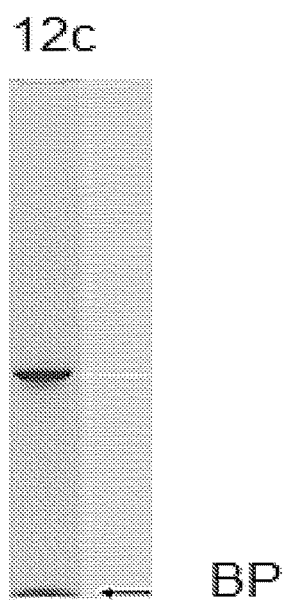
FIG. 3D shows the purity analysis of the solid-phase purified 12c by PAGE.

The nucleic acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jun. 28, 2017, 7 KB, which is incorporated by reference herein.

DETAILED DESCRIPTION

I. Definitions

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/ methods. When directly and explicitly distinguishing embodiments from discussed prior art, the embodiment numbers are not approximates unless the word "about" is recited. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the described elements in all possible variations thereof is encompassed by the invention unless otherwise indicated herein or otherwise clearly contradicted by context.

Unless explained otherwise, all technical and scientific terms used herein have the same meaning as commonly understood to one of ordinary skill in the art to which this disclosure belongs. When chemical structures are depicted or described, unless explicitly stated otherwise, all carbons are assumed to include hydrogen so that each carbon conforms to a valence of four. For example, in the structure on the left-hand side of the schematic below there are nine hydrogen atoms implied. The nine hydrogen atoms are depicted in the right-hand structure.

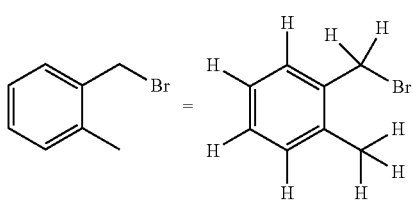

Sometimes a particular atom in a structure is described in textual formula as having a hydrogen or hydrogen atoms, for example —CH$_2$CH$_2$—. It will be understood by a person of ordinary skill in the art that the aforementioned descriptive techniques are common in the chemical arts to provide brevity and simplicity to description of organic structures.

Referring now to terminology used generically herein, the term "alkyl" means a straight-chain or branched alkyl substituent containing from, for example, 1 to about 6 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term "cycloalkyl," as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups such as methyl groups, ethyl groups, and the like.

The term "arylated alkyl" means an alkyl group substituted with an optionally substituted aryl group, containing from, for example 6 to 10 carbon atoms in the aryl group and 1 to about 6 carbon atoms in the alkyl group, preferably 6 carbon atoms in the aryl group and from 1 to about 4 carbon atoms in the alkyl group, and more preferably 6 carbon atoms in the aryl group and from 1 to about 2 carbon atoms in the alkyl group and wherein the alkyl group is connected to the rest of the compound. Arylated alkyl has the same meaning as arylalkyl.

The term "heterocyclyl," as used herein, refers to a monocyclic or bicyclic 5- or 6-membered ring system containing one or more heteroatoms selected from the group consisting of O, N, S, and combinations thereof. The heterocyclyl group can be any suitable heterocyclyl group and preferably can be an aliphatic heterocyclyl group. The heterocyclyl group can be a monocyclic heterocyclyl group or a bicyclic heterocyclyl group. Suitable heterocyclyl groups include morpholine, piperidine, tetrahydrofuryl, oxetanyl, pyrrolidinyl, and the like. The heterocyclyl or heteroaryl group is optionally substituted with 1, 2, 3, 4, or 5 substituents as recited herein such as with alkyl groups such as methyl groups, ethyl groups, and the like, halo groups such as chloro, or hydroxyl groups, wherein the optional substituent can be present at any open position on the heterocyclyl group.

The term "aryl" refers to an unsubstituted or substituted aromatic carbocyclic substituent, as commonly understood in the art, and the term "C$_6$-C$_{10}$ aryl" includes phenyl and naphthyl. It is understood that the term aryl applies to cyclic substituents that are planar and comprise 4n+2π electrons, according to Hückel's Rule.

The term "NR$^4$R$^5$" refers to a structure of the formula:

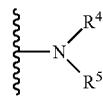

wherein, unless otherwise described, the R$^4$ and R$^5$ groups are each individually attached to the N atom and are not connected or otherwise bonded to each other.

The aminooxy function —ONH$_2$ includes both the free base and the acid addition salts thereof. Non-limiting examples of suitable acids for formation of acid addition salts of aminooxy functions include hydrochloric acid, sulfuric acid, and the like.

The term "protecting group" refers to a group attached to a functional group such as hydroxyl and/or that, when reversible, can be removed upon treatment with a suitable deprotecting agent. For example, a suitable protecting group for a phosphoramidite can be a 2-cyanoethyl group. Examples of suitable protecting groups for hydroxyl groups are as further disclosed herein. A permanent hydroxyl protecting group is one which remains intact while subjected to subsequent reaction steps. Non-limiting examples of permanent hydroxyl protecting groups include benzyl, methyl, and the like, which form benzyl and methyl ethers.

The terms "nucleoside" and "nucleotide" include moieties that contain not only the known purine and pyrimidine bases, e.g., adenine (A), thymine (T), cytosine (C), guanine (G), or uracil (U), but also other heterocyclic bases or nucleobases that have been modified. Such modifications include methylated purines or pyrimidines, acylated purines or pyrimidines, or other heterocycles. Non-limiting examples of such modifications include, for example, diaminopurine and derivatives thereof, inosine and derivatives thereof, alkylated purines or pyrimidines, acylated purines or pyrimidines, thiolated purines or pyrimidines, and the like, or modifications comprising addition of a protecting group such as acetyl, difluoroacetyl, trifluoroacetyl, isobutyryl, benzoyl, 9-fluorenylmethoxycarbonyl, phenoxyacetyl, dimethylformamidine, dibutylformamidine, N,N-diphenyl carbamate, substituted thiourea, and the like. The purine or pyrimidine base may also be an analog of the foregoing. Those skilled in the art will recognize suitable analogs that are described in the literature. Non-limiting example of typical analogs include, for example, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queuosine, inosine, 1-methylinosine, hypoxanthine, xanthine, 2-aminopurine, 6-hydroxyaminopurine, 6-thiopurine, and 2,6-diaminopurine.

The terms "nucleoside" and "nucleotide" further include moieties that contain not only conventional ribose and deoxyribose sugars and conventional stereoisomers, but other sugars as well, including L-enantiomers and α-anomers. Modified nucleosides or nucleotides can also include modifications on the sugar moiety, e.g., wherein one or more of the hydroxyl groups are replaced with halogen atoms, amine groups, or aliphatic groups, or are functionalized as esters, ethers, and the like. "Nucleotide analogs" and "nucleoside analogs" refer to molecules having structural features that are recognized in the literature as being mimetics, derivatives, having analogous structures, or other like terms, and include, for example, polynucleotides or oligonucleotides incorporating non-natural nucleotides, unnatural nucleotide mimetics such as 2'-modified nucleosides including but not limited to 2'-fluoro, 2'-O-alkyl, —O-alkylamino, —O-alkylalkoxy, protected —O-alkylamino, —O-alkylaminoalkyl, —O-alkyl imidazole, and polyethers of the formula (O-alkyl)$_m$ such as linear and cyclic polyethylene glycols (PEGs), and (PEG)-containing groups, locked nucleic acids (LNA), peptide nucleic acids (PNA), phosphorodiamidate morpholino oligomer (PMO) sequences, oligomeric nucleoside phosphonates, and any polynucleotide that has added substituent groups, such as protecting groups or linking groups.

As used herein, an activatable phosphorus-containing entity refers to a phosphoramidite or H-phosphonate group having suitable protective groups and capable of being activated for formation of P—O bonds with the 3'- or 5'-hydroxyl group of a deoxyribonucleoside or deoxyribonucleoside analog or ribonucleoside or ribonucleoside analog. In an embodiment, the activatable phosphorus-containing entity can be a phosphoramidite group or H-phosphonate group of the formula:

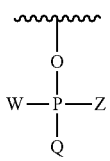

wherein W is a lone pair of electrons or an oxo function. When W is a lone pair of electrons, Z is $NR^4R^5$ wherein $R^4$ and $R^5$ are individually $C_1$-$C_6$ alkyl, $C_6$-$C_{10}$ arylated $C_1$-$C_6$ alkyl, or $C_3$-$C_8$ cycloalkyl containing 1 to 10 carbon atoms or $R^4$ and $R^5$ taken together with the nitrogen atom to which they are attached form a saturated 3-10 membered heterocyclic ring optionally including one or more additional heteroatoms selected from the group consisting of nitrogen, oxygen and sulfur, and Q is OT wherein T is a reversible or permanent hydroxyl protecting group. The resulting phosphoramidite group has the structure:

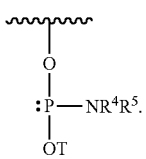

When W is an oxo function, Z is H and Q is O$^-$. The resulting H-phosphonate group has the structure:

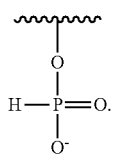

The reversible hydroxyl protecting group can be any suitable reversible hydroxyl protecting group. In a preferred embodiment, the reversible hydroxyl protecting group is a 2-cyanoethyl group.

For RNA synthesis (J of formula I through IV or Ia through IVa is $OR^7$), the 2'-hydroxy groups need to be protected with groups that can survive alkaline reaction conditions. The hydroxyl protecting groups can be reversible or permanent. The hydroxyl protecting groups can be any suitable protecting groups including ethers, silyl ethers, benzyl ethers, substituted benzyl ethers, acetals, thioacetals, ketals, acetalesters, esters, orthoesters and the like. Examples of suitable 2'-hydroxy protecting groups include t-butyldimethylsilyl (TBDMS), triisopropylsilyloxymethyl (TMM), or 2-cyanoethyloxymethyl (CEM) groups.

In some embodiments concerning RNA sequences, protection of the 3'-hydroxyl may improve the efficiency of the 5'-functionalization. Certain bulky protecting groups, such as TBDMS, when used to protect the 2'-hydroxyl, may block efficient protection at the 3'-hydroxyl. Accordingly, the 2'-hydroxyl protecting group may be selected to have a reduced steric bulk, compared to bulky protecting groups such as TBDMS. Exemplary protecting groups include, but are not limited to acetals, ethers, benzyl ethers, substituted benzyl ethers, thioacetals, ketals, acetalesters, esters, or orthoesters. One exemplary protecting group has a formula

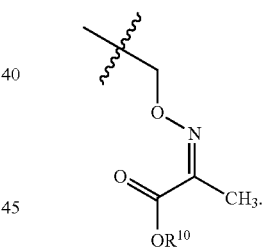

With respect to this formula, ⌇ denotes the site of attachment to the hydroxyl, and $R^{10}$ is H; alkyl, such as $C_{1-6}$alkyl, typically $C_{1-3}$alkyl, such as methyl, ethyl, n-propyl, or isopropyl; or cycloalkyl, such as $C_{3-8}$cycloalkyl; or $OR^{10}$ is O$^-$M$^+$, where M$^+$ is an alkali metal, such as K$^+$, Na$^+$, or Li$^+$. In certain embodiments, $R^{10}$ is ethyl.

II. Overview

The invention provides a method of purifying an oligonucleotide or an oligonucleotide analog composed of "b" nucleotides from a mixture comprising the oligonucleotide or oligonucleotide analog and at least one oligonucleotide or oligonucleotide analog composed of "a" nucleotides, wherein b≠a, which method comprises:

(i) providing a protected nucleoside or nucleoside analog of formula (I) or (Ia) functionalized with an activatable phosphorus-containing entity:

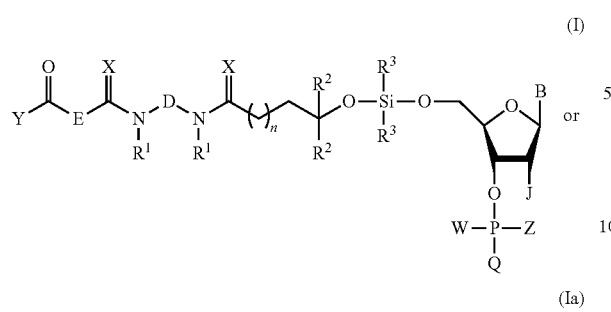
(I)

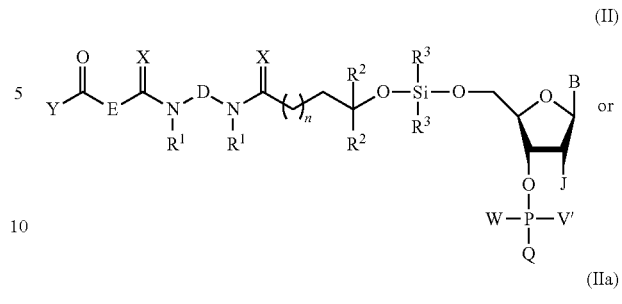
(II)

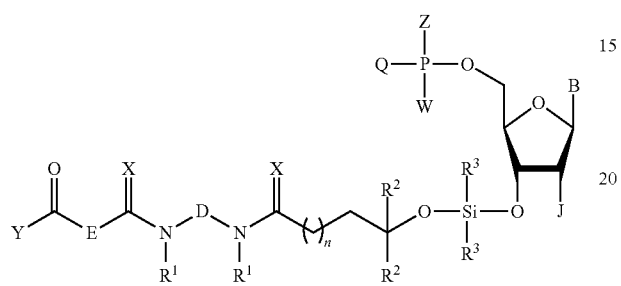
(Ia)

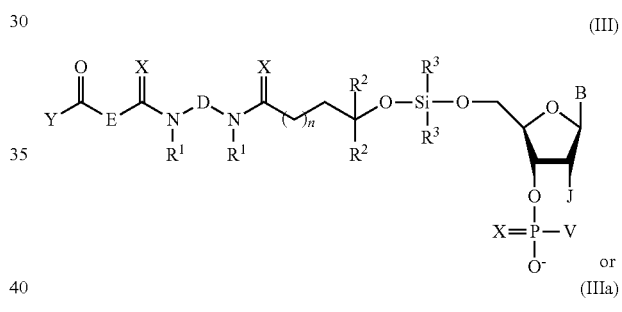
(IIa)

wherein B is an optionally protected nucleobase or an optionally protected nucleobase analog, D and E are independently $C_2$-$C_{10}$ alkanediyl, n is 1 to 4, $R^1$ is $C_1$-$C_6$ linear or branched alkyl or $C_3$-$C_8$ cycloalkyl, $R^2$ is hydrogen or linear or branched $C_1$-$C_6$ alkyl, $R^3$ is linear or branched $C_3$-$C_6$ alkyl, J is H or $OR^7$ wherein $R^7$ is a reversible or permanent hydroxyl protecting group, X is O or S, Y is H or $C_1$-$C_6$ linear alkyl, W is a lone pair of electrons or an oxo function, when W is a lone pair of electrons, Z is $NR^4R^5$ wherein $R^4$ and $R^5$ are individually $C_1$-$C_6$ alkyl, $C_6$-$C_{10}$ arylated $C_1$-$C_6$ alkyl, or $C_3$-$C_8$ cycloalkyl or $R^4$ and $R^5$ taken together with the nitrogen atom to which they are attached form a saturated 3-10 membered heterocyclic ring optionally including one or more additional heteroatoms selected from the group consisting of nitrogen, oxygen and sulfur, and Q is OT wherein T is a reversible or a permanent hydroxyl protecting group, and when W is an oxo function, Z is H and Q is O⁻, (ii) providing a mixture comprising an optionally protected first oligonucleotide or oligonucleotide analog V' composed of b-1 nucleotides or nucleotide analogs and having a free 5'-terminal OH group, wherein the first oligonucleotide V' comprises phosphate or phosphorothioate triester linkages, or a combination thereof, and wherein the first oligonucleotide V' is linked at its 3'-terminus to a solid support, wherein at least one oligonucleotide or oligonucleotide analog composed of "a" nucleotides is also linked to the solid support, (iii) coupling the first oligonucleotide V' with the protected nucleoside or nucleoside analog of formula (I) or (Ia), to provide a second oligonucleotide of the formula (II) or (IIa):

(iv) oxidizing or sulfurizing, optionally deprotecting, and cleaving the second oligonucleotide or oligonucleotide analog of the formula (II) or (IIa) from the solid support to form a mixture comprising a third oligonucleotide of the formula (III) or (IIIa):

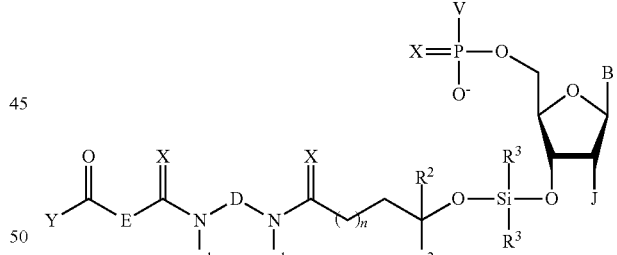
(III)

(IIIa)

wherein V is the moiety resulting after optional deprotection of the second oligonucleotide or oligonucleotide analog and wherein V is not linked to the solid support, (v) reacting the mixture comprising the third oligonucleotide or oligonucleotide analog of the formula (III) or (IIIa) with a silica-attached linker compound of the formula:

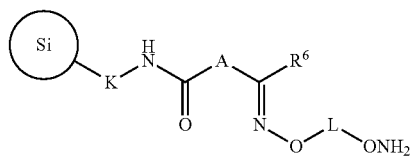

wherein A, K, and L are independently $C_2$-$C_{10}$ alkanediyl and $R^6$ is H, $C_1$-$C_6$ linear or branched alkyl, or $C_3$-$C_8$ cycloalkyl, and wherein

is silica, to form a linker-attached oligonucleotide or oligonucleotide analog of the formula (IV) or (IVa):

In certain embodiments, W is a lone pair of electrons. In certain embodiments, Z is $NR^4R^5$ wherein $R^4$ and $R^5$ are individually $C_1$-$C_6$ alkyl, $C_6$-$C_{10}$ arylated $C_1$-$C_6$ alkyl, and $C_3$-$C_8$ cycloalkyl containing 1 to 10 carbon atoms or $R^4$ and $R^5$ taken together with the nitrogen atom to which they are attached form a saturated 3-10 membered heterocyclic ring optionally including one or more additional heteroatoms selected from the group consisting of nitrogen, oxygen, and sulfur. In certain embodiments, Q is OT wherein T is a reversible or permanent hydroxyl protecting group. In cer-

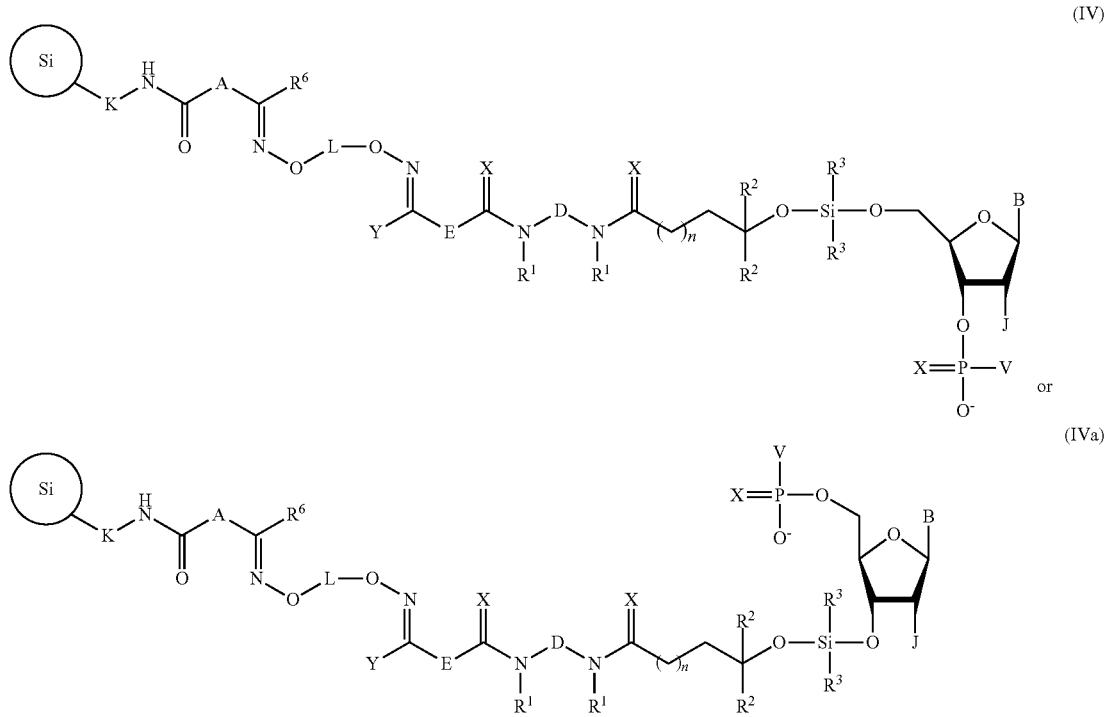

(vi) washing the linker-attached oligonucleotide of the formula (IV) or (IVa) with at least one solvent or a mixture of solvents to remove the oligonucleotide(s) or oligonucleotide analog(s) composed of "a" nucleotides, (vii) treating the linker-attached oligonucleotide or oligonucleotide analog of formula (IV) or (IVa) with a desilylation agent, and (viii) isolating the purified oligonucleotide or oligonucleotide analog composed of "b" nucleotides from the product of step (vii).

In certain preferred embodiments, A is 1,5-pentanediyl.
In certain preferred embodiments, K is 1,3-propanediyl.
In certain preferred embodiments, L is 1,3-propanediyl
In certain preferred embodiments, D is 1,2-ethanediyl.
In certain preferred embodiments, E is 1,5-pentanediyl.
In certain preferred embodiments, $R^2$ is methyl.
In certain preferred embodiments, $R^3$ is 2-propyl.
In certain preferred embodiments, $R^6$ is methyl.
In certain preferred embodiments, J is H.
In certain preferred embodiments, Y is methyl.
In certain preferred embodiments, the desilylation agent comprises fluoride ion.

In certain particular embodiments, the protected nucleoside or nucleoside analog is of formula (I).

tain embodiments, T is 2-cyanoethyl. In certain embodiments, the compounds of formulas (I) and (Ia) have the structures:

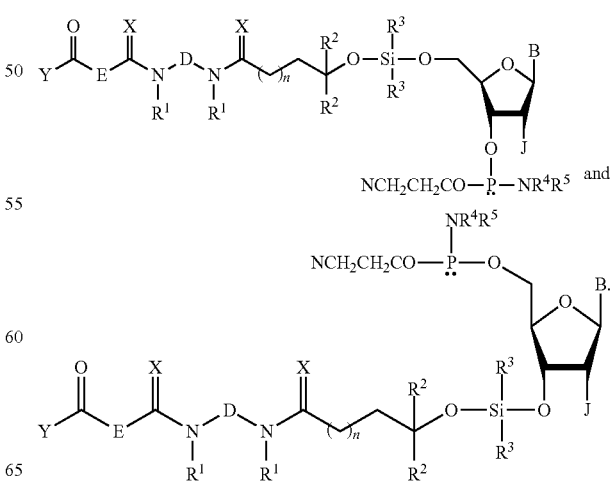

In certain preferred embodiments, the optionally protected first oligonucleotide or oligonucleotide analog is synthesized according to a solid-phase protocol.

The number of nucleotides "a" or "b" in the oligonucleotide or oligonucleotide analog can be from 2 to about 100,000, for example a or b can be from about 3 to about 50,000, from about 3 to about 25,000, from about 3 to about 10,000, from about 3 to about 5,000, from about 3 to about 1,000, from about 3 to about 500, from about 5 to about 500, from about 10 to about 500, or from about 10 to about 250.

Desirably, the inventive method provides a purified oligonucleotide or oligonucleotide analog that is about 80% pure or more, e.g., about 81% pure or more, about 82% pure or more, about 83% pure or more, about 84% pure or more, about 85% pure or more, about 86% pure or more, about 87% pure or more, about 88% pure or more, about 89% pure or more, about 90% pure or more, about 91% pure or more, about 92% pure or more, about 93% pure or more, about 94% pure or more, about 95% pure or more, about 96% pure or more, about 97% pure or more, about 98% pure or more, or about 99% pure or more. The purity of the oligonucleotide or oligonucleotide analog can be expressed as a percentage based on the area under the curve of an HPLC peak corresponding to the oligonucleotide or oligonucleotide relative to the total area under the curve for all components. The purity of the oligonucleotide or oligonucleotide analog can be determined using any suitable technique, for example, by reversed-phase HPLC or polyacrylamide gel electrophoresis (PAGE) with appropriate gel staining procedures and softwares for peak area or band intensity measurements.

In accordance with an embodiment, the invention provides a compound of the formula (I):

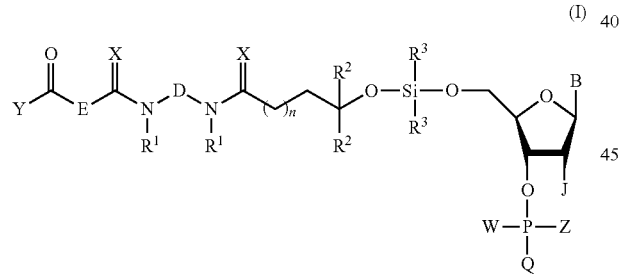

(I)

wherein B is an optionally protected nucleobase or optionally protected nucleobase analog, D and E are independently $C_2$-$C_{10}$ alkanediyl, n is 1 to 4, $R^1$ is $C_1$-$C_6$ linear or branched alkyl or $C_3$-$C_8$ cycloalkyl, $R^2$ is hydrogen or $C_1$-$C_6$ linear or branched alkyl or $C_3$-$C_8$ cycloalkyl, $R^3$ is linear or branched $C_3$-$C_6$ alkyl, J is H or $OR^7$ wherein $R^7$ is a reversible or permanent hydroxyl protecting group, X is O or S, Y is H or linear $C_1$-$C_6$ alkyl, W is a lone pair of electrons, and Z is $NR^4R^5$ wherein $R^4$ and $R^5$ are individually $C_1$-$C_6$ alkyl, $C_6$-$C_{10}$ arylated $C_1$-$C_6$ alkyl, or $C_3$-$C_8$ cycloalkyl containing 1 to 10 carbon atoms or $R^4$ and $R^5$ taken together with the nitrogen atom to which they are attached form a saturated 3-10 membered heterocyclic ring optionally including one or more additional heteroatoms selected from the group consisting of nitrogen, oxygen and sulfur, and Q is OT wherein T is a reversible hydroxyl protecting group.

In certain preferred embodiments, D is 1,2-ethanediyl.

In certain preferred embodiments, E is 1,5-pentanediyl.

In certain preferred embodiments, $R^1$ is methyl.

In certain preferred embodiments, $R^2$ is methyl.

In certain preferred embodiments, $R^3$ is 2-propyl.

In certain preferred embodiments, J is H. In other embodiments, J is $OR^7$ where $R^7$ is a hydroxyl protecting group, and may have a formula

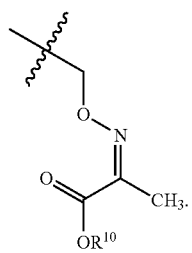

In certain preferred embodiments, Y is methyl.

In particular embodiments, the compound is:

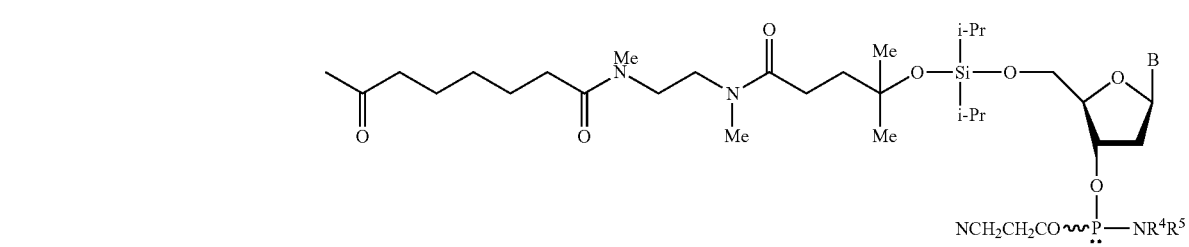
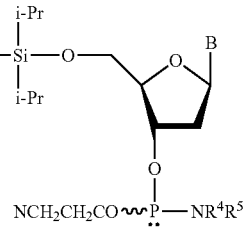

In an embodiment, the invention provides a method for preparing the compound of formula (I) comprising the steps of:

(i) providing a compound of the formula (1):

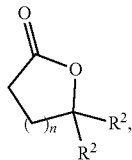
(1)

(ii) reacting the compound of step (i) with a compound of the formula:

R¹HN-D-NHR¹ to provide a compound of the formula (2):

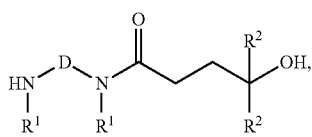
(2)

(iii) reacting the compound of formula (2) with a compound of the formula:

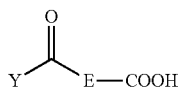

to provide a compound of formula (3):

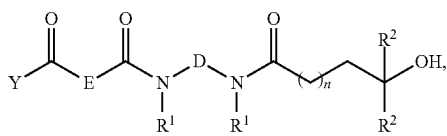
(3)

(iv) reacting the compound of formula (3) with a compound of the formula: $(R^3)_2SiX'_2$, wherein X' is a leaving group, to provide a compound of formula (4):

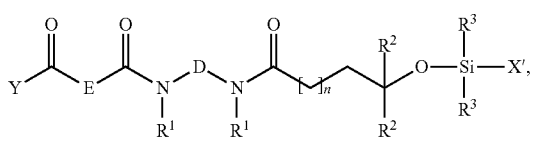
(4)

(v) reacting the compound of formula (4) with a nucleobase protected 2'-deoxyribonucleoside or nucleobase-protected 2'-O-protected ribonucleoside or a nucleobase-protected and carbohydrate modified analog thereof to provide a compound of the formula (5):

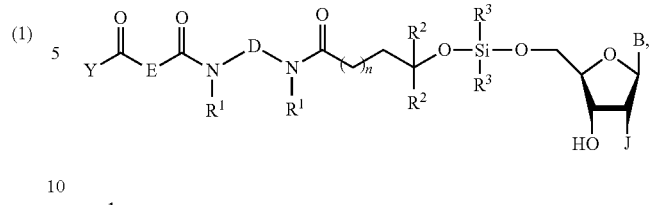
(5)

and (vi) reacting the compound of formula (5) with $[R^4R^5N]_2POCH_2CH_2CN$ or $R^4R^5NP(X')OCH_2CH_2CN$ wherein X' is a monovalent leaving group to provide a compound of the formula (6):

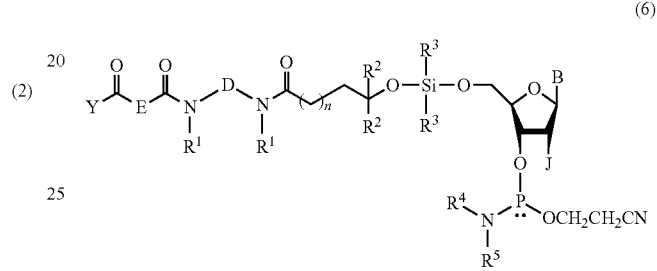
(6)

In accordance with an embodiment, the invention provides a capture support of formula (9):

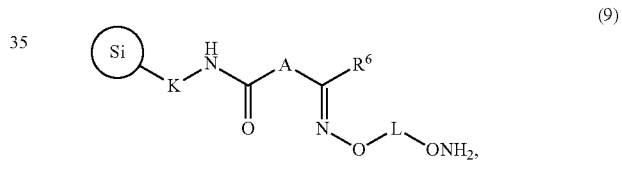
(9)

wherein A, K, and L are independently $C_2$-$C_{10}$ alkanediyl and $R^6$ is H, $C_1$-$C_6$ linear or branched alkyl, or $C_1$-$C_6$ cycloalkyl, and wherein

is silica.

In certain embodiments, $R^6$ is methyl.

In certain embodiments, A is 1,5-pentanediyl.

In certain embodiments, K and L are individually 1,3-propanediyl.

In a particular embodiment, the compound is:

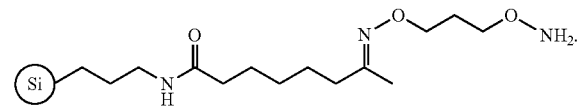

In an embodiment, the invention provides a method for preparing the capture support of formula (9) comprising the steps of:

(i) providing a functionalized silica gel of the formula (10):

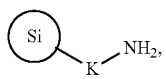

(ii) reacting the functionalized silica gel of the formula (10) with a compound of the formula:

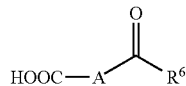

to provide a compound of formula (11):

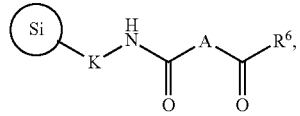

and (iii) reacting the compound of formula (11) with a compound of the formula:

$H_2NO-L-ONH_2$ to provide the capture support of formula (9).

III. Chemistry

A simple and efficient process for the purification of phosphorothioate and native DNA and RNA sequences is described herein. An embodiment of this process consists of functionalizing commercial aminopropylated silica gel with aminooxyalkyl functions to enable capture of nucleic acid sequences carrying a 5'-siloxyl ether linker with a "keto" function through an efficient oximation reaction. Deoxyribonucleoside phosphoramidites functionalized with the capture 5'-siloxyl ether linker have been prepared with yields in the range of 75-83% and incorporated last into the solid-phase assembly of DNA sequences. Capture of the nucleobase- and phosphate-deprotected DNA sequences released from the synthesis support is demonstrated to proceed near quantitatively. After washing off shorter than full length DNA sequences from the capture support, the purified DNA sequences are released from the support upon treatment with tetra-n-butylammonium fluoride in dry DMSO. The purity of the released DNA sequences is about or 98%. The scalability and high throughput of the solid-phase purification process is demonstrated without sacrificing purity of the DNA sequences.

Figure 18:
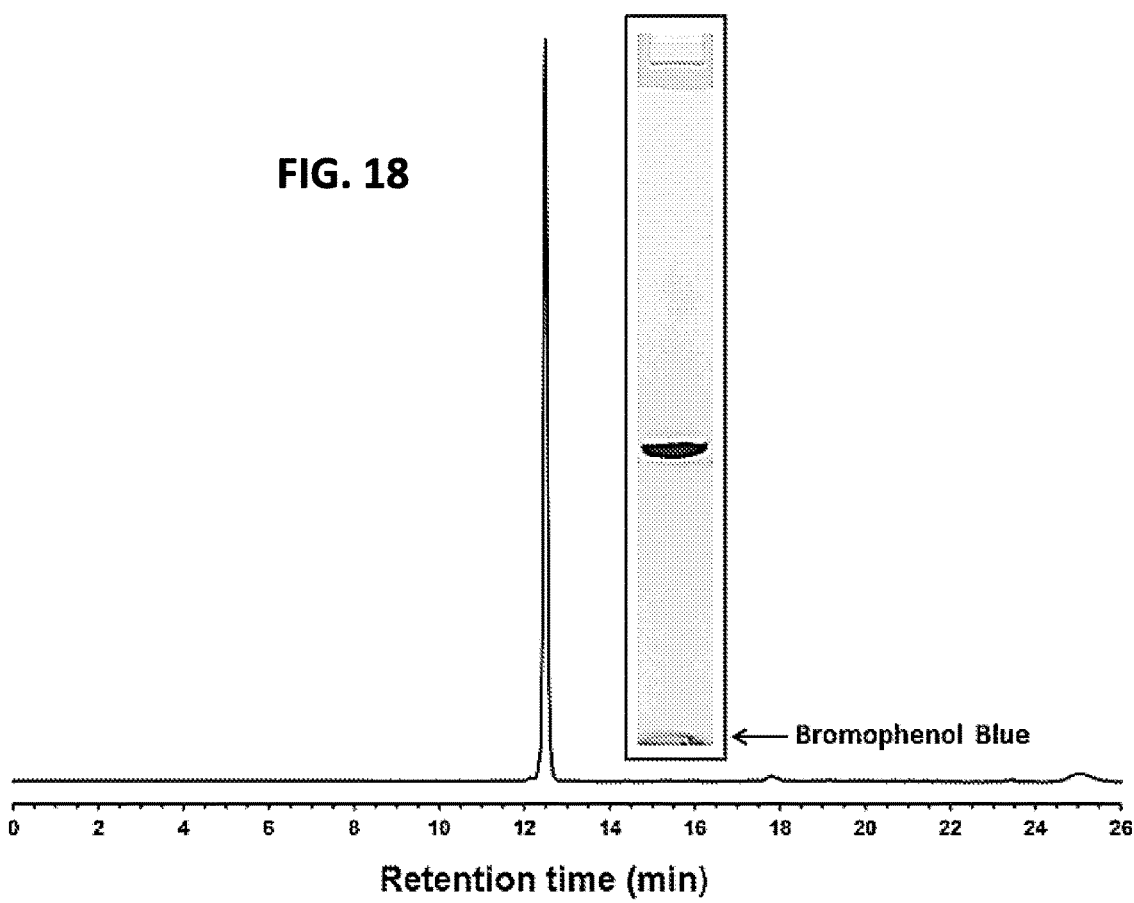
FIG. 18 shows electrophoretic and RP-HPLC chromatographic data for RNA sequence 2'-OMe-r(UpCpApCpUp GpUpGpApApUpCpGpApUpGpCpCpApU), illustrating that the disclosed method can successfully purify native RNA sequences.
Figure 19:
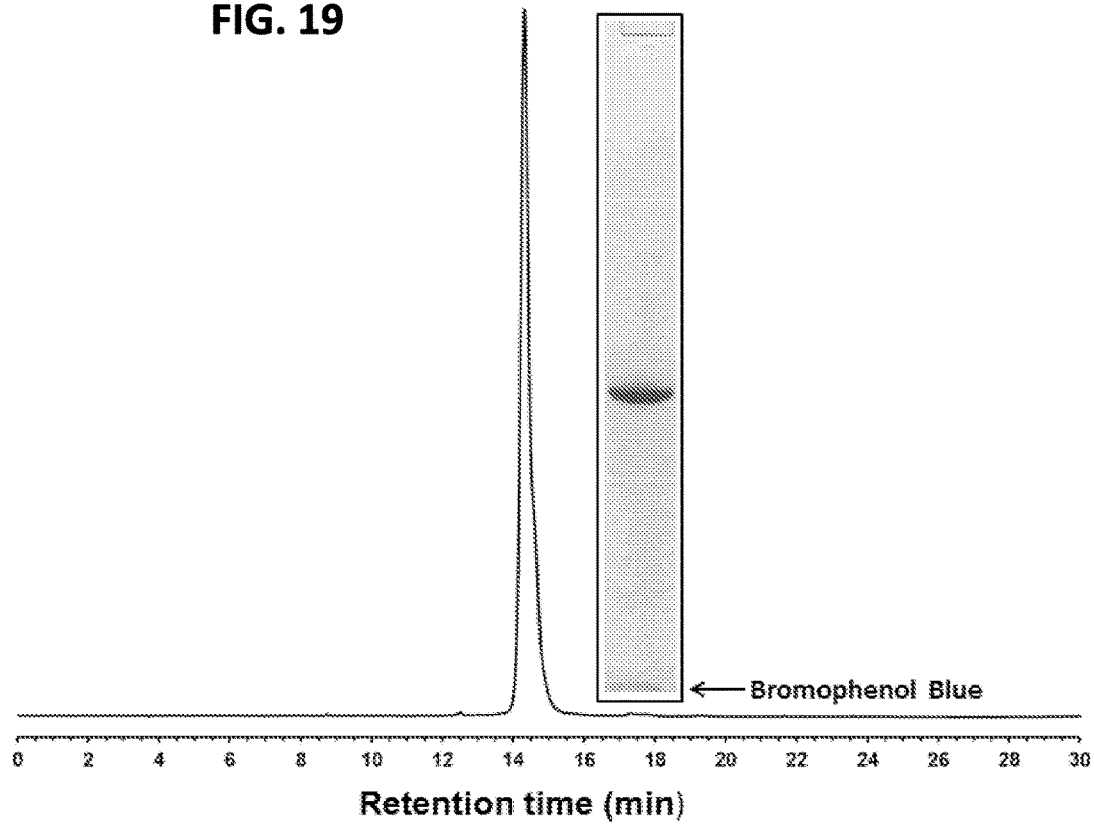
FIG. 19 shows electrophoretic and RP-HPLC chromatographic data for RNA sequence 2'-OMe-r(UpsCpsApsCps UpsGpsUpsGpsApsApsUpsCpsGpsApsUpsGpsCpsCps ApsU), illustrating that the disclosed method can successfully purify phosphorothioate RNA sequences.

Phosphorothioate and native RNA sequences are prepared using a similar method. Typically, the 2'-hydroxyl is protected by a suitable protecting group, as described herein. FIGS. 18 and 19 provide electrophoretic and RP-HPLC chromatographic data for RNA sequences 2'-OMe-r(UpCp ApCpUpGpUpGpApApUpCpGpApUpGpCpCpApU) and 2'-OMe-r(UpsCpsApsCpsUpsGpsUpsGpsApsApsUpsCps-GpsApsUpsGpsCpsCpsApsU), respectively, that were prepared and purified by the disclosed method.

A. Synthesis of Capture Support 3-aminopropyl-functionalized silica gel was identified as a suitable support for the intended purpose; the support is commercially available and loaded with about 1 mmol of primary aminopropyl functions per gram of support. As shown in Scheme 1, the functionalization of the aminopropylated support began with the reaction of 7-oxooctanoic acid (1) with a coupling agent such as 1,1'-carbonyldiimidazole in an appropriate solvent such as THF to provide the ketoalkyl amidoalkylated support 2; unreacted amino functions have been inactivated upon reaction with excess acetic anhydride in dry pyridine.

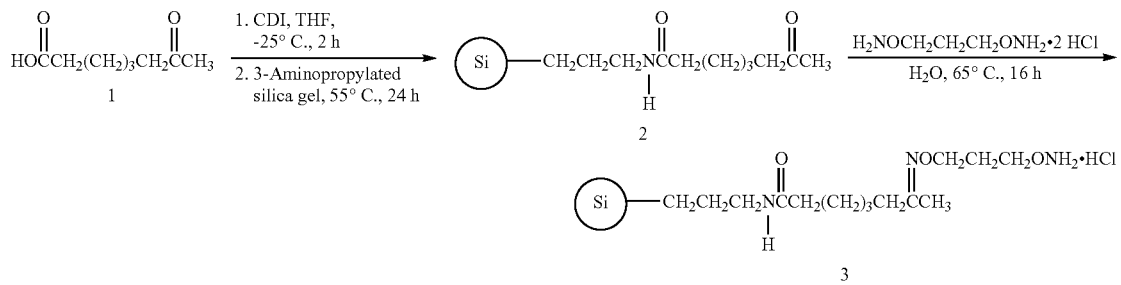

Scheme 1. Preparation of the capture support 3.

Abbreviations: CDI, 1,1'-carbonyldiimidazole; Si, 3-aminopropylated silica gel.

The support 2 is then suspended in a solution of an appropriate bishydroxylamine such as O,O'-1,3-propanediylbishydroxylamine dihydrochloride in H$_2$O to provide the aminooxy-functionalized support 3. The selection of the aminooxy group for the functionalization of support 3 is based on the high reactivity of this function by virtue of the well-known α-effect with carbonyl groups. The concentration of aminooxy functions covalently bound to support 3 has been determined upon reaction of the 4-monomethoxytritylated ketone 6c with 3 and subsequent release of the 4-monomethoxytrityl cation under acidic conditions; spectrophotometric measurement of the yellow-colored cation at 478 nm reveals an aminooxy concentration of 146±7 μmoles per gram of support 3.

B. Synthesis of Linker Compound

As shown in Scheme 2, the linker compound 6c is prepared from the 4-monomethoxytritylation of 6a, which was obtained from the reaction sequence 4a→5a. Butyrolactones 4a or 4b can be reacted with a suitable bis(methylamino)alkane such as N,N'-dimethylethylenediamine in water to form monoamides 5a or 5b. Acylation of amides 5a or 5b with a keto acid such as 7-oxooctanoic acid can be accomplished by reaction with a dehydration reagent such as carbonyldiimidazole (CDI) in a suitable solvent such as THF to provide keto diamides 6a or 6b. Tritylation of 6a with 4-monomethoxytrityl chloride in a suitable solvent such as dry pyridine provides the tritylated compound 6c. The concentration of aminooxy functions covalently bound to support 3 has been determined upon reaction of the 4-monomethoxytritylated ketone 6c with 3 and subsequent release of the 4-monomethoxytrityl cation under acidic conditions; spectrophotometric measurement of the yellow-colored cation at 478 nm reveals an aminooxy concentration of 146±7 µmoles per gram of support 3. Although the reaction of aminooxy functions with carbonyls groups have been shown to produce stable oxime ethers with a variety of nucleosides and nucleic acid sequences, oximation reactions have not been used, to the best of our knowledge, for solid-phase purification of nucleic acid sequences.

Scheme 2. Synthesis of linkers to be used for the solid-phase capture of DNA sequences or measuring the concentration of aminooxy functions conjugated to support 3.

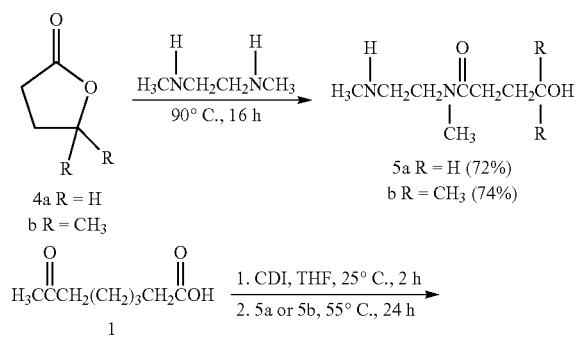

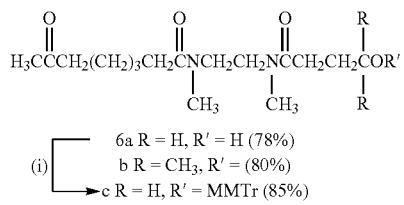

Conditions: (i) MMTr—Cl, dry pyridine, 25° C., 4 h. Abbreviations: CDI, 1,1'-carbonyldiimidazol; MMTr, 4-monomethoxytrityl.

C. Synthesis of Protected Nucleoside or Nucleoside Analog of Formula (I) or (Ia) Functionalized with an Activatable Phosphorus-Containing Entity.

The conjugation of 6b to the 5'-hydroxy function of 2'-deoxythymidine and N-protected-2'-deoxyribonucleosides (7a-d) is performed through the formation of a diisopropylsiloxyl linkage upon reaction with equimolar amounts of dichlorodiisopropylsilane in the presence of imidazole and has resulted in the production of the 5'-O-diisopropylsiloxyl ether derivatives 8a-d (Scheme 3) with yields in the range of 50% to 70% after silica gel purification. The alcohols 5a-b and 6a-b, the 4-methoxytrityl ether 6c and the silica gel-purified 5'-functionalized deoxyribonucleosides 8a-d have been fully characterized by $^1$H-, $^{13}$C-NMR spectroscopies and by high resolution mass spectrometry (HRMS); the characterization data are presented in the Examples and figures. The purity of 8a-d has been assessed by RP-HPLC. It should be noted that two rotameric tertiary amides in each of 8a-d have contributed to the high complexity of their $^1$H- and $^{13}$C-NMR spectra.

Scheme 3. Synthesis of 5'-functionalized deoxyribonucleosides (8a-d) and deoxyribonucleoside phosphoramidites (9a-d) for solid-phase capture of DNA sequences.

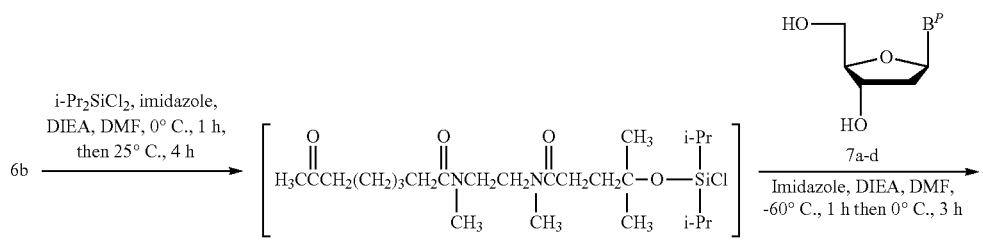

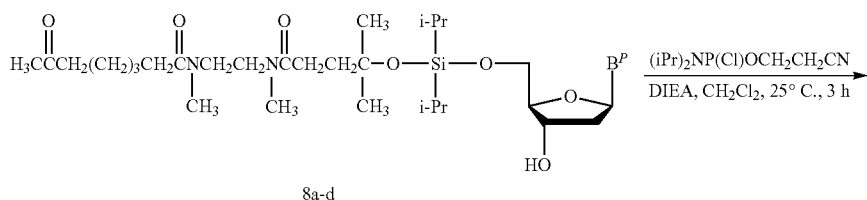

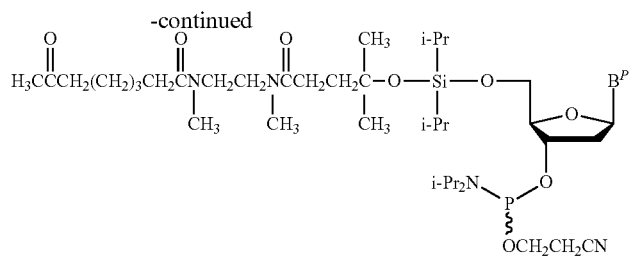

9a-d

Abbreviations: DIEA, N,N-diisopropylethylamine; $B^P$, (a) $N^6$-benzoyladenin-9-yl, (b) $N^4$-benzoylcytosin-1-yl, (c) $N^2$-isobutyrylguanin-9-yl or (d) thymin-1-yl; i-Pr, isopropyl; DMF, N,N-dimethylformamide.

Phosphitylation of 8a-d (Scheme 3) is performed in a suitable solvent such as anhydrous $CH_2Cl_2$ using commercial 2-cyanoethyl N,N-diisopropylchlorophosphoramidite in the presence of a suitable base such as N,N-diisopropylethylamine. Given that silica gel purification of the nucleoside phosphosphoramites 9a-d is conducted in the presence of triethylamine in order to prevent premature activation of the phosphoramidites when exposed to the inherent acidity of silica gel, it is advantageous that residual triethylamine be removed from 9a-d. Neutralization of 1H-tetrazole or any other acidic activator by triethylamine will result in decreased coupling efficiency of the phosphoramidites during the course of solid-phase DNA synthesis. Lyophilization of frozen 9a-d benzene solutions, under high vacuum, has been found effective for removing residual triethylamine from phosphoramidite monomers. Triethylamine-free deoxyribonucleoside phosphoramidites (9a-d) have been isolated as viscous oils, the yields of which being in the range of 75-83%. These phosphoramidites have been satisfactorily characterized by $^{31}P$ NMR spectroscopy and HRMS; the characterization data are presented in the Experimental section. As discussed above, the two rotameric tertiary amides within 8a-d have not only contributed to the complexity of their $^1H$- and $^{13}C$-NMR spectra but have also added to the complexity of the diastereomeric $^{31}P$ NMR signals recorded for 9a-d. It should also be emphasized that the presence of adventitious moisture in 9a-d and commercial phosphoramidites will result in lower phosphoramidite coupling efficiencies. It is therefore recommended that all the deoxyribonucleoside phosphoramidites needed for solid-phase synthesis of nucleic acid sequences be thoroughly dry, i.e., dried overnight in a desiccator containing an efficient drying agent (e.g., phosphorus pentoxide) under high vacuum prior to use.

Consequently, comparing side-by-side the: (i) chemical shifts and multiciplicity of the $^1H$ NMR signals; (ii) chemical shifts of the $^1H$-decoupled $^{13}C$- and $^{31}P$-NMR signals, where applicable, and (iii) HRMS data appears to be the simplest approach to support reproducibility in the preparation of 8a-d.

D. Solid-Phase Synthesis of 5'-Functionalized Phosphorothioate and Native DNA Sequences The solid-phase synthesis of phosphorothioate and native DNA sequences (10a-d and 10e-f, respectively) can be conducted using commercial long-chain alkylamine controlled-pore glass support (LCAA-CPG) according to standard protocols (see, for example, Iyer, R. P.; Phillips, L. R.; Egan, W.; Regan, J. B.; Beaucage, S. L. J. Org. Chem. 1990, 55, 4693-4699) as shown in Scheme 4 with the following exception: the capping step is performed after the oxidation reaction. The phosphite triester function can then be oxidized using 0.05 M 3H-1,2-benzodithiol-3-one 1,1-dioxide in MeCN or 0.02 M iodine solution in THF/pyridine/water for phosphorothioate or native DNA sequences, respectively. It is advantageous that the coupling efficiency of phosphoramidites 9a-d and the capping of unreacted 5'-hydroxy functions be optimal for solid-phase purification of DNA sequences; less than optimal coupling and capping reactions will result in poorer recovery of solid-phase-purified DNA sequences. In this regard, the coupling time of DNA phosphoramidites 9a-d has been extended to 180 s to ensure the highest coupling efficiency of these 5'-sterically-demanding phosphoramidite monomers. Post-synthesis deprotection and release of the DNA sequences 10a-f from LCAA-CPG have been performed under basic conditions according to standard protocols (see, for example, Ellington, A; Pollard, Jr., J. D. In Current Protocols in Molecular Biology; John Wiley & Sons, New York, 1998, pp. 2.11.1-2.11.25).

Scheme 4. Capture of crude DNA sequence 10a-f by the solid support 3 and release of these sequences from the solid support 11a-f as purified sequences 12a-f.

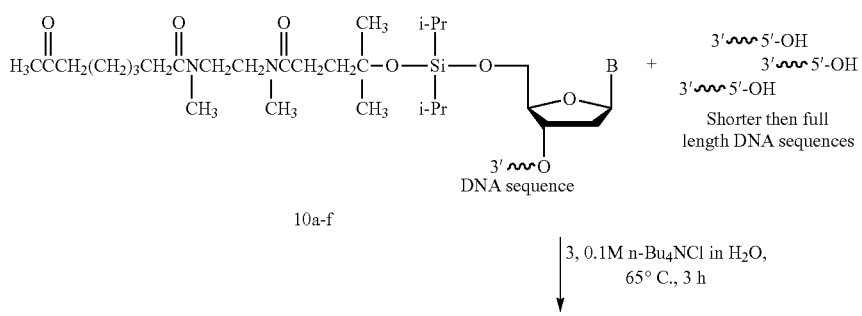

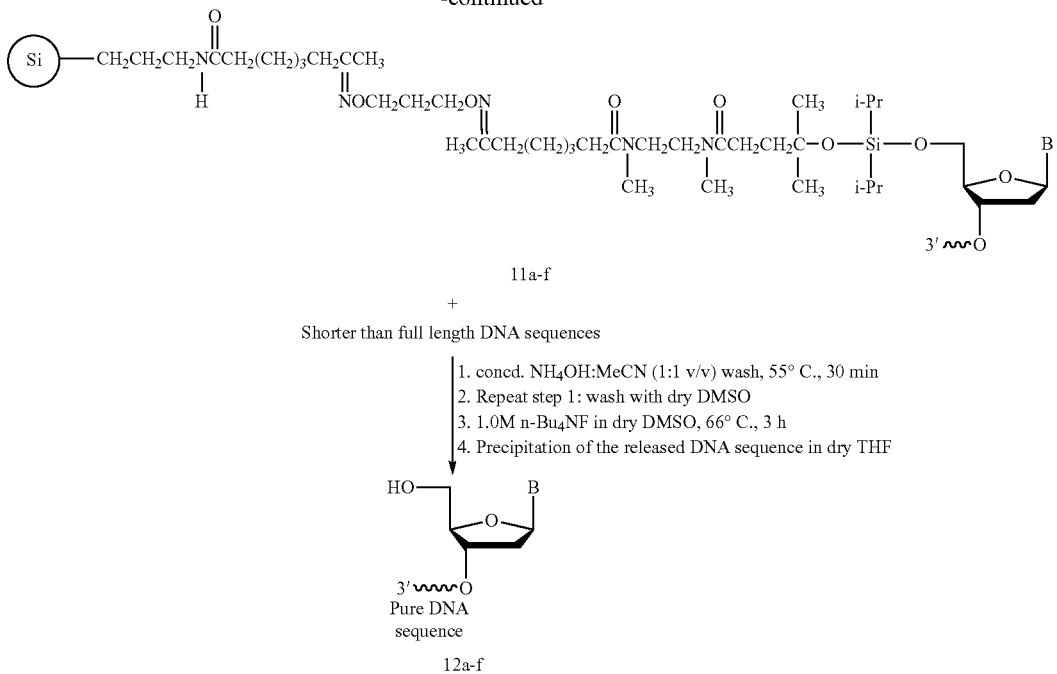

11a-f

+

Shorter than full length DNA sequences 1. concd. NH₄OH:MeCN (1:1 v/v) wash, 55° C., 30 min
2. Repeat step 1: wash with dry DMSO
3. 1.0M n-Bu₄NF in dry DMSO, 66° C., 3 h
4. Precipitation of the released DNA sequence in dry THF Pure DNA sequence
12a-f Abbreviations: Si, 3-aminopropylated silica gel; B, adenin-9-yl, cytosin-1-yl, guanin-9-yl or thymin-1-yl;
12a, 5'-d(A$_{PS}$C$_{PS}$A$_{PS}$C$_{PS}$T$_{PS}$G$_{PS}$T$_{PS}$G$_{PS}$A$_{PS}$A$_{PS}$T$_{PS}$C$_{PS}$G$_{PS}$A$_{PS}$T$_{PS}$G$_{PS}$C$_{PS}$C$_{PS}$A$_{PS}$T) (SEQ ID NO. 7);
12b, 5'-d(C$_{PS}$T$_{PS}$C$_{PS}$C$_{PS}$G$_{PS}$T$_{PS}$A$_{PS}$C$_{PS}$C$_{PS}$T$_{PS}$T$_{PS}$A$_{PS}$C$_{PS}$G$_{PS}$T$_{PS}$C$_{PS}$T$_{PS}$T$_{PS}$G$_{PS}$T) (SEQ ID NO. 8);
12c, 5'-d(G$_{PS}$T$_{PS}$G$_{PS}$A$_{PS}$A$_{PS}$G$_{PS}$T$_{PS}$A$_{PS}$G$_{PS}$C$_{PS}$G$_{PS}$A$_{PS}$A$_{PS}$C$_{PS}$G$_{PS}$T$_{PS}$G$_{PS}$A$_{PS}$A$_{PS}$G$_{PS}$T) (SEQ ID NO.9);
12d, 5'-d(T$_{PS}$A$_{PS}$T$_{PS}$C$_{PS}$C$_{PS}$G$_{PS}$T$_{PS}$A$_{PS}$G$_{PS}$C$_{PS}$T$_{PS}$A$_{PS}$A$_{PS}$C$_{PS}$G$_{PS}$T$_{PS}$C$_{PS}$A$_{PS}$G$_{PS}$T) (SEQ ID NO.10);
12e, 5'-d(A$_{P}$C$_{P}$A$_{P}$C$_{P}$T$_{P}$G$_{P}$T$_{P}$G$_{P}$A$_{P}$A$_{P}$T$_{P}$C$_{P}$G$_{P}$A$_{P}$T$_{P}$G$_{P}$C$_{P}$C$_{P}$A$_{P}$T) (SEQ ID NO. 11);
12f, 5'-d(T$_{P}$C$_{P}$A$_{P}$C$_{P}$T$_{P}$G$_{P}$T$_{P}$G$_{P}$A$_{P}$A$_{P}$T$_{P}$C$_{P}$G$_{P}$A$_{P}$T$_{P}$G$_{P}$C$_{P}$A$_{P}$A$_{P}$T$_{P}$T$_{P}$G$_{P}$C$_{P}$A$_{P}$C$_{P}$T$_{P}$G$_{P}$T$_{P}$G$_{P}$A$_{P}$A$_{P}$T$_{P}$C$_{P}$G$_{P}$A$_{P}$T$_{P}$G$_{P}$C$_{P}$C$_{P}$A$_{P}$T$_{P}$C$_{P}$A$_{P}$C$_{P}$T$_{P}$G$_{P}$T$_{P}$G$_{P}$A$_{P}$A$_{P}$T$_{P}$C$_{P}$G$_{P}$A$_{P}$T$_{P}$G$_{P}$C$_{P}$C$_{P}$A$_{P}$T) SEQ ID NO. 12).
PS, phosphorothioate dieste; P, phosphate diester.

E. Solid-Phase Capture and Release of Phosphorothioate and Native DNA Sequences.

Upon release from the LCAA-CPG support, the aqueous ammonia solution containing the crude DNA sequence 10a-f and shorter than full length sequences (Scheme 4) is evaporated to half its original volume. Solid tetra-n-butylammonium chloride and the capture support 3 are then sequentially added to the aqueous solution of DNA sequences; the suspension is kept at 65° C. over a period of 3 h. RP-HPLC analysis of the pre- and post-capture solutions of each DNA sequence shows that the oximation reaction resulting in the capture of each 5'-functionalized DNA sequence is in all cases near complete. The solid support 11a-f is then treated twice with a warm (55° C.) solution of aqueous ammonia in acetonitrile (Scheme 4, step 1) to wash off unbound shorter than full length DNA sequences by filtration. Exposure of the support 11a-f to 1.0 M tetra-n-butylammonium fluoride (TBAF) in dry DMSO at 65° C. over a period of 3 h is sufficient to release the DNA sequences 12a-f from their respective supports. The DNA sequences are isolated by precipitation in dry THF and characterized by ESI-TOF MS. The purity of these sequences has been evaluated by RP-HPLC and by polyacrylamide gel electrophoresis (PAGE) under denaturing conditions, as shown in FIGS. 1C and 1D, 2C and 2D, 3C and 3D, 4C and 4D, 5C and 5D, and 6C and 6D, for 12a-12f, respectively.

Efficiency of DNA Sequence Recovery from the Solid-Phase Purification Process

The most meaningful and reliable approach to measure efficiency of the solid-phase purification of nucleic acid sequences is to use a spectrophotometrically measured amount of a RP-HPLC purified and desalted 5'-functionalized DNA sequence (10a) and subject it to capture by the solid support 3 under the conditions described above. Upon exposure of the solid-support 11a to TBAF and subsequent precipitation of the released DNA sequence under the conditions reported in the experimental section, the total amount of 12a, as measured by UV spectroscopy at 260 nm, is 90% the amount of 10a used for capture.

Figure 8:
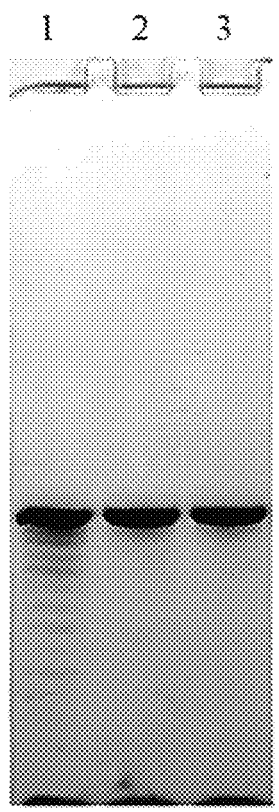
FIG. 8 shows PAGE analysis of the purity of phosphorothioate DNA sequence 12a recovered from the solid-phase purification process described herein and from the RP-HPLC purification process. Lane 1 shows unpurified 12a. Lane 2 shows PAGE analysis of solid-phase recovery of 12a obtained from RP-HPLC-purified 10a. Lane 3 shows PAGE analysis of recovery of 12a from RP-HPLC-purified 10a that had been exposed to TBAF.

In order to assess whether the solid supports 3 and/or 11 did or did not detrimentally affect the quality of the DNA sequence during the capture and release steps of the solid-phase purification process, the purity of 12a has been evaluated by PAGE and compared to that of unpurified 12a and of 12a obtained directly from treatment of RP-HPLC-purified 10a with TBAF under conditions identical to those used for the release of 12a from 11a. FIG. 8 clearly shows that purity of 12a that had been subjected to the solid-phase purification process is highly comparable to the purity of 12a that had not been in contact with the capture solid support 3.

Figure 10A:
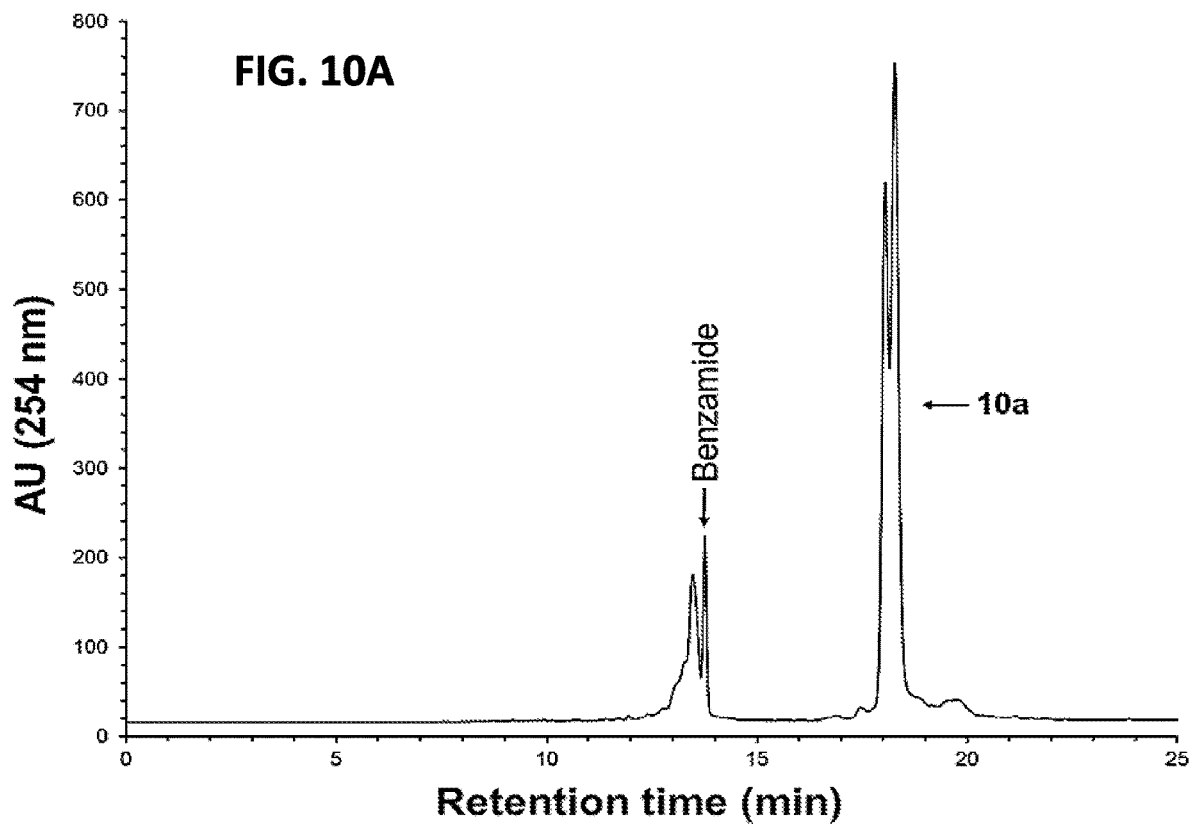
FIG. 10A shows the RP-HPLC profile of unpurified 10a (5'-functionalized 12a) on 10-fold scale up.
Figure 10B:
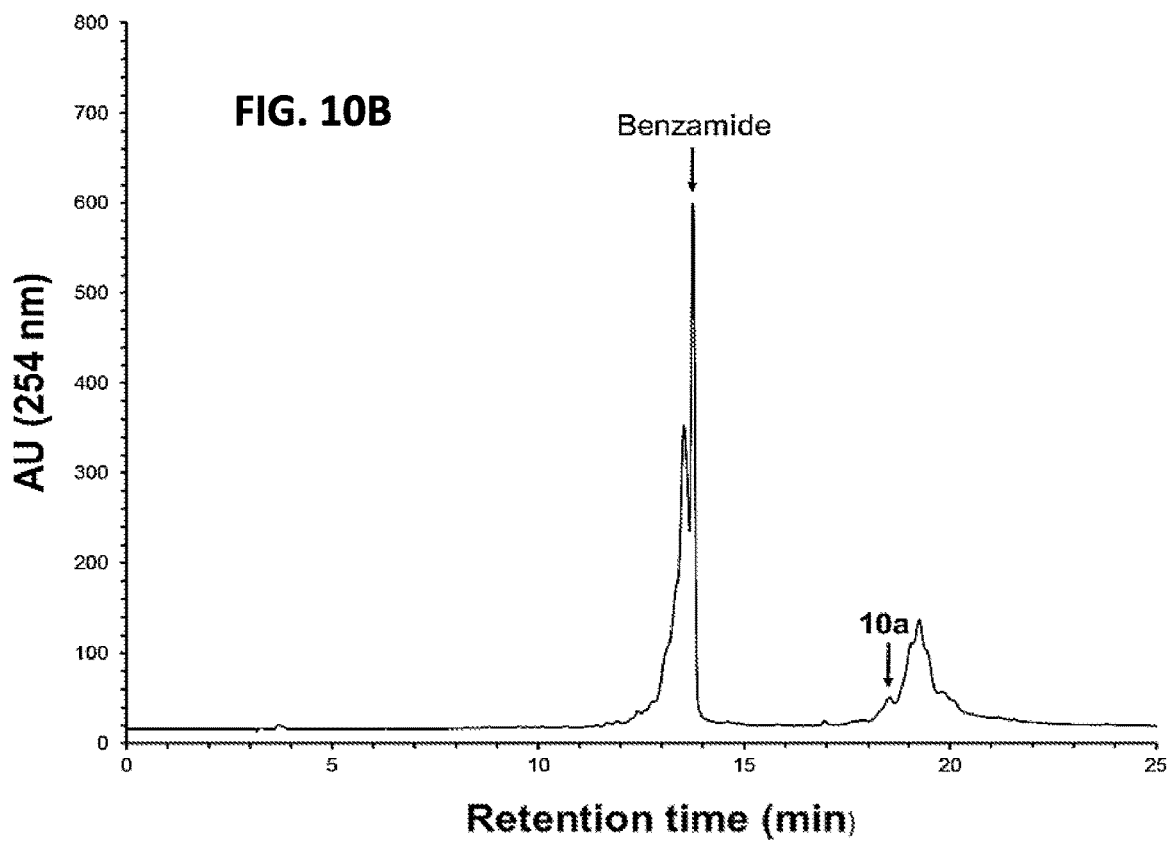
FIG. 10B shows the RP-HPLC profile of remaining unpurified 10a after capture by support 3 on 10-fold scale up.

With the objective of demonstrating that the solid-phase purification process can be qualified as highly parallel and scalable, the solid-phase synthesis of ten identical phosphorothioate DNA sequences (10a) has been carried out, each on a scale of 1 μmole using the conditions described in Example 12. Upon completion of the syntheses, deprotection and release of each sequence from the CPG support, the ammoniacal solution of each sequence is pooled together and rotoevaporated to dryness under low pressure. The amounts of the capture support 3, reagents and solvent required for the capture of 10a have been increased by ten-fold while keeping the final concentration of the reagents the same as reported for individual syntheses. The capture reaction is performed under conditions identical to those described above (Scheme 3) for individual syntheses in terms of reaction time and temperature. An aliquot of the capture reaction has been subjected to RP-HPLC analysis showing, as anticipated, near complete (>98%) disappearance of the DNA sequence 10a within 3 h (FIGS. 10A and 10B). Release of the DNA sequence 12a from the support 11a (see, e.g., FIG. 10C) has been carried out using a 10-fold increase of 1.0 M TBAF/DMSO solution that had been required for a 1 μmol scale reaction while keeping reaction time and temperature conditions the same. A 10-fold increase in the volume of THF is necessary to precipitate 12a. The DNA precipitate was isolated in a yield near proportional to the 1 μmol process scale, thereby conclusively demonstrating that the solid-phase purification of nucleic acid sequences can be achieved in a highly parallel manner and in yields comparable to those obtained from the 1 μmol scale. ESI-MS analysis of the DNA precipitate has revealed a mass consistent with the theoretical molecular weight of the DNA sequence 12a.

The following examples further illustrate the invention but, of course, should not be construed as in any way limiting its scope.

IV. Examples

Materials and Methods.

All reactions sensitive to moisture and/or air are carried out under an atmosphere of argon in dry solvents under anhydrous conditions using oven-dried glassware. Common solvents (acetonitrile, benzene, dichloromethane, chloroform, methanol, 2-propanol, hexane, acetone, ethyl acetate THF, formamide, DMF and DMSO), anhydrous solvents (acetonitrile, dichloromethane, THF, DMF, pyridine and DMSO), deuterated solvents (benzene-$d_6$ and DMSO-$d_6$) and chemicals including 7-oxooctanoic acid, 1,1'-carbonyldiimidazole, 3-aminopropyl silica gel, acetic anhydride, 1-methyl imidazole, O,O'-1,3-propanediylbishydroxylamine dihydrochloride, triethylamine, N,N-diisopropylethylamine, N,N'-dimethylethylenediamine, concentrated (28%) aqueous ammonia, 5,5-dimethyl-dihydro-furan-2-one, imidazole, dichlorodiisopropylsilane, methoxytrimethylsilane, 2-cyanoethyl N,N-diisopropylchlorophosphoramidite, tetra-n-butylammonium chloride, tetra-n-butylammonium fluoride and anhydrous sodium sulfate were all purchased from commercial sources and used without further purification. Ancillary reagents commonly used in solid-phase DNA synthesis including 5'-O- and nucleobase-protected deoxyribonucleosides phosphoramidites, 1H-tetrazole, 3H-1,2-benzodithiol-3-one 1,1-dioxide and succinylated long chain alkylamine controlled-pore glass (CPG) support functionalized with either 2'-deoxythymidine or $N^6$-benzoyl-2'-deoxyadenosine, as the leader nucleoside, were obtained from reputable commercial sources and were dried over fresh $P_2O_5$ in a dessicator under high vacuum prior to use. Reagents for enzymatic hydrolysis of native DNA sequences such as magnesium chloride, Tris.Cl buffer, snake venom phosphodiesterase (*Crotallus adamanteus*) and bacterial alkaline phosphatase (*E. coli*) were all purchased from commercial sources and used as received. Flash chromatography purifications are performed on glass columns (6.0 cm or 2.5 cm I.D.) packed with silica gel 60 (EMD, 230-400 mesh), whereas analytical thin-layer chromatography (TLC) analyses are conducted on 2.5 cm×7.5 cm glass plates coated with a 0.25 mm thick layer of silica gel 60 $F_{254}$ (EMD). Analytical RP-HPLC analyses are performed using a 5 μm Supelcosil LC-18S column (25 cm×4.6 mm) according to the following conditions: starting from 0.1 M triethylammonium acetate pH 7.0, a linear gradient of 2.5% or 5.0% MeCN/min, when indicated, is pumped at a flow rate of 1 mL/min for 40 min. 2 M Triethylammonium acetate buffer was purchased from Applied Biosystem and diluted to 0.1 M with HPLC grade water prior to use. RP-HPLC-purified DNA sequences are desalted using commercial PD-10 (Sephadex G-25M) columns. All NMR experiments are performed using a spectrometer operating at 300.13, 75.47 and 121.5 MHz for one-dimensional $^1H$, $^1H$-decoupled $^{13}C$ and $^1H$-decoupled $^{31}P$, respectively. Samples are maintained at a temperature of 298° K. All spectra are recorded in deuterated solvents or as indicated and chemical shifts δ are reported in parts per million (ppm) relative to appropriate internal references. High resolution mass spectra (HRMS) used to confirm the elemental composition of new compounds were measured on a Bruker Daltonics ApexQ FTICR mass spectrometer equipped with a 12 T magnet. Electrospray ionization in positive ion mode was used to generate $[M+H]^+$ and $[M+Na]^+$ ions out of test samples (0.01 mg dissolved in 1 mL of 10 mM ammonium acetate in MeCN:$H_2O$ (1:1 v/v)). Spectra were externally calibrated using 0.5 mg/mL solution of CsI in water, which yielded a series of peaks in the mass range used for analysis (200-2000 m/z).

Example 1

This example demonstrates a preparation of solid support 2.

To a solution of 7-oxooctanoic acid (1, 0.58 g, 3.0 mmol) in dry THF (4 mL) was added 1,1'-carbonyldiimidazole (CDI, 0.49 g, 3.0 mmol); the solution was stirred for 2 h at 25° C. Commercial 3-aminopropyl silica gel (1.0 g, about 1 mmol NH$_2$) was added to the solution after being washed with 20% triethylamine in MeCN (20 mL), filtered, and dried under argon. The suspension was mechanically shaken at 65° C. for 24 h. After filtration, the solid support was washed successively with THF (20 mL) and MeCN (20 mL). The solid support was then suspended, over a period of 30 min, in a commercial solution (20 mL) of acetic anhydride, 1-methylimidazole and pyridine in THF to inactivate unreacted amine functions. After filtration, the support was washed with MeCN (2×20 mL) and then dried under high vacuum to give the functionalized solid support 2.

Example 2

This example demonstrates a preparation of solid support 3.

Solid support 2 (1.0 g) was placed in a 10 mL-glass vial to which was added a solution of O,O'-1,3-propanediylbishydroxylamine dihydrochloride (537 mg, 3.00 mmol) in H$_2$O (4 mL). The glass vial was sealed and the suspension was mechanically shaken for 16 h at 65° C. The suspension was filtered, washed with DMF (20 mL), MeCN (20 mL) and dried under high vacuum to give the solid support 3, which was stored at −20° C. until needed. The concentration of aminooxy functions covalently attached to 3 was measured by first washing the support (200 mg) with a solution (2 mL) of Et$_3$N in MeCN (1:2 v/v) followed by MeCN (10 mL). The solid support (20 mg) was then added to a solution (300 μL) of 6c (60 mg. 0.1 mmol) in DMSO:H$_2$O (5:1 v/v). The suspension was mechanically agitated at 25° C. over a period of 24 h and filtered. The 4-monomethoxytritylated support was washed with MeCN (3×5 mL) and dried. Treatment of an accurately measured amount of support with and accurate volume of 3% trichloroacetic acid in $CH_2Cl_2$, released the yellow-colored 4-methoxytrityl cation, the absorbance of which was spectrophotometrically measured at 478 nm to provide a surface density of 146±7 μmoles of aminooxy functions per gram of support 3.

Example 3

This example demonstrates a synthesis of linkers which are used for the solid-phase capture of DNA sequences or measuring the concentration of aminooxy functions conjugated to support 3 in accordance with an embodiment of the invention.

4-Hydroxy-N-methyl-N-(2-(methylamino)ethyl)butanamide (5a). N,N'-dimethylethylenediamine (3.25 g, 40.0 mmol) and commercial γ-butyrolactone (4a, 1.72 g, 20.0 mmol) were placed in a 25 mL-glass vial, which was sealed and heated at 90° C. for 16 h. The reaction mixture was then rotoevaporated to an oil under reduced pressure. The oily material was loaded on the top of a glass column packed with silica gel (~40 g) pre-equilibrated in $CHCl_3$:MeOH (9:1 v/v/v). The product was eluted from the column using a gradient of MeOH (10→20%) in $CHCl_3$ to afford 5a (2.32 g, 14.4 mmol) as an oil in a yield of 72%. $^1$H NMR (300 MHz, DMSO-$d_6$): δ 3.39 (dt, J=6.6, 2.0 Hz, 2H), 3.32 (dt, J=6.6, 2.0 Hz, 2H), 2.95 (s, 1.5H), 2.79 (s, 1.5H), 2.59 (t, J=6.6 Hz, 1H), 2.53 (t, J=6.6 Hz, 1H), 2.34 (t, J=7.4 Hz, 1H), 2.29 (t, J=7.4 Hz, 1H), 2.28 (s, 1.5H), 2.25 (s, 1.5H), 1.63 (m, 2H). $^{13}$C NMR (75 MHz, DMSO-$d_6$): δ 171.92, 171.91, 60.3, 49.7, 49.0, 48.9, 46.6, 36.2, 36.0, 35.4, 33.1, 29.3, 28.6, 28.3, 28.0. +ESI-TOF MS: calcd for $C_8H_{18}N_2O_2$ $[M+H]^+$ 175.1400, found 175.1405

4-Hydroxy-N,4-dimethyl-N-(2-(methylamino)ethyl)pentanamide (5b). The preparation of 5b has been performed at the same scale and conditions used for the preparation of 5a with the exception of replacing 4a with commercial 5,5-dimethyl-dihydro-furan-2-one (4b, 2.28 g, 20.0 mmol). The purification of 5b was carried out as described above for 5a and isolated as an oil (2.99 g, 14.8 mmol) in a yield of 74%. $^1$H NMR (300 MHz, DMSO-$d_6$): δ 4.23 (br s, 1H), 3.33 (q, J=6.6 Hz, 2H), 2.97 (s, 1.5H), 2.79 (s, 1.5H), 2.61 (t, J=6.6 Hz, 1H), 2.53 (t, J=6.6 Hz, 1H), 2.37-2.27 (m, 3H), 2.28 (s, 15H), 2.25 (s, 1.5H), 1.57 (m, 2H), 1.08 (s, 3H), 1.07 (s, 3H). $^{13}$C NMR (75 MHz, DMSO-$d_6$): δ 172.5, 172.4, 79.1, 49.7, 49.0, 48.9, 46.6, 38.7, 38.3, 36.2, 35.9, 33.1, 28.9, 28.1, 27.4. +ESI-TOF MS: calcd for $C_{10}H_{22}N_2O_2$ $[M+H]^+$ 203.1754, found 203.1763

N-(2-(4-hydroxy-N-methylbutanamido)ethyl)-N-methyl-7-oxooctanamide (6a). To a solution of 7-oxooctanoic acid (1, 2.45 g, 15.5 mmol) in dry THF (15 mL) was added 1,1'-carbonyldiimidazole (2.52 g, 15.5 mmol). The solution was stirred for 2 h at 25° C. and upon addition of 5a (2.32 g, 14.4 mmol), the reaction mixture was allowed to stir at 65° C. for 24 h. The solution was rotoevaporated under reduced pressure; the material left was dissolved in $CHCl_3$ (40 mL) and vigorously mixed with water (20 mL). The organic phase was collected and rotoevaporated to dryness under low pressure. The crude product was then dissolved in a minimal volume of $CHCl_3$ (4 mL) and loaded on the top of a glass column packed with silica gel (~40 g) pre-equilibrated in $CHCl_3$. The product 6a was eluted from the column using a gradient of MeOH (0→4%) in $CHCl_3$. Pure 6a was isolated as an oil (3.57 g, 11.3 mmol) in a yield of 78%. $^1$H NMR (300 MHz, DMSO-$d_6$): δ 4.44 (t, J=5 Hz, 1H), 3.46 (s, 0.7H), 3.39 (s, 3.5H), 2.97 (s, 0.7H), 2.96 (s, 0.8H), 2.92 (s, 1.1H), 2.91 (s, 1.1H), 2.81 (m, 2.1H), 2.40 (t, J=7.3 Hz, 2H), 2.32-2.15 (m, 4H), 2.07 (s, 3H), 1.62 (m, 2H), 1.45 (m, 4H), 1.22 (m, 2H). $^{13}$C NMR (75 MHz, DMSO-$d_6$): δ 208.5, 172.4, 172.3, 172.2, 172.1, 172.0, 171.9, 171.86, 171.81, 60.3, 60.24, 60.20, 47.3, 46.5, 46.4, 45.8, 45.6, 44.2, 42.6, 35.9, 35.8, 35.1, 33.5, 33.4, 33.12, 33.08, 32.4, 32.3, 31.4, 29.7, 29.3, 29.2, 28.4, 28.3, 28.28, 28.20, 28.0, 27.9, 24.7, 24.6, 24.31, 24.26, 23.1. +ESI-TOF MS: calcd for $C_{16}H_{30}N_2O_4$ $[M+Cs]^+$ 447.1255, found 447.1258.

N-(2-(4-hydroxy-N,4-dimethylpentanamido)ethyl)-N-methyl-7-oxooctanamide (6b) The preparation of 6b has been performed at the same scale and conditions used for the preparation of 6a with the exception of replacing 5a with 5b, (2.91 g, 14.4 mmol). The purification of 6b was carried out as described above for 6a and isolated as an oil (3.97 g, 11.6 mmol) in a yield of 80%. $^1$H NMR (300 MHz, DMSO-$d_6$): δ 4.22 (m, 1H), 3.47 (s, 0.4H), 3.39 (m, 3H), 3.33 (s, 0.4H), 2.98 (s, 0.6H), 2.96 (s, 0.6H), 2.94 (s, 1H), 2.91 (s, 1H), 2.82 (d, J=2.1 Hz, 0.6H), 2.80 (s, 1H), 2.40 (t, J=7.3 Hz, 2H), 2.33-2.21 (m, 3H), 2.17 (t, J=7.3 Hz, 0.8H), 2.06 (s, 3H), 1.56-1.52 (m, 1.8H), 1.50-1.38 (m, 4.2H), 1.22 (m, 2H), 1.08 (s, 1.4H), 1.06 (s, 3.8H). $^{13}$C NMR (75 MHz, DMSO-$d_6$): δ 208.4, 172.9, 172.7, 172.5, 172.4, 172.2, 172.0, 171.8, 171.7, 79.1, 68.25, 68.21, 47.3, 47.2, 46.6, 46.4, 45.8, 45.6, 44.1, 44.0, 42.6, 38.7, 38.2, 36.0, 35.8, 35.1, 35.0, 33.40, 33.37, 33.05, 33.01, 32.4, 32.3, 31.4, 29.6, 29.2, 28.4, 28.3, 28.2, 28.14, 28.06, 27.2, 24.7, 24.6, 24.3, 24.2, 23.1. +ESI-TOF MS: calcd for $C_{18}H_{34}N_2O_4$ $[M+H]^+$ 343.2591, found 343.2623.

N-(2-(4-((4-methoxyphenyl)diphenylmethoxy)-N-methylbutanamido)ethyl)-N-methyl-7-oxooctanamide (6c). To a solution of 6a (628 mg, 2.00 mmol) in dry pyridine was added 4-methoxytrityl chloride (927 mg, 3.00 mmol). The reaction mixture was stirred at 25° C. over a period of 4 h. The reaction was then quenched upon addition of water (5 mL) and subjected to extraction using $CHCl_3$. Upon phase separation the organic phase was collected, dried over anhydrous sodium sulfate and filtered. The filtrate was concentrated under reduced pressure to an oil. The oily material was loaded on the top of a glass column packed with silica gel pre-equilibrated in a solution of $CHCl_3$:$C_5H_5N$ (99.5:0.5 v/v). The reaction product was eluted from the column using a gradient of 0→2% MeOH in $CHCl_3$:$C_5H_5N$ (99.5:0.5 v/v). Fractions containing the product were collected and rotoevaporated to dryness under low pressure. The material left was co-evaporated with toluene (3×5 mL) to remove residual $C_5H_5N$. Pure 6c was isolated as an oil (1.01 g, 1.7 mmol) in a yield of 85%. $^1$H NMR (300 MHz, DMSO-$d_6$): δ 7.39-2.29 (m, 8H), 7.25-7.20 (m, 4H), 6.89 (d, J=8.8 Hz, 2H), 3.74 (s, 3H), 3.42 (s, 0.5H), 3.36 (s, 2H), 2.98 (m, 2H), 2.93 (s, 0.7H), 2.90 (s, 0.8H), 2.88 (s, 1H), 2.87 (s, 1H), 2.79 (m, 2H), 2.35 (m, 3H), 2.26-2.12 (m, 3H), 2.04 (s, 1H), 2.03 (s, 1H), 2.02 (s, 1H), 1.77 (m, 2H), 1.42 (m, 4H), 1.19 (m, 2H). $^{13}$C NMR (75 MHz, DMSO-$d_6$): δ 208.3, 172.1, 172.0, 171.9, 171.7, 171.6, 171.5, 171.4, 158.1, 144.59, 144.57, 135.4, 129.8, 128.8, 128.1, 127.9, 127.8, 126.7, 125.2, 113.1, 85.5, 62.6, 62.5, 62.4, 55.0, 47.3, 47.2, 46.4, 46.3, 45.8, 45.6, 44.13, 44.10, 42.6, 35.9, 35.8, 35.1, 35.0, 33.4, 33.3, 33.0, 32.34, 32.28, 31.4, 29.58, 29.56, 29.3, 29.2, 28.38, 28.35, 28.3, 28.2, 25.4, 25.1, 24.7, 24.5, 24.3, 24.2, 23.1, 21.0. +ESI-TOF MS: calcd for $C_{36}H_{46}N_2O_5$ $[M+Cs]^+$ 719.2456, found 719.2458.

Example 4

This example demonstrates a procedure for the preparation of 5'-functionalized deoxyribonucleosides (8a-d) in accordance with an embodiment of the invention.

To 6b (780 mg, 2.28 mmol) and imidazole (184 mg, 2.70 mmol) in a flame-dried 25 mL-flask, was added under argon, dry DMF (5 mL) and N,N-diisopropylethylamine (2.35 mL, 13.5 mmol); the solution was then cooled to 0° C. Dichlorodiisopropylsilane (730 µL, 4.50 mmol) was added to the solution, which was left stirring for 1 h at 0° C. The reaction mixture was allowed to warm up to room temperature over 4 h and then cooled to −60° C. A solution of deoxyribonucleoside 7a (1.31 g, 5.40 mmol) and imidazole (368 mg, 5.40 mmol) in dry DMF (5 mL) was added dropwise to the reaction mixture, which was kept stirring at −60° C. for 1 h. The reaction was then allowed to warm up to 0° C. and was left stirring for 3 h at the same temperature. The reaction mixture was quenched by the addition of cold (0° C.) 5% aq. NaHCO$_3$ (40 mL) and EtOAc (40 mL); after vigorous shaking, the organic layer was collected and rotoevaporated to dryness under low pressure. The crude product was dissolved in a minimal volume of CHCl$_3$ (4 mL) and loaded on the top of a glass column packed with silica gel (~40 g) pre-equilibrated in CHCl$_3$. The product 8a was eluted from the column using a gradient of MeOH (0→6%) in CHCl$_3$. Pure 8a (1.32 g, 1.59 mmol) was isolated as a solid in a yield of 70%. The 5'-functionalized deoxyribonucleosides 8b-d have been similarly prepared, purified and isolated as oily materials in yields in the range of 50-68%.

8a: $^1$H NMR (300 MHz, DMSO-d$_6$): δ 11.23 (s, 1H), 8.74 (s, 1H), 8.62 (s, 0.7H), 8.59 (s, 0.3H), 8.32 (s, 1H), 8.07 (d, J=7.8 Hz, 2H), 7.65 (dd, J=7.6, 7.4 Hz, 1H), 7.56 (dd, J=7.6, 7.4 Hz, 2H), 6.51 (t, J=6.8 Hz, 1H), 5.45 (m, 1H), 4.54 (bs, 1H), 3.98 (m, 2H), 3.85 (m, 1H), 3.38 (m, 4H), 2.92 (m, 4H), 2.79 (m, 2H), 2.38 (t, J=7.3 Hz, 2H), 2.31-2.13 (m, 4H), 2.05 (s, 3H), 1.66 (m, 2H), 1.43 (m, 4H), 1.21 (m, 7H), 0.97 (m, 16H). $^{13}$C NMR (75 MHz, DMSO-d$_6$): δ 208.3, 172.4, 172.2, 172.1, 172.0, 171.9, 171.8, 171.71, 171.66, 165.6, 151.9, 151.4, 150.3, 143.0, 142.8, 133.4, 132.4, 128.5, 128.4, 125.9, 125.8, 87.2, 83.74, 83.66, 79.2, 73.2, 73.1, 70.1, 70.4, 68.3, 68.2, 62.9, 62.7, 47.2, 46.5, 45.8, 45.7, 44.1, 44.0, 42.6, 38.5, 35.9, 35.8, 35.0, 33.5, 33.3, 33.2, 33.0, 32.4, 32.3, 31.5, 29.6, 29.3, 29.2, 28.4, 28.3, 28.2, 28.1, 28.0, 27.3, 27.1, 24.7, 24.6, 24.3, 24.2, 23.1, 17.60, 17.52, 17.47, 17.43, 17.3, 17.21, 17.18, 17.11, 17.0, 12.9, 12.7, 12.6, 12.32, 12.29. +ESI-HRMS: calcd for C$_{41}$H$_{63}$N$_7$O$_8$Si [M+Na]$^+$832.4399, found 832.4411.

8b: $^1$H NMR (300 MHz, DMSO-d$_6$): δ 11.25 (s, 1H), 8.27 (d, J=7.3 Hz, 1H), 8.01 (d, J=7.3 Hz, 2H), 7.63 (m, 1H), 7.52 (m, 2H), 7.37 (d, J=7.3 Hz, 1H), 6.16 (t, J=6.2 Hz, 1H), 5.37 (d, J=4.4 Hz, 1H), 4.28 (m, 1H), 4.01-3.89 (m, 3H), 3.47 (s, 0.4H), 3.38 (m, 3H), 2.98 (s, 0.7H), 2.95 (s, 0.7H), 2.94 (s, 1.1H), 2.90 (s, 1.1H), 2.81 (m, 2H), 2.38 (m, 5H), 2.23 (t, J=7.3 Hz, 2H), 2.15 (m, 2H), 2.05 (s, 3H), 1.70 (m, 2H), 1.43 (m, 4H), 1.27 (s, 6H), 1.20 (m, 2H), 1.02 (m, 14H). $^{13}$C NMR (75 MHz, DMSO-d$_6$): δ 208.29, 208, 27, 172.4, 172.2, 172.0, 171.9, 171.8, 171.70, 171.66, 167.3, 163.0, 154.3, 144.3, 133.1, 132.7, 128.41, 128.38, 95.8, 87.1, 86.0, 73.34, 73.30, 69.3, 62.3, 47.3 47.2, 46.5, 46.4, 45.8, 45.7, 44.1, 44.0, 42.6, 40.8, 35.9, 35.8, 35.1, 35.0, 33.5, 33.3, 33.2, 33.0, 32.4, 32.3, 31.5, 29.6, 29.39, 29.37, 28.4, 28.3, 28.2, 28.13, 28.07, 27.3, 27.1, 24.7, 24.6, 24.31, 24.25, 23.1, 17.61, 17.59, 17.51, 17.48, 12.8, 12.6. +ESI-HRMS: calcd for C$_{40}$H$_{63}$N$_5$O$_9$Si [M+Na]$^+$808.4287, found 808.4298.

8c: $^1$H NMR (300 MHz, DMSO-d$_6$): δ 12.07 (s, 1H), 11.68 (s, 1H), 8.16 (s, 1H), 6.22 (t, J=6.6 Hz, 1H), 5.37 (d, J=4.2 Hz, 1H), 4.42 (m, 1H), 3.88 (d, J=7.8 Hz, 1H), 3.83 (m, 2H), 3.44-3.34 (m, 4H), 2.95 (s, 0.8H), 2.94 (s, 0.8H), 2.91 (s, 1.2H), 2.89 (s, 1.2H), 2.77 (m, 3H), 2.63 (m, 2H), 2.38 (t, J=7.3 Hz, 2H), 2.33-2.13 (m, 5H), 2.05 (s, 3H), 1.66 (m, 2H), 1.43 (m, 4H), 1.21 (m, 7H), 1.12 (d, J=6.8 Hz, 6H), 0.95 (m, 14H). $^{13}$C NMR (75 MHz, DMSO-d$_6$): δ 208.3, 180.1, 172.4, 172.2, 172.1, 172.0, 171.9, 171.8, 171.69, 171.66, 154.8, 148.3, 148.0, 137.2, 128.3, 120.3, 87.1, 82.8, 73.2, 73.1, 70.0, 62.9, 47.3, 47.2, 46.5, 46.3, 45.7, 45.6, 44.1, 44.0, 42.6, 35.9, 35.8, 35.05, 35.02, 34.7, 33.5, 33.3, 33.2, 33.0, 32.4, 32.3, 31.4, 29.6, 29.3, 28.4, 28.3, 28.2, 28.1, 28.0, 27.2, 27.1, 24.7, 24.5, 24.3, 24.2, 23.1, 18.83, 18.78, 17.55, 17.52, 17.48, 17.43, 17.1, 12.7, 12.6. +ESI-HRMS: calcd for C$_{38}$H$_{65}$N$_7$O$_9$Si [M+Na]$^+$814.4505, found 814.4518.

8d: $^1$H NMR (300 MHz, DMSO-d$_6$): δ 11.33 (s, 1H), 7.42 (s, 1H), 6.17 (t, J=6.8 Hz, 1H), 5.31 (d, J=4.5 Hz, 1H), 4.25 (m, 1H), 3.85 (m, 3H), 3.46 (s, 0.4H), 3.39 (s, 2H), 3.36 (m, 1.1H), 2.97 (s, 0.8H), 2.95 (s, 0.7H), 2.92 (s, 1H), 2.90 (s, 1H), 2.80 (m, 2H), 2.39 (t, J=7.3 Hz, 2H), 2.13 (m, 1H), 2.22 (m, 2H), 2.12 (m, 3H), 2.06 (s, 3H), 1.76 (s, 3H), 1.67 (m, 2H), 1.44 (m, 4H), 1.21 (m, 8H), 1.00 (m, 13H), 0.95 (s, 1H), 0.93 (s, 1H). $^{13}$C NMR (75 MHz, DMSO-d$_6$): δ 208.3, 172.4, 172.2, 172.0, 171.9, 171.8, 171.71, 171.67, 163.1, 150.3, 135.6, 109.4, 86.5, 83.6, 73.3, 73.2, 70.0, 62.8, 47.3, 47.2, 46.5, 46.4, 45.8, 45.7, 44.1, 44.0, 42.6, 35.9, 35.8, 35.1, 35.0, 33.5, 33.3, 33.1, 33.0, 32.4, 32.3, 31.5, 29.6, 29.4, 28.4, 28.3, 28.2, 28.1, 28.0, 27.3, 27.1, 24.7, 24.6, 24.3, 24.2, 23.1, 17.60, 17.56, 17.50, 17.48, 17.3, 12.8, 12.63, 12.59, 12.7. +ESI-HRMS: calcd for C$_{34}$H$_{60}$N$_4$O$_9$Si [M+Na]$^+$719.4022, found 719.4031.

Example 5

This example demonstrates a general procedure for the preparation of nucleoside phosphoramidites (9a-d) in accordance with an embodiment of the invention.

A solution of 8a (897 mg, 1.00 mmol) in CH$_2$Cl$_2$ (10 mL) was placed in a flame-dried 100 mL round-bottom flask. N,N-Diisopropylethylamine (536 µl, 3.00 mmol) was added to the solution and followed by 2-cyanoethyl N,N-diisopropylchlorophosphoramidite (335 µL, 1.50 mmol). The reaction mixture was stirred at 25° C. for 3 h, quenched by the addition of H$_2$O (10 mL) and diluted with CH$_2$Cl$_2$ (25 mL). After vigorous shaking, the organic layer was collected, dried over anhydrous Na$_2$SO$_4$ and rotoevaporated under reduced pressure to afford an oil. The oily material was evenly spread on the top of a column packed with silica gel (~25 g) pre-equilibrated in benzene:Et$_3$N (9:1 v/v). The product was eluted from the column using benzene:Et$_3$N (9:1 v/v) as the eluent. Fractions containing the product were pooled together, concentrated under reduced pressure and dissolved in dry benzene (7 mL). The solution was frozen and then lyophilized under high vacuum to afford triethylamine-free 9a (750 mg, 0.83 mmol) as a colorless oil in 83% yield. The 5'-functionalized deoxyribonucleoside phosphoramidites 9b-d have been similarly prepared and purified. Triethylamine-free 9b-d have been isolated as colorless oils, the yields of which are in the range of 75-80%.

9a: $^{31}$P NMR (121 MHz, C$_6$D$_6$) δ 149.0, 148.8, 148.76, 148.72. +ESI-HRMS: calcd for C$_{50}$H$_{80}$N$_9$O$_9$PSi [M+H]$^+$ 1010.5659, found 1010.5675.

9b: $^{31}$P NMR (121 MHz, C$_6$D$_6$) δ 148.3, 148.25, 148.22, 148.1, 147.91, 147.89. +ESI-HRMS: calcd for C$_{49}$H$_{80}$N$_7$O$_{10}$PSi [M+H]$^+$ 986.5546, found 986.5548.

9c: $^{31}$P NMR (121 MHz, C$_6$D$_6$) δ 148.77, 148.73, 148.0, 147.92, 147.88. +ESI-HRMS: calcd for C$_{47}$H$_{82}$N$_9$O$_{10}$PSi [M+H]$^+$ 992.5764, found 992.5773.

9d: $^{31}$P NMR (121 MHz, C$_6$D$_6$) δ 148.7, 148.6, 148.49, 148.46, 148.37. +ESI-HRMS: calcd for C$_{43}$H$_{77}$N$_6$O$_{10}$PSi [M+Cs]$^+$ 1029.4257, found 1029.4266.

Example 6

This example demonstrates a solid-phase synthesis and deprotection of the DNA sequences 10a-f in accordance with an embodiment of the invention.

Solid-phase synthesis of the phosphorothioate DNA sequences 10a [5'-d($A_{PS}C_{PS}A_{PS}C_{PS}T_{PS}G_{PS}T_{PS}G_{PS}A_{PS}$ $A_{PS}T_{PS}C_{PS}G_{PS}A_{PS}T_{PS}G_{PS}C_{PS}C_{PS}A_{PS}T$)] (SEQ ID NO. 1), 10b [5'-d($C_{PS}T_{PS}C_{PS}C_{PS}G_{PS}T_{PS}A_{PS}C_{PS}C_{PS}T_{PS}T_{PS}A_{PS}C_{PS}$ $G_{PS}T_{PS}C_{PS}T_{PS}T_{PS}G_{PS}T$)] (SEQ ID NO. 2), 10c [5'-d($G_{PS}$ $T_{PS}G_{PS}A_{PS}G_{PS}T_{PS}A_{PS}G_{PS}C_{PS}G_{PS}A_{PS}A_{PS}C_{PS}G_{PS}T_{PS}$ $G_{PS}A_{PS}A_{PS}G_{PS}T$)] (SEQ ID NO. 3), 10d [5'-d($T_{PS}A_{PS}$ $T_{PS}C_{PS}C_{PS}G_{PS}T_{PS}A_{PS}G_{PS}C_{PS}T_{PS}A_{PS}A_{PS}C_{PS}G_{PS}T_{PS}C_{PS}$ $A_{PS}G_{PS}T$)] (SEQ ID NO. 4), 10e [5'-d($A_pC_pA_pC_pT_pG_p$ $T_pG_pA_pA_pT_pC_pG_pA_pT_pG_pC_pC_pA_{PT}$)] (SEQ ID NO. 5) and 10f [5'-d($T_dT_pC_pA_pC_pT_pG_pT_pG_pA_pA_pT_pC_pG_pA_p$ $T_pG_pC_pA_pA_pT_pG_pC_pC_pT_pG_pT_pG_pA_pA_pT_pC_pG_pA_pT_p$ $C_pC_pA_pT_p$ $C_pA_pC_pT_pG_pT_pG_pA_pA_pT_pC_pG_pA_pT_pG_pC_p$ $C_pA_pT$)](SEQ ID NO. 6) was conducted on a scale of 1 μmole using a succinyl long chain alkylamine controlled-pore glass (500 Å LCAA-CPG) or (2000 Å LCAA-CPG for 10f) support functionalized with 5'-O-(4,4'-dimethoxytrityl)-2'-deoxythymidine as the leader nucleoside. The syntheses have been carried out using a DNA/RNA synthesizer and commercial 5'-O-(4,4'-dimethoxytrityl)-$dA^{Bz}$, -$dG^{iBu}$, -$dC^{Bz}$, -dT phosphoramidite monomers, which have been each dissolved in dry MeCN to give a 0.1 M solution. The modified deoxyribonucleoside phosphoramidites 9a-d have also been dissolved in dry MeCN to each provide a 0.15 M solution. Each solution was placed in a vial connected to the DNA/RNA synthesizer through an additional delivery port. Commercial 1H-tetrazole solution was used for phosphoramidite activation in the solid-phase synthesis of 10a-f. The reaction times of the coupling, capping and oxidation steps in the synthesis of the native and phosphorothioate DNA sequences were 120 s, 60 s and 60 s, respectively. It should however be noted that the capping step in the synthesis of the phosphorothioate DNA, sequence was performed after the oxidative sulfuration step, which was effected using 0.05 M 3H-1,2-benzodithiol-3-one 1,1-dioxide in MeCN; the standard 0.02 M iodine solution in THF/pyridine/water is employed in the oxidation step of native DNA sequences. The last coupling reaction of each synthesis was performed using any of the activated deoxyribonucleoside phosphoramidites 9a-d over a period of 180 s. The LCAA-CPG-linked DNA sequence was then transferred to a 4-mL glass vial to which was added concentrated aqueous ammonia (1 mL). The tightly-capped glass vial was placed in a heat block and kept at 65° C. for 16 h. The ammoniacal solution was transferred to another 4-mL glass vial and evaporated to half its original volume using a stream of air.

Example 7

This example demonstrates a solid-phase capture of DNA sequences in accordance with an embodiment of the invention.

Figure 4A:
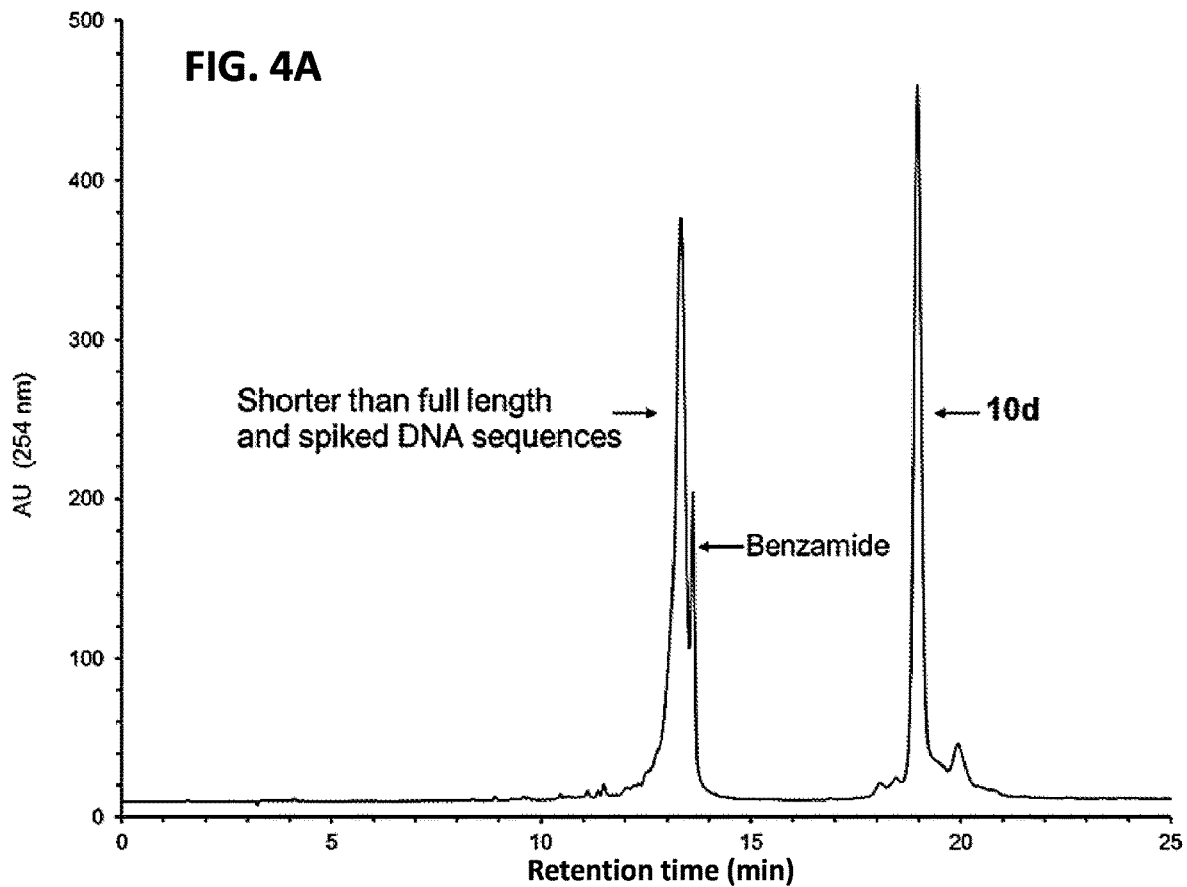
FIG. 4A shows the RP-HPLC profile of unpurified 10d (5'-functionalized 12d) spiked with a 14-, 16- and a 18-mer phosphorothioate DNA sequence, the ratio of 10d:14-mer: 16-mer:18-mer being 5:1:1:1.
Figure 4B:
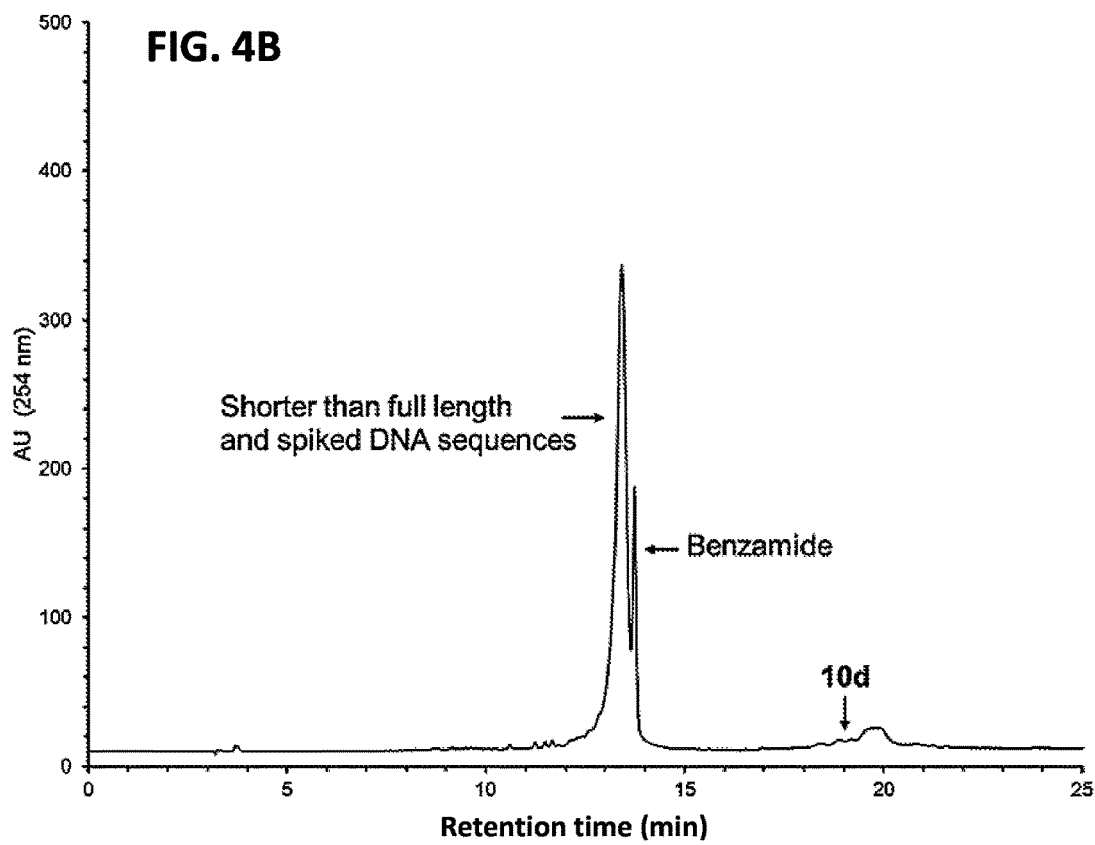
FIG. 4B shows the RP-HPLC profile of 10d that has been captured by the support 3.
Figure 5C:
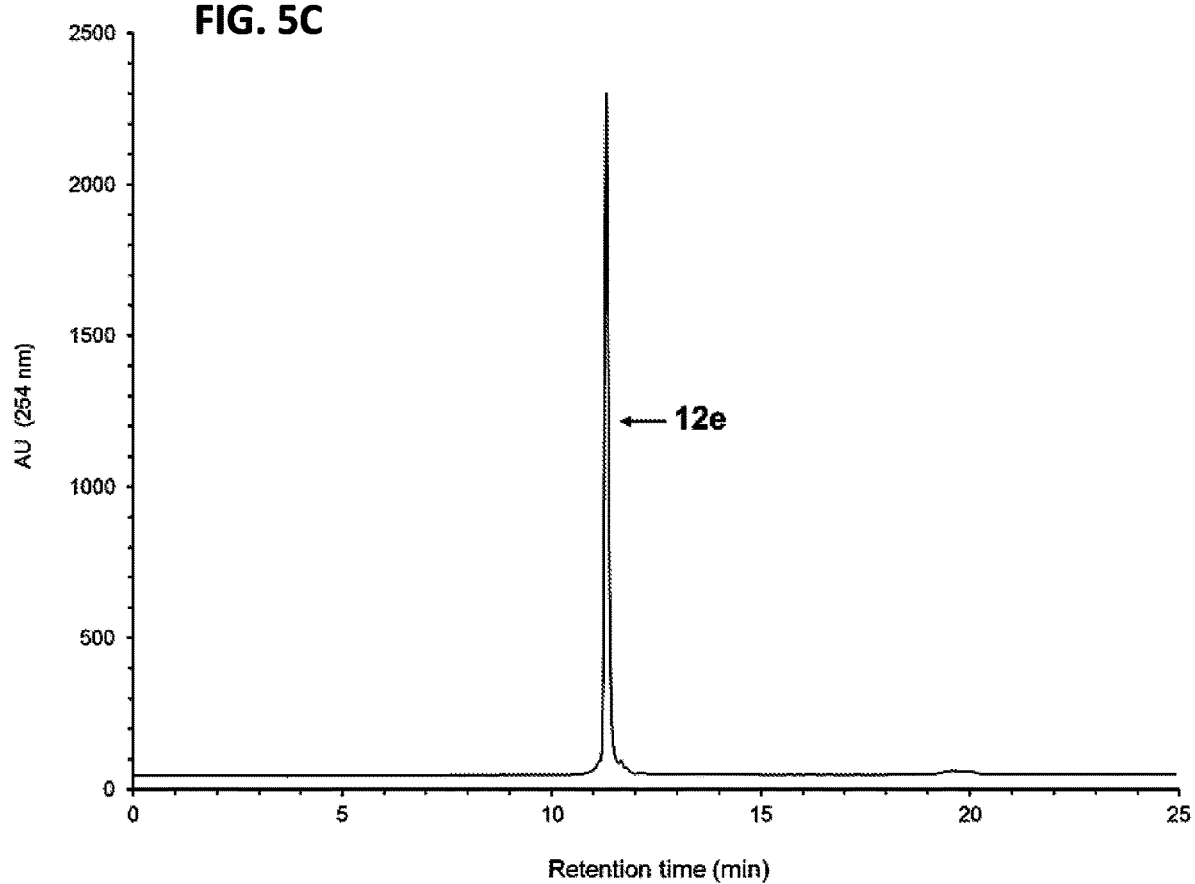
FIG. 5C shows the RP-HPLC analysis of solid-phase purified 12e that has been released from the support 11e.
Figure 5D:
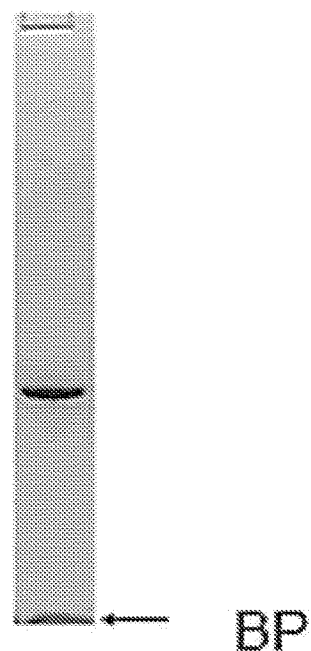
FIG. 5D shows the purity analysis of the solid-phase purified 12e by PAGE.
Figure 6A:
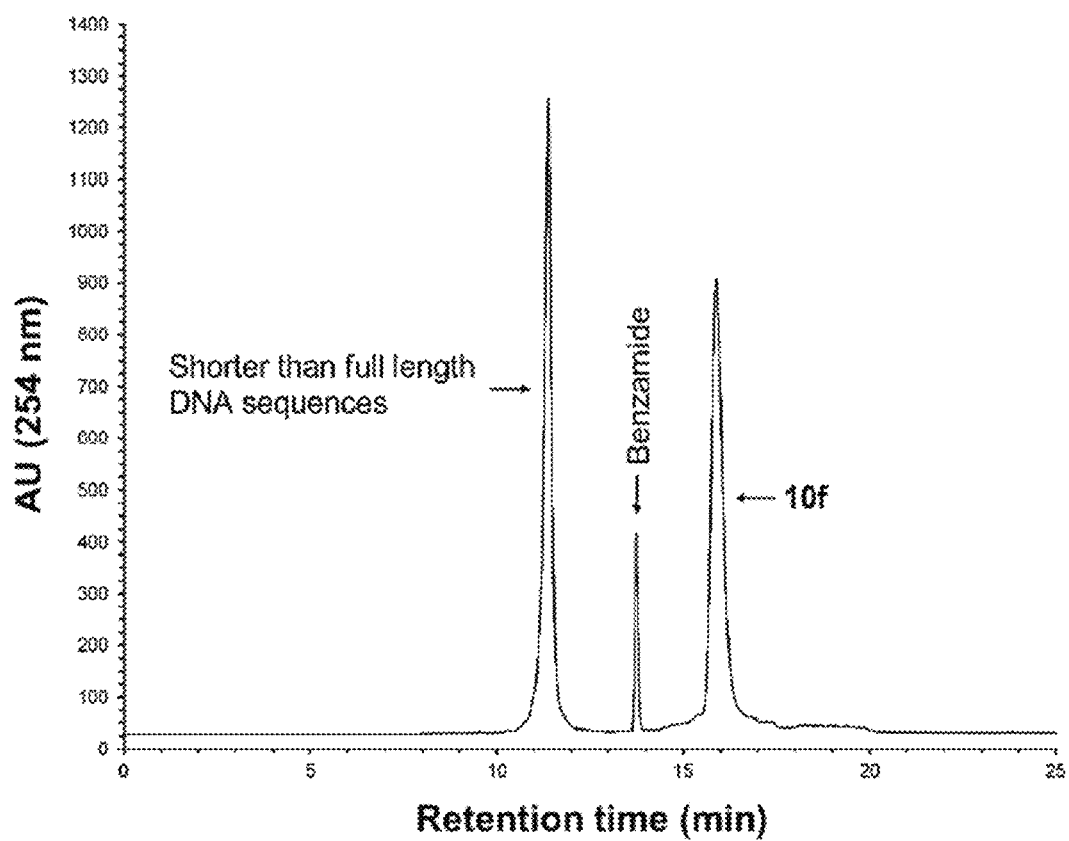
FIG. 6A shows the RP-HPLC profile of unpurified 10f (5'-functionalized 12f).
Figure 6B:
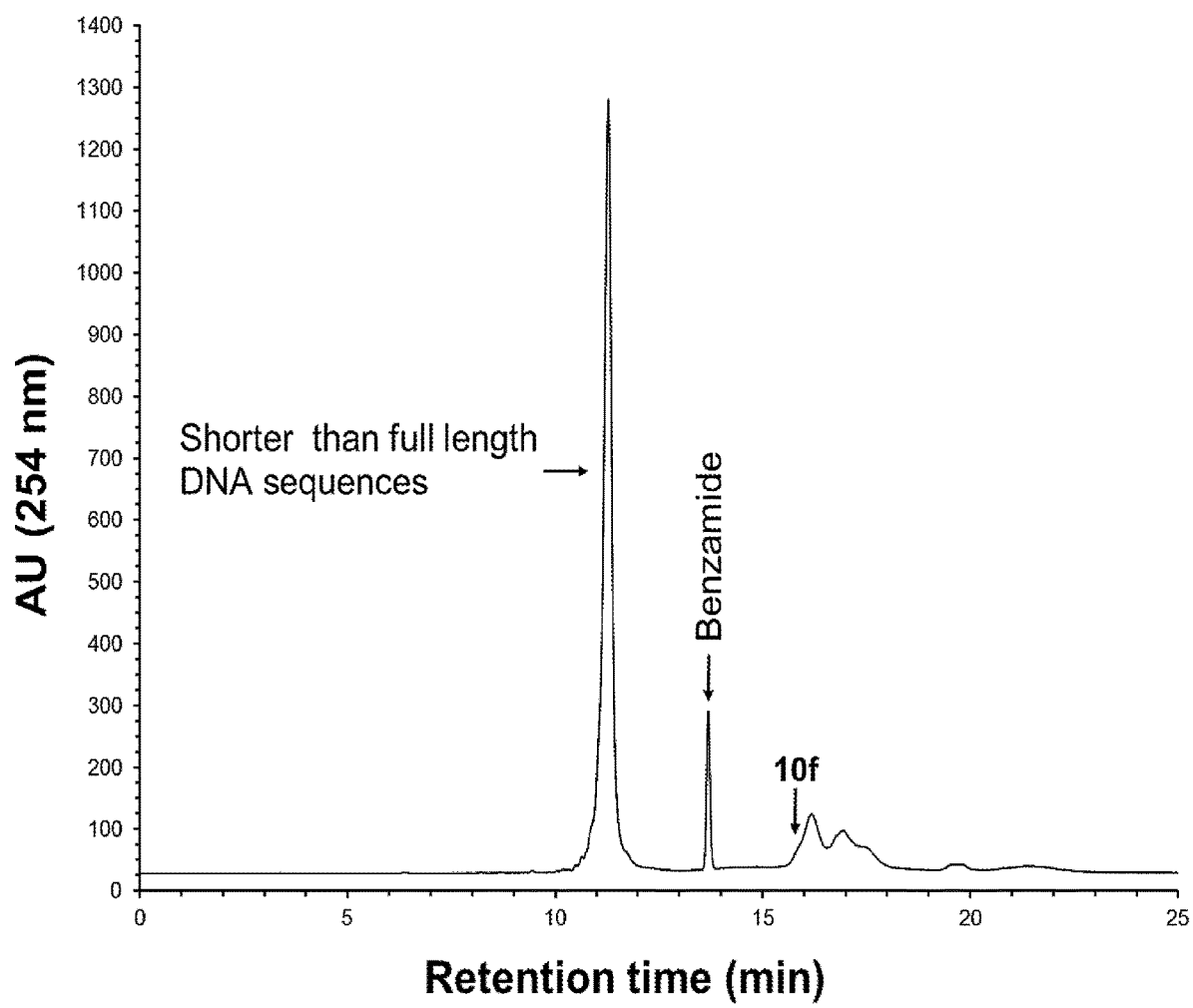
FIG. 6B shows the RP-HPLC profile of unpurified 10f after capture by the support 3.
Figure 6C:
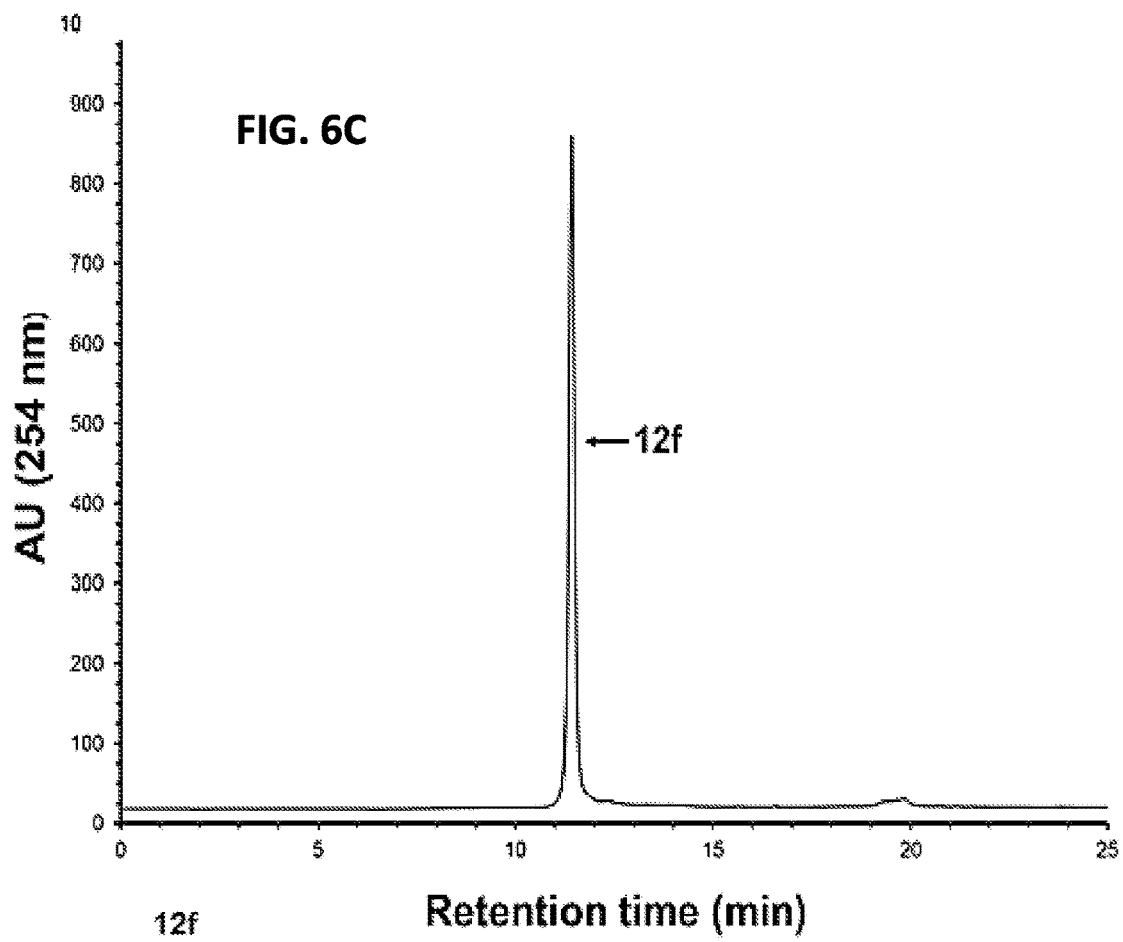
Figure 6D:
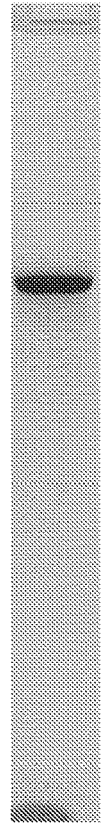
FIG. 6D shows the purity analysis of the solid-phase purified 12f by PAGE.

The aminooximated solid support 3 (150 mg) was washed with 20% triethylamine in MeCN (1 mL), filtered, blow dried under argon and placed into a 1-mL glass vial. The above solution of unpurified 5'-modified phosphorothioate or native DNA sequence 10a or 10e (~500 μL) was added to the glass vial along with tetra-n-butylammonium chloride (14 mg, 50 μmol); the solid-phase capture of the DNA sequence 10a or 10e was carried out over a period of 3 h at 65° C. Near complete capture was achieved upon oximation of the DNA sequence mediated by support 3 to produce the silica gel support 11a or 11e. RP-HPLC analysis of the capture reaction mixture confirmed the near absence of the DNA sequence 10a or 10e (See FIG. 1B or FIG. 5B). Solid-phase capture of the DNA sequences 10b-d and 10f was performed as described for 10a. RP-HPLC analysis of the capture reaction mixtures also confirmed the near absence of the DNA sequences 10b-d and 10f (see FIGS. 2B, 3B, 4B, and 6B) thereby indicating near complete oximation of those sequences by the support 3. FIG. 4A shows the RP-HPLC profile of unpurified 10d (5'-functionalized 12d) spiked with a 14-, 16- and a 18-mer phosphorothioate DNA sequence. FIG. 4B shows the RP-HPLC profile of the phosphorothioate DNA sequence 10d after capture by the support 3. FIG. 4C shows the RP-HPLC analysis of solid-phase purified 12d that has been released from the support 11d. FIG. 4D (middle lane) shows the purity analysis of the solid-phase purified 12d by PAGE. FIGS. 1A, 2A, 3A, 5A, and 6A show the RP-HPLC profiles of unpurified 10a, 10b, 10c, 10e, and 10f (5'-functionalized 12a, 12b, 12c, 12e, and 12f), respectively. FIGS. 1B, 2B, 3B, 5B, and 6B show the RP-HPLC profiles of remaining unpurified 10a, 10b, 10c, 10e, and 10f, respectively, after capture by support 3. FIGS. 1C, 2C, 3C, 5C, and 6C show the RP-HPLC analysis of solid-phase purified 12a, 12b, 12c, 12e, and 12f, that have been released from the supports 11a, 11b, 11c, 11e, and 11f respectively.

FIGS. 1D, 2D, 3D, 5D, and 6D show the purity analysis of the solid-phase purified 12a, 12b, 12c, 12e, and 12f, respectively, by PAGE.

Example 8

This example demonstrates a release of the DNA sequences from the supports 11a-f in accordance with an embodiment of the invention.

The support 11a-f was placed in a 4 mL-screw-capped glass vial to which is added a solution of concd. Aq. $NH_3$:MeCN (1:1 v/v) (1 mL); the glass vial was heated at 65° C. for 30 min and then subjected to filtration. This wash step was repeated once more under identical conditions and is followed by five DMSO washes (1-mL each). Release of the purified DNA sequence from 11a-f was effected by treatment with 1.0 M TBAF in dry DMSO (0.5 mL) in a sealed glass vial kept at 65° C. over a period of 3 h. Methoxytrimethylsilane (200 μL) and MeCN (200 μL) were added to the suspension, which was kept at 25° C. for 30 min and was then filtered through a sintered glass funnel; the filtrate was collected. The solid support was suspended in a solution of concentrated aqueous $NH_3$:MeCN (1:1 v/v) (1 mL) and heated at 65° C. for 30 min and filtered again through a glass-sintered funnel; the filtrate was collected and combined with the previous filtrate. The process was repeated once more under identical conditions. All collected filtrates were pooled together and concentrated under vacuum to approximately 100 μL. THF (1 mL) was added to the concentrated solution in order to precipitate the DNA sequence 12a-f. The precipitate was centrifuged at 14,000×g for 15 min at 25° C.; the supernatant is then carefully removed by suction. The DNA pellet was washed with THF (3×1 mL). The pure DNA sequence 12a-f was dried under reduced pressure and stored at −20° C. until further use. The DNA sequence 12a-f has been characterized by mass spectrometry and its purity by both RP-HPLC and PAGE.

12a:
(SEQ ID NO. 7)
5'-d
$(A_{PS}C_{PS}A_{PS}C_{PS}T_{PS}G_{PS}T_{PS}G_{PS}A_{PS}A_{PS}T_{PS}C_{PS}G_{PS}A_{PS}T_{PS}G_{PS}C_{PS}C_{PS}A_{PS}$
T). -ESI-MS: Calcd. 6406, found, 6407.

12b:
(SEQ ID NO. 8)
5'-d$(C_{PS}T_{PS}C_{PS}C_{PS}G_{PS}T_{PS}A_{PS}C_{PS}C_{PS}T_{PS}T_{PS}A_{PS}C_{PS}G_{PS}T_{PS}C_{PS}T_{PS}T_{PS}G_{P}$
$_{S}$T). -ESI-MS: Calcd. 6315, found, 6315.

12c:
(SEQ ID NO. 9)
5'-d
$(G_{PS}T_{PS}G_{PS}A_{PS}G_{PS}T_{PS}A_{PS}G_{PS}C_{PS}G_{PS}A_{PS}A_{PS}C_{PS}G_{PS}T_{PS}G_{PS}A_{PS}A_{PS}G_{PS}$
T). -ESI-MS: Calcd. 6551, found, 6551.

12d:
(SEQ ID NO. 10)
5'd$(T_{PS}A_{PS}T_{PS}C_{PS}C_{PS}G_{PS}T_{PS}A_{PS}G_{PS}C_{PS}T_{PS}A_{PS}A_{PS}C_{PS}G_{PS}T_{PS}C_{PS}A_{PS}G_{PS}$
T). -ESI-MS: Calcd. 6397, found, 6397.

12e:
(SEQ ID NO. 12)
5'-d$(A_{P}C_{P}A_{P}C_{P}T_{P}G_{P}T_{P}G_{P}A_{P}A_{P}T_{P}C_{P}G_{P}A_{P}T_{P}G_{P}C_{P}C_{P}A_{P}T)$.
-ESI-MS: Calcd. 6101, found, 6101.

Example 9

This example demonstrates a PAGE analysis of the solid-phase purified DNA sequences 12a-f in accordance with an embodiment of the invention.

An aqueous solution (0.25 $OD_{260}$) of each solid-phase purified phosphorothioate and native DNA sequences in a 1.5-mL microcentrifuge tube, was evaporated to dryness under reduced pressure. To each tube was added 10 μL of loading buffer [10× Tris borate EDTA buffer (TBE), pH 8.3, in formamide 1:4 (v/v) containing 2 mg/mL bromphenol blue]. The solution was then vigorously vortexed, centrifuged and loaded into a 2-cm-wide well of a 20×40 cm, 7 M urea/20% polyacrylamide gel (12a-e) or 7 M urea/18% polyacrylamide gel (12f). Electrophoresis was performed at 375 V using 1×TBE buffer pH 8.3 as an electrolyte until the bromphenol blue dye traveled ~80% the length of the gel. The electrophoresis apparatus was dismantled and the gel immersed in 250 mL of a solution composed of i-PrOH:$H_2O$:formamide (2:8:0.4 v/v/v) to which was added a 1 mg/mL Stains-All solution (10 mL) in formamide. The gel was agitated for 3-4 h in the dark whereupon the staining solution was discarded and the gel washed with distilled water (3×250 mL). The gel was then exposed to natural light until disappearance of the purple background and scanned. The DNA sequences appeared as blue (12e-f) or purple bands (12a-d) against a white background.

Example 10

This example demonstrates an enzymatic hydrolysis of the native DNA sequences 12e-f in accordance with an embodiment of the invention.

Figure 7A:
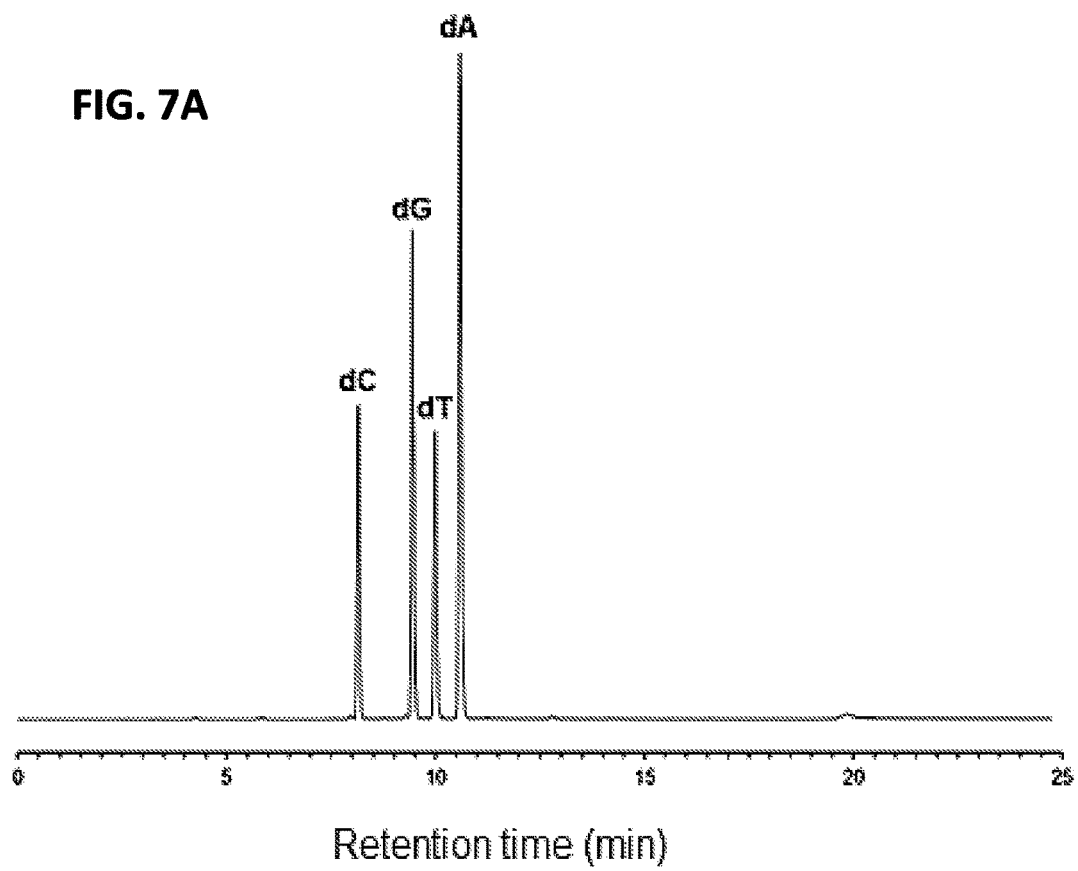
FIGS. 7A and 7B show the RP-HPLC analysis of the enzymatic hydrolysis of fully deprotected, solid-phase purified DNA sequence 12e and 12f, respectively, catalyzed by snake-venom phosphodiesterase (*Crotallus adamanteus*) and bacterial alkaline phosphatase (*Escherichia coli*).
Figure 7B:
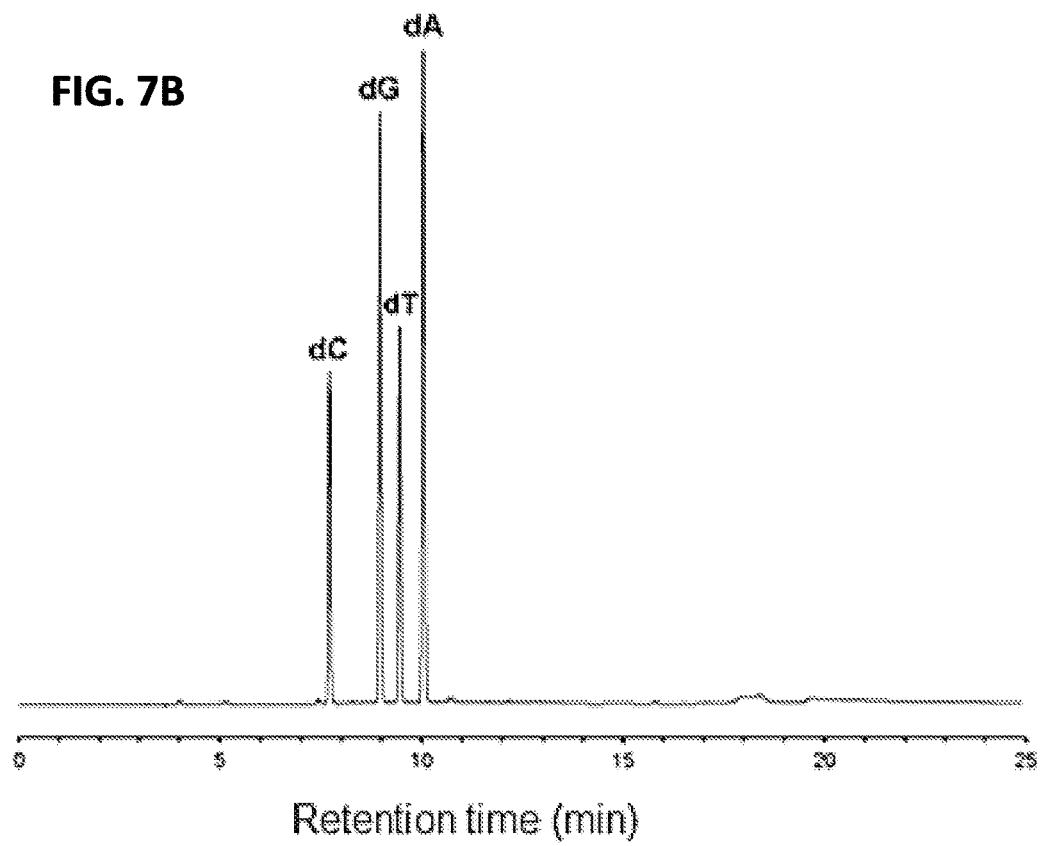

One OD260 unit of an aqueous solution of the solid-phase purified and desalted native DNA sequence 12e or 12f was pipetted into a microcentrifuge tube. The DNA solution was evaporated to dryness under reduced pressure whereupon 1.0 M Tris.Cl buffer pH 9.0 (6 μL), 1.0 M $MgCl_2$ (8 μL) and water (75 μL) are added followed by, after mixing, snake venom phosphodiesterase (*Crotallus adamanteus*, 0.015 U, 5 μL) and bacterial alkaline phosphatase (*E. Coli*, 0.7 U, 6 μL). The enzymatic reactions were allowed to proceed at 37° C. for 16 h. Deactivation of the enzymes was carried out by heating the digest at 90° C. for 3 min. The digest was centrifuged at 14,000×g for 5 min at 25° C. Immediately after centrifugation, an aliquot (50 μL) of the digest was analyzed by RP-HPLC using a 5 μm Supelcosil LC-18S column (25 cm×4.6 mm) according to the following conditions: starting from 0.1 M triethylammonium acetate pH 7.0, a linear gradient of 2.5% MeCN/min was pumped at a flow rate of 1 mL/min for 40 min. RP-HPLC chromatograms of the digests of 12e and 12f are shown in FIGS. 7A and 7B, respectively.

Example 11

This example demonstrates a determination of the efficiency of the solid-phase purification process in accordance with an embodiment of the invention.

To a RP-HPLC-purified and desalted DNA sequence (10a, 70 $OD_{260}$) in a 1-mL glass vial was added a 0.1 M solution of tetra-n-butylammonium chloride in $H_2O$ (150 μL) and support 3 (70 mg). The suspension was processed as described above (Examples 7 and 8) for the solid-phase purification of unpurified 10a to give 12a after release from the solid-support 11a and precipitation in THF. The efficiency of the solid-phase purification process was determined from the following equation: ($OD_{260}$ of the DNA sequence 12a recovered after the solid-phase purification process÷$OD_{260}$ of the DNA sequence 10a before solid-phase purification)×100, that is (63 $OD_{260}$÷70 $OD_{260}$)100=90%.

Example 12

This example demonstrates a ten-fold scale up of the solid-phase purification of the phosphorothioate DNA sequence 12a in accordance with an embodiment of the invention.

Figure 10C:
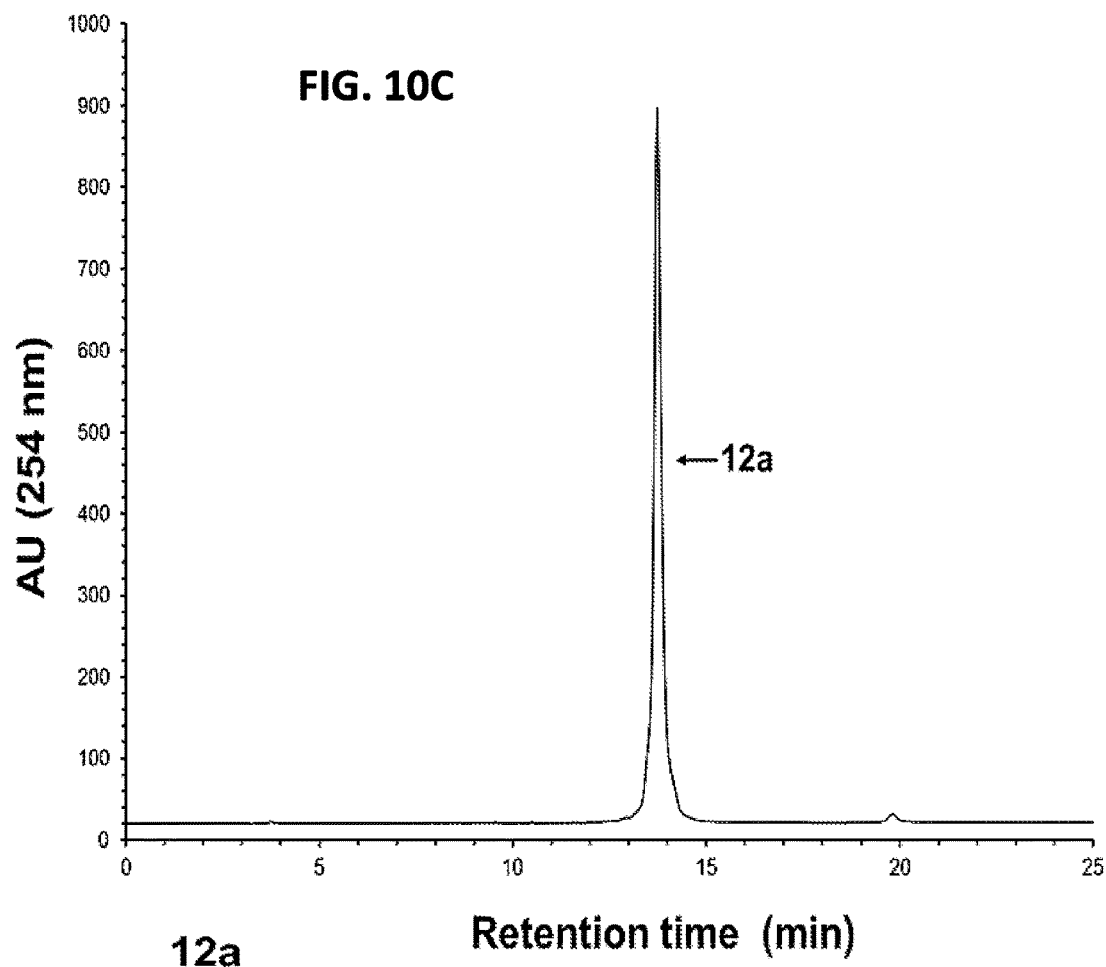
FIG. 10C shows the RP-HPLC analysis of solid-phase purified 12a that has been released from the support 11a on 10-fold scale up.

Ten individual solid-phase syntheses of the phosphorothioate DNA sequence 10a were each conducted on a scale of 1 μmole under conditions identical as those described above for the DNA sequences 10a-d (Example 6). Upon completion of the syntheses, each individual DNA sequence was subjected to a standard deprotection and release from the CPG support protocol under basic conditions. Upon complete deprotection and release of each DNA sequence from the CPG support, the individual ammoniacal solutions of the ten DNA sequences were pooled together and rotoevaporated to half its original volume (~5 mL) under reduced pressure. A 0.1 M solution of tetra-n-butylammonium chloride in DMSO:$H_2O$ (1:1 v/v) (5.0 mL) was added to the crude DNA solution. This solution was then added to a 20-mL glass vial containing the aminooximated solid support 3 (1.50 g), which had previously been washed with 20% trimethylamine in MeCN (10 mL), filtered and blow-dried under argon; the glass vial was tightly sealed and mechanically agitated over a period of 3 h at 65° C. An aliquot (0.5 μL) of the capture reaction mixture was analyzed by RP-HPLC, which has only revealed the presence of benzamide and shorter than full-length DNA sequences relative to a similar analysis performed prior to the capture of the crude DNA sequence 10a (FIGS. 10A-10C).

Figure 10D:
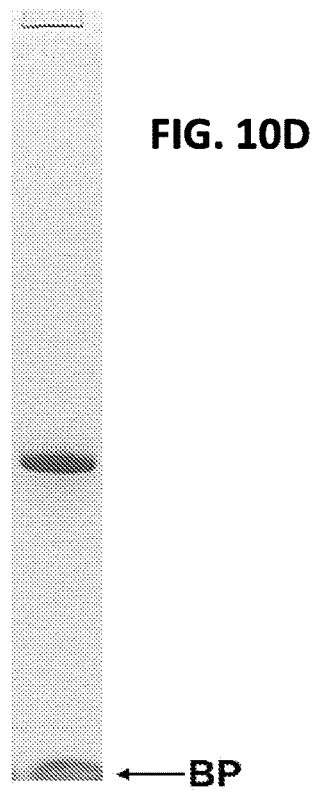
FIG. 10D shows the purity analysis of the solid-phase purified 12a by PAGE on 10-fold scale up.
Figures 12A, 12B, 12C, 12D:
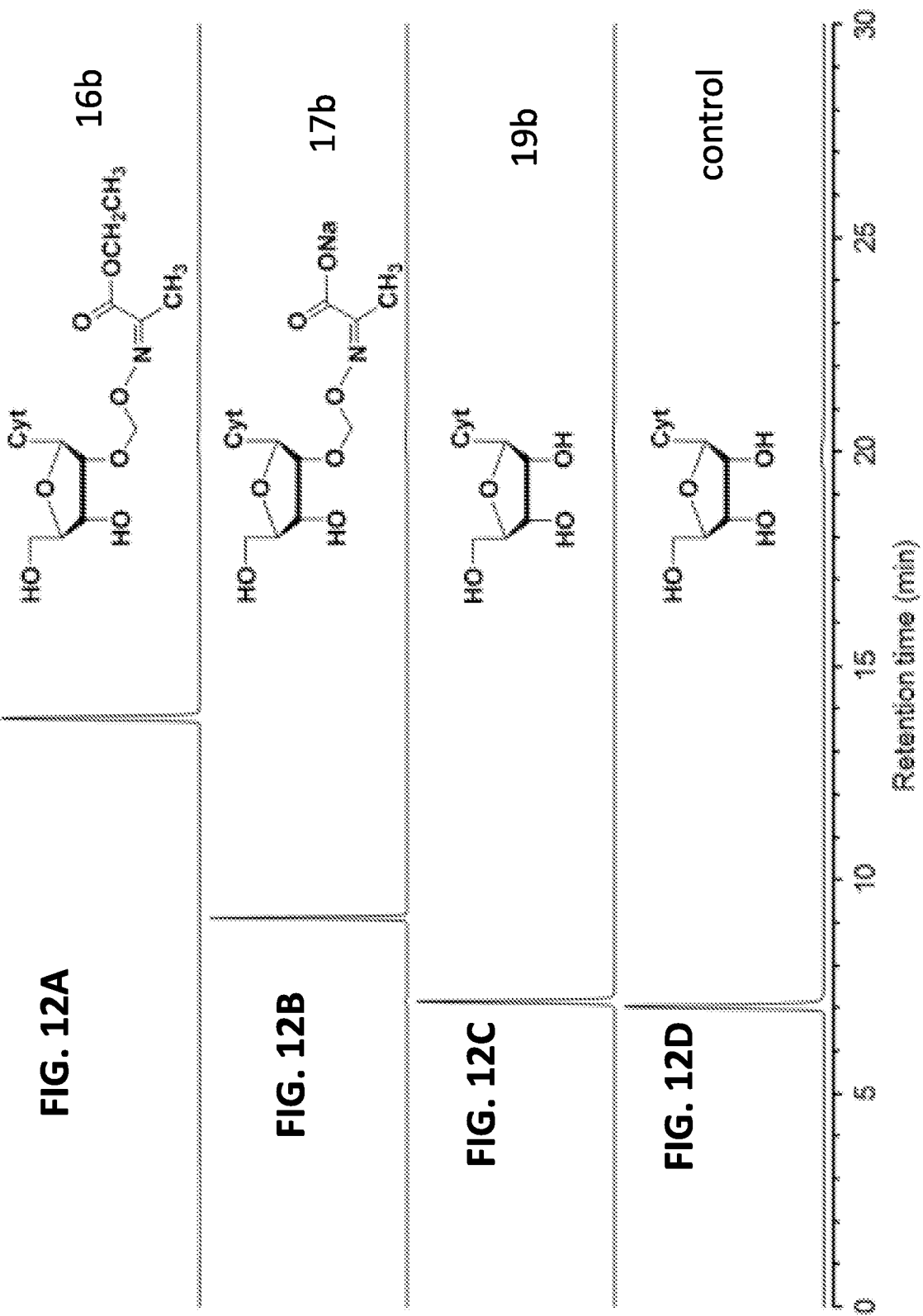
FIGS. 12A-12D show RP-HPLC profiles that demonstrate the sequential deprotection of cytosine-1-yl ribonucleoside 16b that is protected with a 2'-O-iminooxymethyl propanoate protecting group.

The solid support 11a was suspended in a solution of 10% $Et_3N$ in MeCN:$H_2O$ (1:1 v/v) (10 mL) and heated at 65° C. for 30 min whereupon the suspension is filtered through a glass-sintered funnel. This process was repeated twice under identical conditions and was followed by multiple anhydrous DMSO (5×10 mL) washes. Release of the purified DNA sequence from 11a was effected by treatment with 1.0 M TBAF in dry DMSO (5 mL) in a sealed 20-mL glass vial kept at 65° C. over a period of 3 h. Methoxytrimethylsilane (2 mL) and MeCN (2 mL) were added to the reaction mixture, which was allowed to stand at 25° C. for 30 min in order to consume unreacted fluoride ions. The suspension was filtered; the solid support was suspended in a solution of 10% Et$_3$N in MeCN:H$_2$O (1:1 v/v) (10 mL), heated at 65° C. for 30 min and then filtered through a glass-sintered funnel. This process was repeated once more under identical conditions. All the post-release filtrates were pooled together and rotoevaporated under vacuum until approximately 1 mL of the original volume is left. THF (20 mL) was then added to the filtrate; the DNA precipitate was centrifuged and the supernatant is carefully removed by suction. The DNA pellet was washed with THF (3×10 mL) and subjected to identical centrifugation and supernatant removal conditions. The pure nucleic acid sequence 12a was dried under reduced pressure and stored at −20° C. FIG. 10D shows the purity analysis of the solid-phase purified 12a by PAGE.

which is shown below, eluted from the column using a gradient of MeOH (0→6%) in CHCl$_3$. Pure product (1.14 g, 1.37 mmol) was isolated as a solid in a yield of 60%. +ESI-HRMS: Calcd for C$_{39}$H$_{72}$N$_4$O$_{10}$Si$_2$Na [M+Na]+ 835.4679, Found 835.4699.

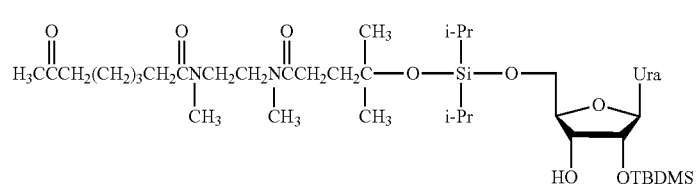

13

Example 13

This example demonstrates a synthesis of an RNA linker compound and its phosphoramidite derivative in accordance with an embodiment of the invention.

To compound 6b of Scheme 2 (780 mg, 2.28 mmol) and imidazole (184 mg, 2.70 mmol) in a flame-dried 25 mL-flask, was added under argon, dry DMF (5 mL) and N,N-diisopropylethylamine (2.35 mL, 13.5 mmol); the solution is then cooled to 0° C. Dichlorodiisopropylsilane (730 µL, 4.50 mmol) was added to the cold solution, which was left stirring for 1 h at 0° C. The reaction mixture was allowed to warm up to room temperature over a period of 4 h and then cooled to −60° C. A solution of 2′-O-tert-butyldimethylsilyl uridine (1.93 g, 5.40 mmol) and imidazole (368 mg, 5.40 mmol) in dry DMF (5 mL) was added dropwise to the reaction mixture, which was kept stirring at −60° C. for 1 h. The reaction was then allowed to warm up to 0° C. and was left stirring for 3 h at the same temperature. The reaction mixture was quenched by the addition of cold (0° C.) 5% aq. NaHCO$_3$ (40 mL) and EtOAc (40 mL); after vigorous shaking, the organic layer was collected and rotoevaporated to dryness under low pressure. The crude product was dissolved in a minimal volume of CHCl$_3$ (4 mL) and loaded on the top of a glass column packed with silica gel (~40 g) pre-equilibrated in CHCl$_3$. The product 13, the structure of which is shown below, eluted from the column using a gradient of MeOH (0→6%) in CHCl$_3$. Pure product (1.14 g, 1.37 mmol) was isolated as a solid in a yield of 60%.

Figure 9:
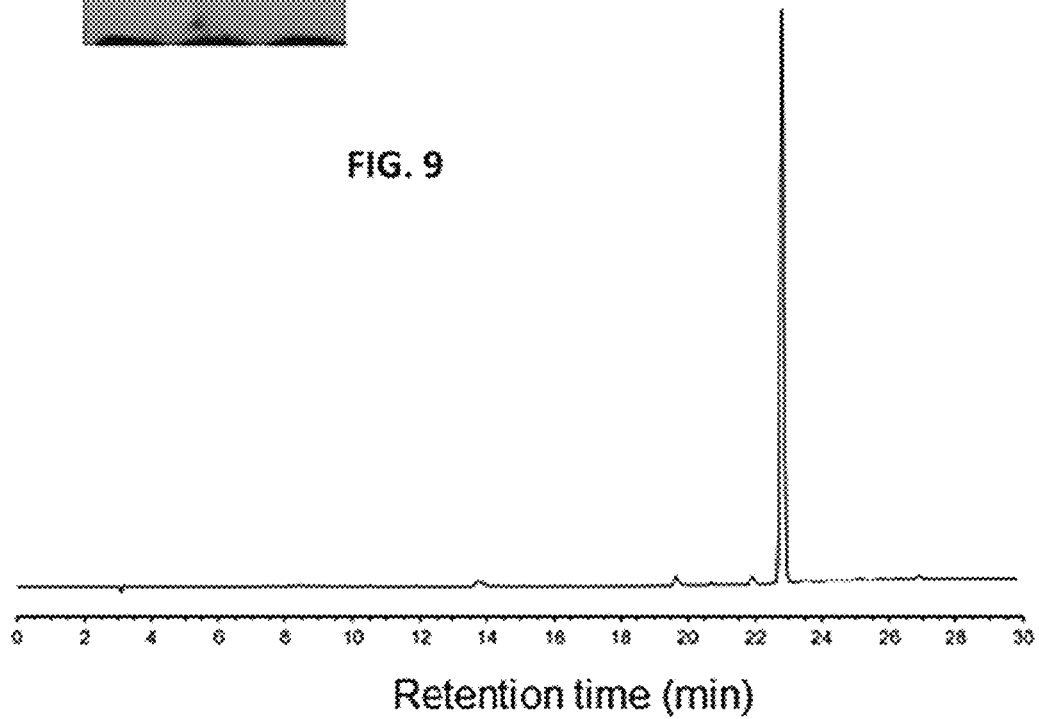
FIG. 9 shows the RP-HPLC chromatogram of silica gel-purified 5'-silylated 2'-O-tert-butyldimethylsilyl uridine 13.

The RP-HPLC of compound 13 is shown in FIG. 9. The RP-HPLC analysis is performed using a 5 µm Supelcosil LC-18S column (25 cm×4.6 mm) according to the following conditions: starting from 0.1 M triethylammonium acetate (pH 7.0), a linear gradient of 5.0% MeCN/min is pumped at a flow rate of 1 mL/min for 40 min.

The 5′-silylated-2′-O-tert-butyldimethylsilyl uridine 13 (835 mg, 1.00 mmol) was placed in a flame-dried 100 mL round-bottom flask and dissolved in anhydrous CH$_2$Cl$_2$ (10 mL). N,N-Diisopropylethylamine (536 µl, 3.00 mmol) was added to the solution followed by 2-cyanoethyl N,N-diisopropylchlorophosphoramidite (335 µL, 1.50 mmol). The reaction mixture was stirred at 25° C. for 5 h, quenched by the addition of H$_2$O (10 mL) and diluted with CH$_2$Cl$_2$ (25 mL). After vigorous shaking, the organic layer was collected, dried over anhydrous Na$_2$SO$_4$ and rotoevaporated under reduced pressure to afford an oil. The oily material was evenly spread on the top of a column packed with silica gel (~25 g) pre-equilibrated in benzene:Et$_3$N (9:1 v/v). The product, the structure of which is shown below, eluted from the column using benzene:Et$_3$N (9:1 v/v) as the eluent. Fractions containing the product were pooled together, concentrated under reduced pressure and dissolved in dry benzene (7 mL). The solution was frozen and then lyophilized under high vacuum to afford triethylamine-free product 14 (828 mg, 0.80 mmol) as a colorless oil in 80% yield. +ESI-HRMS: Calcd for C$_{48}$H$_{89}$N$_6$O$_{11}$Psi$_2$Na [M+Na]+ 1035.5758, Found 1035.5793.

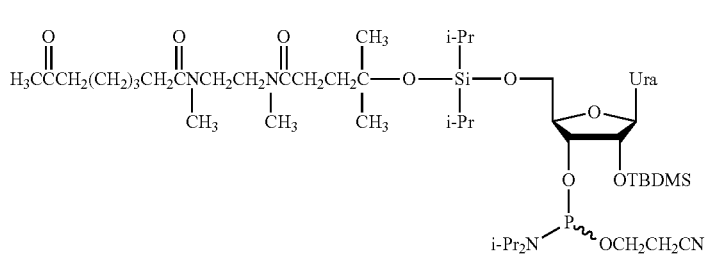

14

Example 14

Iminooxymethyl propanoate as a protecting group for the 2′-hydroxy position on RNA.

A formidable challenge in the chemical synthesis of oligoribonucleotides is to design a suitable 2′-hydroxy protecting group for ribonucleosides. A protecting group should optimally: (i) be easy to introduce; (ii) remain completely stable throughout the full assembly of the RNA sequence and particularly under the conditions used for nucleobase and phosphate deprotection and for the release of the sequence from the solid support; (iii) be totally removable under conditions that do not compromise the structural integrity of the RNA sequence. The 2'-hydroxy protecting group should preferably be structurally flexible and sterically small enough to permit rapid phosphoramidite-coupling kinetics and high coupling efficiencies. Disclosed herein is an iminooxymethyl group for 2'-hydroxy protection of ribonucleosides that demonstrates unprecedented cleavage through an innovative, entropy driven, intramolecular decarboxylative process.

Results and Discussion:

As shown in Scheme 5, the usefulness of 2'-O-aminooxymethylribonucleosides 15a-d in the development of novel 2'-hydroxy protecting groups is further demonstrated by mixing ribonucleoside 15a with ethyl pyruvate in the presence of drops of concentrated HCl in MeOH.

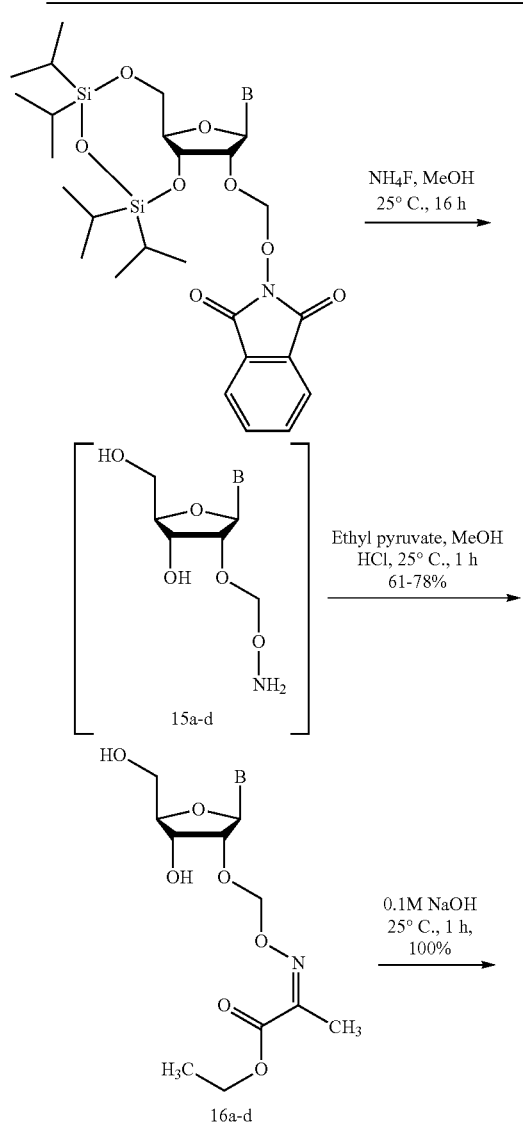

Scheme 5. Implementation of a 2'-O-iminooxymethyl propanoate protecting group for ribonucleosides and its removal through a decarboxylative elimination reaction.

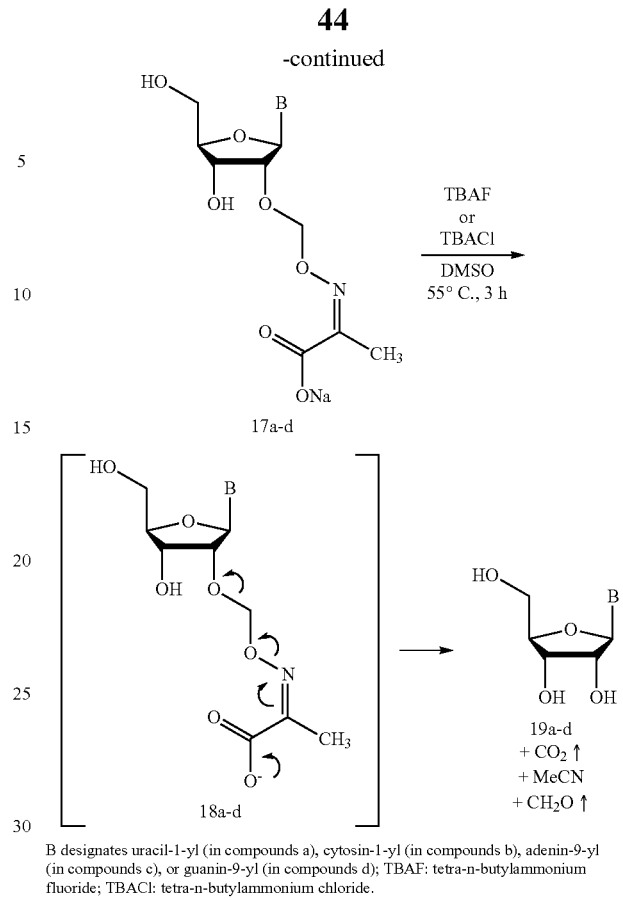

B designates uracil-1-yl (in compounds a), cytosin-1-yl (in compounds b), adenin-9-yl (in compounds c), or guanin-9-yl (in compounds d); TBAF: tetra-n-butylammonium fluoride; TBACl: tetra-n-butylammonium chloride.

After 1 hour at 25° C., 2'-O-iminooxymethyl ethyl propanate derivative 16a was isolated after purification with silica gel in a yield of 78%. Saponification of 16a upon treatment with NaOH (0.1 M) produced 2'-O-iminooxymethyl propanoate salt 17a in quantitative yield. Heating 17a in the presence of tetra-n-butylammonium fluoride (TBAF) or chloride (TBACl) in dry dimethyl sulfoxide (DMSO) (Scheme 5) resulted in a clean decarboxylation of 17a with the concomitant formation of MeCN and formaldehyde to provide uridine (19a) in quantitative yield based on RP-HPLC (reversed phase HPLC) analysis of the reaction (FIG. 11C). FIGS. 11A-11D provide the RP-HPLC profile for the silica-gel-purified 2'-O-protected uridine 16a (FIG. 11A); the de-esterified 2'-O-protected uridine 17a (FIG. 11B); and the 2'-O-deprotected uridine 19a (FIG. 11C), that is compared to a commercial sample of uridine (FIG. 11D, control). Uridine was used as an exemplary nucleoside, but the method is generally applicable to all four ribonucleosides and the protecting group is quantitatively removed when needed (FIGS. 12A-14D).

The solid-phase synthesis of a chimeric polyuridylic acid $(U_p)_{20}dT$ (FIGS. 15A-15C) served as a preliminary model for an assessment of iminooxymethyl propanoate protection/deprotection method for use in solid-phase synthesis of RNA synthesis. First, the 5'-O-protection of ribonucleoside 16a upon reaction with 4,4'-dimethoxytrityl chloride in dry pyridine produced 20 (Scheme 6) in a yield of 90% after purification with silica gel. The reaction of 20 with 2-cyanoethyl-N,N-diisopropylchlorophosphoramidite in the presence of triethylamine gives the ribonucleoside phosphoramidite 21 in a post-purification yield of 88%.

Scheme 6.

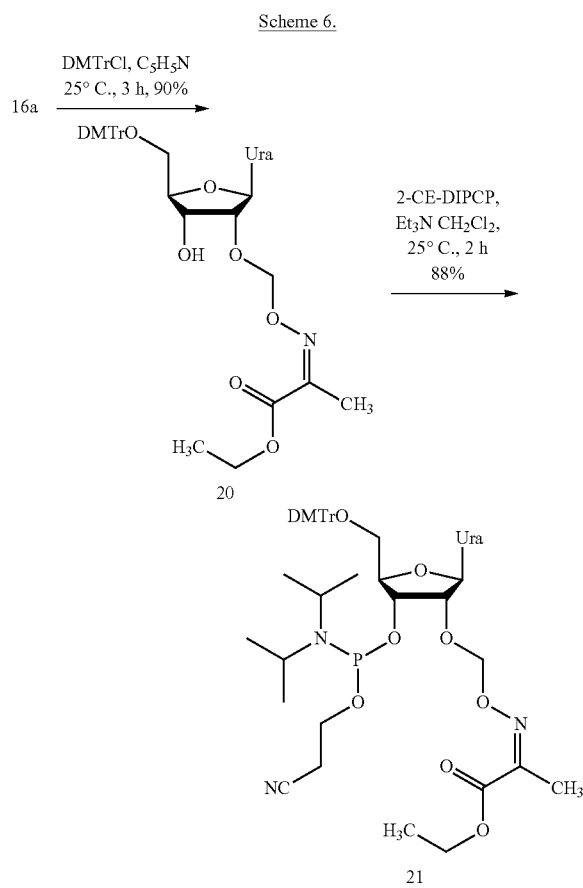

Synthesis of Ribonucleoside Phosphoramidite 21.

The coupling kinetics and efficiency of ribonucleoside phosphoramidite 21 were evaluated through the solid-phase synthesis of $(U_p)_{20}dT$ (FIG. 15). An identical RNA control sequence was also prepared by using a commercial uridine 2'-O-(tert-butyldimethylsilyl) phosphoramidite with the purpose of comparing the quality of the RNA sequences produced from each phosphoramidite monomer. Upon completion of the solid-phase RNA syntheses, the RNA sequence constructed from 21 was subjected to treatment with tetra-n-butylammonium hydroxide (0.5 M) for 3 h at 25° C. to concurrently de-esterify the 2'-O-protecting groups, remove the 2-cyanoethyl-phosphate protecting groups, and release the RNA sequence from the solid support. The basic nucleic acid solution was then neutralized by adding a four molar equivalent of glacial acetic acid and concentrated to dryness. Without isolation, the crude RNA sequence was dissolved in a solution of TBAF or TBACl (0.5 M) in dry DMSO and heated at 55° C. for 3 h to induce decarboxylation of the 2'-O-iminooxypropanoate groups. The control RNA sequence was fully deprotected and released from the support under published conditions. Analytical samples of the unpurified and desalted RNA sequences were analyzed by RP-HPLC and polyacrylamide gel electrophoresis (PAGE) under denaturing conditions (FIGS. 15A-15C and 16, respectively). Moreover, enzymatic hydrolysis of the crude, de-esterified, 2'-O-protected $(U_p)_{20}dT$ (FIG. 15A) catalyzed by snake venom phosphodiesterase (SVP) and alkaline phosphatase cleanly led to the production of 17a (Scheme 5) and thymidine (FIG. 17A), whereas the enzymatic hydrolysis of crude, de-esterified, 2'-O-protected $(U_p)_{20}dT$ revealed, after decarboxylation, only the presence of uridine (19a, Scheme 5) and thymidine (FIG. 17B), thereby indicating complete cleavage of the 2'-O-protecting groups from the chimeric RNA sequence.

Materials and Methods:

Common chemicals and solvents in addition to DMSO, glacial acetic acid, acetic anhydride, hydrochloric acid, aqueous ammonia, potassium carbonate, pyridine, triethylamine, methanol, sodium hydroxide, concentrated hydrochloric acid, $Et_3N.3HF$, DEPC-treated $H_2O$, sulfuryl chloride, N-hydroxyphthalimide, 1,8-diazabicyclo[5.4.01]-undec-7-ene (DBU), ammonium fluoride, tetra-n-butylammonium fluoride (TBAF), tetra-n-butylammonium chloride (TBACl), tetra-n-butylammonium hydroxide (TBAOH), tetra-n-butylammonium acetate (TBAOAc), tetra-n-butylammonium cyanide (TBACN), ethyl pyruvate, 4,4'-dimethoxytrityl chloride, 2-cyanoethyl N,N-diisopropylchlorophosphoramidite, and anhydrous solvents (MeCN, $CH_2Cl_2$, $C_6H_6$, $C_6D_6$, pyridine, THF) and DMSO-d6 were purchased from commercial sources and used without further purification. N4-phenoxyacetyl-3',5'-O-(1,1,3,3-tetraisopropyldisiloxane-1,3-diyl)cytidine, N6-phenoxyacetyl-3',5'-O-(1,1,3,3-tetra-isopropyldisiloxane-1,3-diyl)adenosine, N2-phenoxyacetyl-3',5'-O-(1,1,3,3-tetraisopropyldisiloxane-1,3-diyl)guanosine, 3',5'-O-(1,1,3,3-tetraisopropyldisiloxane-1,3-diyl)uridine, 5'-O-(4,4'-dimethoxytrityl)-2'-O-(tert-butyldimethylsilyl)uridine phosphoramidite, PD-10 (Sephadex G-25M) columns, 0.25 M 5-benzylthio-1H-tetrazole in MeCN or 0.25 M 5-ethylthio-1H-tetrazole in MeCN and all ancillary reagents commonly used in solid-phase DNA/RNA synthesis including succinyl long chain alkylamine controlled-pore glass (CPG) support functionalized with 2'-deoxythymidine, as the leader nucleoside, were obtained from reputable sources and used as received.

Reagent for enzymatic hydrolysis of RNA sequences such as magnesium chloride, Tris.Cl, snake venom phosphodiesterase (*Crotallus adamanteus*) and bacterial alkaline phosphatase (*E. coli*) were bought from commercial sources and used without further purification. Flash chromatography purifications were performed on glass columns (2.5 cm or 6.0 cm I.D.) packed with silica gel 60 (230-400 mesh), whereas analytical thin-layer chromatography (TLC) analyses were conducted on 2.5 cm×7.5 cm glass plates coated with a 0.25 mm thick layer of silica gel 60 $F_{254}$. Analytical RP-HPLC analyses were done using a 5 µm Supelcosil LC-18S column (25 cm×4.6 mm) according to the following conditions: starting from 0.1 M triethylammonium acetate pH 7.0, a linear gradient of 1% MeCN/min was pumped at a flow rate of 1 mL/min for 40 min. In all RP-HPLC chromatograms, peak heights were normalized to the highest peak, which was set to 1 arbitrary unit. 2 M Triethylammonium acetate buffer was purchased from Applied Biosystem and diluted to 0.1 M with HPLC grade water prior to use.

Electrophoresis was conducted on a 20 cm×40 cm×0.75 mm 7 M-urea 20% polyacrylamide gel. The gel was run at 350 V, using 1×Tris Borate EDTA as the electrolyte, until the bromphenol blue dye traveled 75%-80% of the gel's length. The gel was then immersed in 250 mL of Staining buffer (1:5:20 (v/v/v) formamide:isopropyl alcohol:dd$H_2O$) to which was added 10 mL of Stains-all (1 mg/mL) in formamide. The gel was stained over about 4 h in the dark. The staining solution was discarded and the gel was rinsed three times with 250 mL distilled water. The gel was exposed to natural light until the purple background disappeared. Unpurified de-esterified 2'-O-protected $(Up)_{20}dT$ and fully 2'-O-deprotected $(Up)_{20}dT$ appeared as a sharp purple or blue band, respectively. All NMR experiments were performed using a spectrometer operating at 300.13, 75.47 and 121.5 MHz for one-dimensional 1H,1H-decoupled $^{13}C$ and $^1$H-decoupled $^{31}P$, respectively. Samples were maintained at a temperature of 298 K. All spectra were recorded in deuterated solvents and chemical shifts δ reported in parts per million (ppm) relative to appropriate internal references.

High resolution and low resolution mass spectrometry analyses of new compounds and RNA sequences were performed under contract at a reputable mass spectrometry facility.

General Procedure for the Synthesis of Ribonucleoside 2'-O-Iminooxymethyl Propanoicacid Ethyl Esters (16a-d).

To a solution of 3',5'-O-(1,1,3,3-tetraisopropyldisiloxane-1,3-diyl)-2'-O-phthalimidooxymethyl)uridine (3.3 g, 5.0 mmol) in MeOH (25 mL) was added ammonium fluoride (1.8 g, 50 mmol). The heterogeneous reaction mixture was stirred at about 25° C. until desilylation and dephthalimidation were complete (16 h) as indicated by TLC [$CHCl_3$:MeOH (9:1 v/v)]. To this mixture was added a solution (20 mL) of ethyl pyruvate (6.9 g, 60 mmol) in MeOH:$H_2O$ (1:1, v/v) containing concentrated HCl (0.5 mL); the reaction mixture was stirred over 1 h at 55° C. Approximately one half of the volatiles were removed by rotoevaporation under vacuum; the material was left was mixed with dry silica gel (30 g) and allowed to dry overnight. The gel mix was re-suspended in $CH_2Cl_2$ (30 mL) and layered on the top of a chromatography column packed with silica gel (150 g) pre-equilibrated in $CH_2Cl_2$. The product was eluted from the column using a gradient of MeOH (0→6%) in $CH_2Cl_2$. Fractions containing the pure product were collected and rotoevaporated under reduced pressure to give 16a (1.5 g, 3.9 mmol) as a white solid in a yield of 78%. The ribonucleoside 2'-O-iminooxyethyl propanoic acid ethyl ester 16b-d were prepared in a similar manner and were isolated with yields in the range of 61%-76%. 16a: $^1$H NMR (300 MHz, DMSO-d6) δ11.30 (br s, 1H), 7.85 (d, J=8.1 Hz, 1H), 5.88 (d, J=5.6 Hz, 1H), 5.59 (dd, J=8.1, 2.2 Hz, 1H), 5.30 (m, 2H), 5.22 (d, J=5.4 Hz, 1H), 5.13 (t, J=5.1 Hz, 1H), 4.30 (t, J=5.4 Hz, 1H), 4.19 (q, J=7.1 Hz, 2H), 4.15 (m, 1H), 3.87 (m, 1H), 3.66-3.51 (m, 2H), 1.95 (s, 3H), 1.24 (t, J=7.1 Hz, 3H). $^{13}$C NMR (75 MHz, DMSO-d6): δ162.9, 162.8, 150.7, 150.5, 140.5, 101.8, 96.7, 85.9, 85.2, 79.2, 68.6, 61.4, 60.7, 13.9, 11.6.+ESI-HRMS: Calcd. for $C_{15}H_{22}N_3O_9$ [M+H]$^+$ 388.1351, Found: 388.1349. 16b: $^1$H NMR (300 MHz, DMSO-d6) δ9.29 (br s, 1H), 8.43 (br s, 1H), 8.21 (d, J=7.8 Hz, 1H), 6.06 (d, J=7.8 Hz, 1H), 5.80 (d, J=3.7 Hz, 1H), 5.37 (m, 2H), 5.28 (m, 1H), 4.30 (t, J=4.2 Hz, 1H), 4.22 (q, J=7.1 Hz, 2H), 4.12 (t, J=5.2 Hz, 1H), 3.90 (m, 1H), 3.73-3.56 (m, 2H), 1.98 (s, 3H), 1.25 (t, J=7.1 Hz, 3H). $^{13}$C NMR (75 MHz, DMSO-d6): δ162.9, 160.7, 150.7, 148.7, 143.5, 96.9, 93.9, 87.7, 84.8, 79.8, 67.8, 61.4, 59.8, 13.9, 11.7.+ESI-HRMS: Calcd. for $C_{15}H_{23}N_4O_8$ [M+H]$^+$ 387.1510, Found: 387.1511. 16c: $^1$H NMR (300 MHz, DMSO-d6) δ8.29 (s, 1H), 8.08 (s, 1H), 7.32 (br s, 2H), 5.99 (d, J=6.4 Hz, 1H), 5.27 (m, 2H), 4.88 (dd, J=6.3, 6.1 Hz, 1H), 4.37 (m, 1H), 4.11 (dq, J=7.1, 1.5 Hz, 2H), 4.00 (q, J=3.1 Hz, 1H), 3.62 (m, 2H), 1.64 (s, 3H), 1.19 (t, J=7.1 Hz, 3H). $^{13}$C NMR (75 MHz, DMSO-d6): δ162.4, 156.1, 152.2, 150.3, 148.8, 139.9, 119.3, 96.6, 86.4, 86.2, 79.1, 79.0, 69.2, 61.6, 61.2, 13.9, 11.0.+ESI-HRMS: Calcd. for $C_{16}H_{23}N_6O_7$ [M+H]$^+$ 411.1623, Found: 411.1623.

16d: $^1$H NMR (300 MHz, DMSO-d6) δ10.61 (s, 1H), 7.88 (s, 1H), 6.44 (br s, 2H), S55.80 (d, J=6.4 Hz, 1H), 5.27 (m, 3H), 5.08 (m, 1H), 4.66 (dd, J=6.3, 6.1 Hz, 1H), 4.28 (m, 1H), 4.13 (q, J=7.1 Hz, 2H), 3.57 (m, 2H), 1.78 (s, 3H), 1.21 (t, J=7.1 Hz, 3H). $^{13}$C NMR (75 MHz, DMSO-d6): δ162.6, 156.6, 153.6, 151.2, 150.5, 135.3, 116.5, 96.8, 85.8, 84.4, 80.0, 69.3, 61.4, 61.3, 13.9, 11.3.+ESI-HRMS: Calcd. for $C_{16}H_{22}N_6O_8Na$[M+Na]$^+$449.1391, Found: 449.1396.

General Procedure for the Preparation of Ribonucleoside 2'-O-Iminooxymethyl Propanoates (17a-d).

The ribonucleoside 16a (1 mg, about 2.6 μmol) was dissolved in aqueous 0.1 M NaOH (1 mL). The solution was stirred at 25° C. over a period of 1 h whereupon 1 M AcOH (0.5 mL) was added to neutralize the excess NaOH. The reaction mixture was then rotoevaporated to dryness under reduced pressure to afford 17a in quantitative yields as demonstrated by RP-HPLC analysis of the saponification reaction (FIGS. 11A-11D). Saponification of the ribonucleosides 16b-d was performed under similar conditions to provide 17b-d in similar yields.

17a: −ESI-HRMS: Calcd. for $C_{13}H_{16}N_3O_9$[M]$^-$358.0892, Found: 358.0886.

17b: −ESI-HRMS: Calcd. for $C_{13}H_{17}N_4O_8$[M]$^-$357.1052, Found: 357.1042.

17c: −ESI-HRMS: Calcd. for $C_{14}H_{17}N_6O_7$[M]$^-$381.1164, Found: 381.1167.

17d: +ESI-HRMS: Calcd. for $C_{14}H_{17}N_6O_8Na_2$ [M+2Na]$^+$ 443.0898, Found: 443.0900

General Procedure for the Decarboxylation of Ribonucleoside 2'-O-Iminooxymethyl Propanoate 17a-d.

Figures 13A, 13B, 13C, 13D:
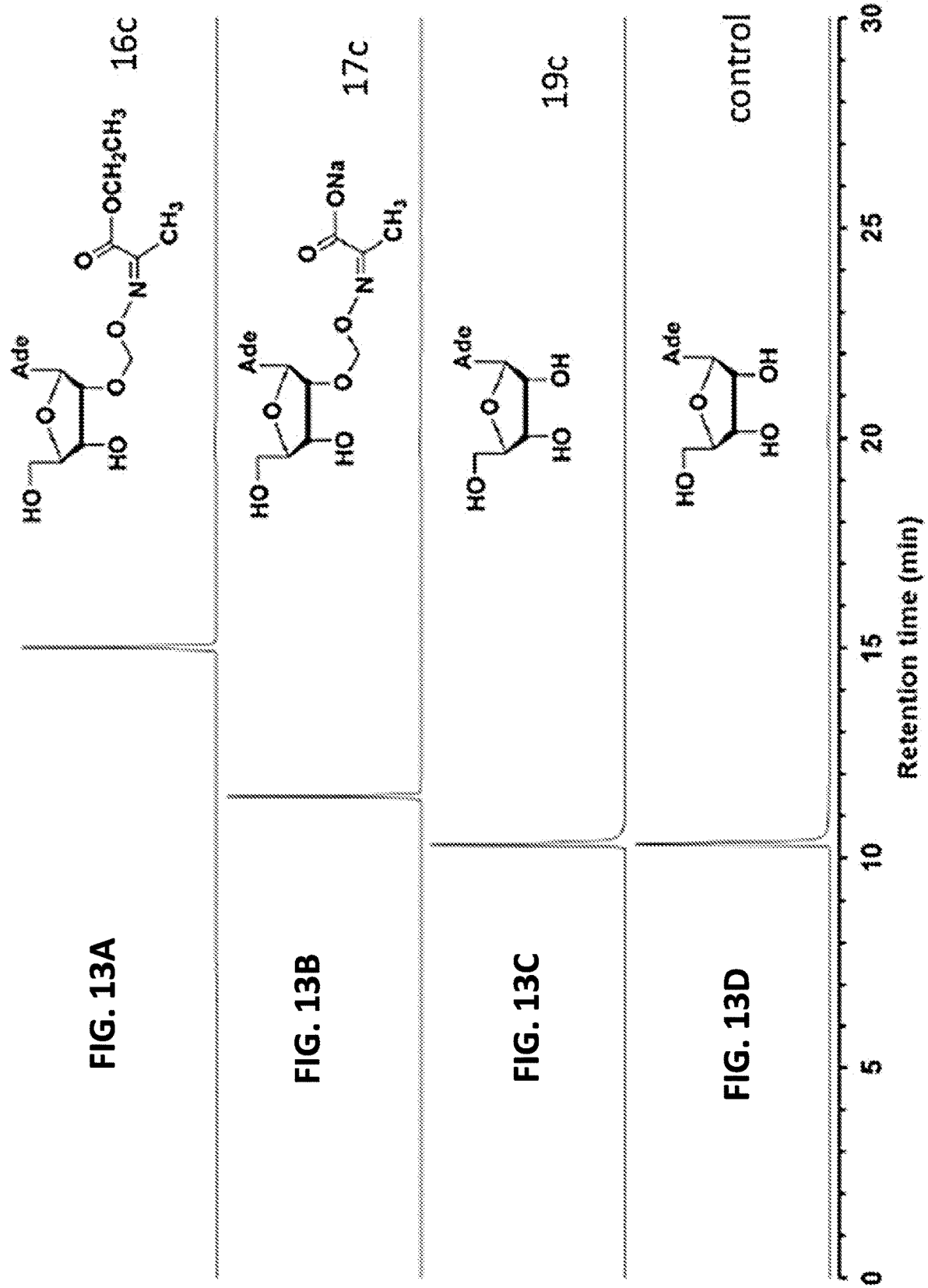
FIGS. 13A-13D show RP-HPLC profiles that demonstrate the sequential deprotection of adenine-9-yl ribonucleoside 16c that is protected with a 2'-O-iminooxymethyl propanoate protecting group.
Figures 14A, 14B, 14C, 14D:
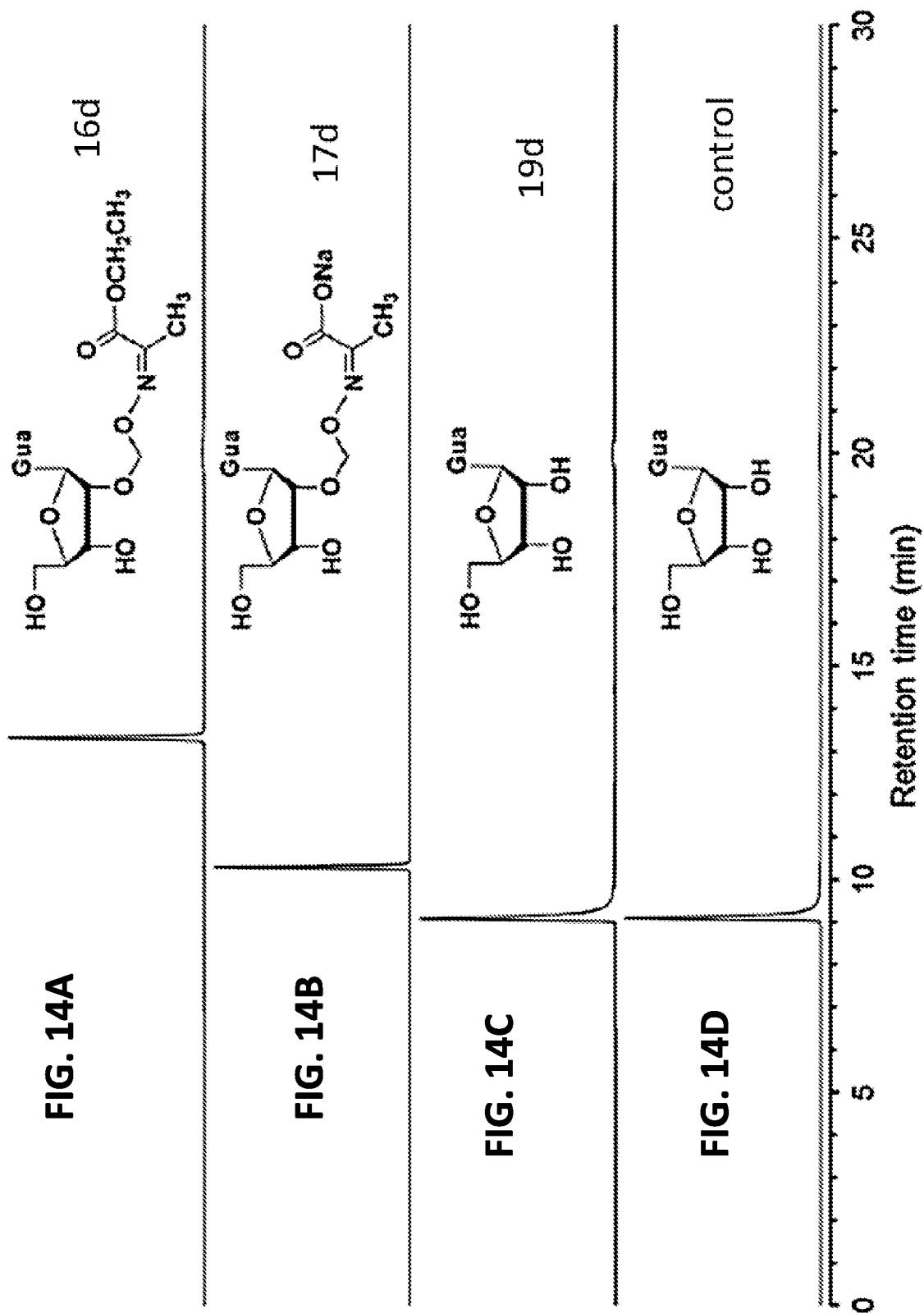
FIGS. 14A-14D show RP-HPLC profiles that demonstrate the sequential deprotection of guanine-9-yl ribonucleoside 16d that is protected with a 2'-O-iminooxymethyl propanoate protecting group.
Figure 16:
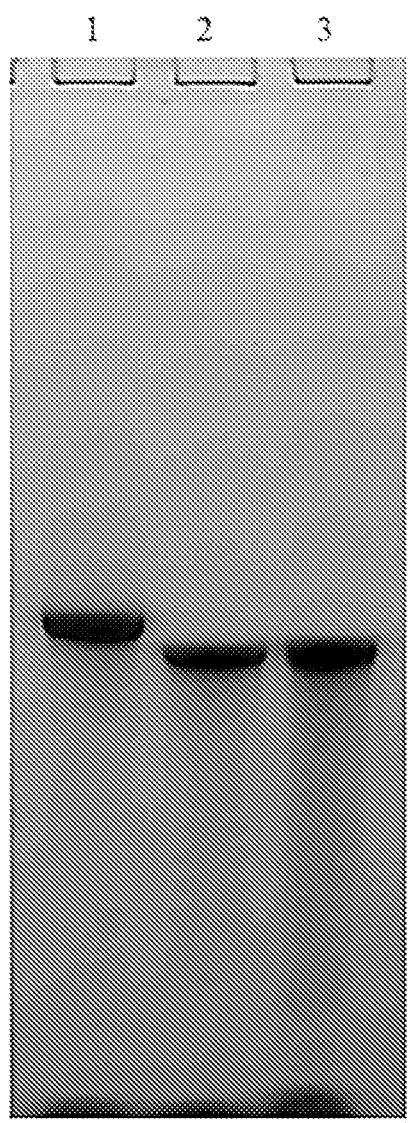
FIG. 16 shows the purity analysis of unpurified and desalted de-esterified 2'-O-protected $(U_p)_{20}dT$ (lane 1), fully 2'-O-deprotected $(U_p)_{20}dT$ (lane 2), and a fully 2'-O-deprotected $(U_p)_{20}dT$ control sequence (lane 3) RNA sequences, with bromophenol blue used as a marker and appearing as a large band at the bottom of the gel.

De-esterified 2'-O-protected uridine 17a (0.1 mg) was placed in a 4-mL screw-capped glass vial. A solution of 0.5 M tetra-n-butylammonium fluoride or tetra-n-butylammonium chloride in dry DMSO (0.5 mL) was added to the vial, which was then sealed and placed in a heat block kept at 55° C.; the reaction mixture was kept at this temperature for 60 min. As shown in FIGS. 11A-11D, RP-HPLC analysis of the decarboxylation reaction displayed complete disappearance of 17a and appearance of uridine (19a) as the sole product. The decarboxylation of de-esterified 2'-O-protected ribonucleosides (17b-d) was carried out under conditions identical to those described for the 2'-O-deprotection of 17a. FIGS. 12, 13 and 14 showed quantitative decarboxylation of 17b-d and production of 19b-d, as determined by RP-HPLC analysis of each 2'-O-deprotection reaction. All decarboxylation reactions led to the quantitative production of acetonitrile, as convincingly demonstrated by $^{13}$C-NMR analysis of the 2'-O-deprotection of 17a (not shown).

Uridine 5'-O-(4,4'-dimethoxytrityl)-2'-O-iminooxymethyl Propanoic Acid Ethyl Ester (20).

Uridine 2'-O-iminooxymethyl propanoic acid ethyl ester (16a, 1.2 g, 3.0 mmol) was co-evaporated with anhydrous pyridine (2×20 ml) and then dissolved in anhydrous pyridine (20 mL). 4,4'-Dimethoxytrityl chloride (1.2 g, 3.6 mmol) was added to the solution, which was then allowed to stir for 3 h at about 25° C. The reaction mixture was rotoevaporated under reduced pressure to a gummy material, which was dissolved in $CH_2Cl_2$ (150 mL). The solution was subjected to extraction with a saturated aqueous $NaHCO_3$ solution (70 mL). The organic layer was collected, dried over $Na_2SO_4$ and filtered. The filtrate was rotoevaporated under reduced pressure; the material left was purified by chromatography on silica gel using a gradient of MeOH (0→2%) in $CH_2Cl_2$ as the eluent to afford 20 as a solid (1.86 g, 2.70 mmol) in a yield of 90%.

$^1$H NMR (300 MHz, DMSO-d6) δ11.37 (s, 1H), 7.67 (d, J=8.1 Hz, 1H), 7.39 (m, 1H), 7.32 (m, 3H), 7.25 (m, 5H), 6.89 (d, J=8.4 Hz, 4H), 5.81 (d, J=4.1 Hz, 1H), 5.40 (m, 1H), 5.32 (dd, J=7.8, 6.4 Hz, 3H), 4.34 (dd, J=4.8, 4.4 Hz, 1H), 4.22 (m, 1H), 4.16 (q, J=7.1 Hz, 2H), 3.96 (m, 1H), 3.74 (s, 6H), 1.95 (s, 3H), 1.21 (t, J=7.1 Hz, 3H). $^{13}$C NMR (75 MHz, DMSO-d6): δ 162.86, 162.82, 158.1, 150.7, 150.2, 149.6, 144.6, 140.6, 136.1, 135.3, 135.1, 129.7, 127.9, 127.7, 126.8, 123.9, 113.2, 101.6, 97.1, 87.4, 85.8, 82.6, 79.3, 68.5, 62.9, 61.3, 55.0, 13.9, 11.6.+ESI-HRMS Calcd for $C_{36}H_{39}N_3O_{11}Cs$ [M+Cs]$^+$ 822.1634, Found 822.1638.

Uridine 5'-O-(4,4'-dimethoxytrityl)-3-O-[N,N-diisopropylamino)(2-cyanoethyloxy)]phosphinyl-2'-O-iminooxymethyl Propanoic Acid Ethyl Ester (21).

To a solution of 20 (1.72 g, 2.50 mmol) in anhydrous $CH_2Cl_2$ (30 mL) was added, under an argon atmosphere, Et3N (1.39 mL, 10.0 mmol) and 2-cyanoethyl N,N-diisopropyl-chlorophosphoramidite (1.31 mL, 5.00 mmol). The reaction mixture was stirred at about 25° C. until complete disappearance of 20 (2 h) as indicated by TLC [$C_6H_6$:$Et_3N$ (9:1 v/v)]. The reaction mixture was then diluted with $CH_2Cl_2$ (50 mL) and extracted with H2O (10 mL). The organic layer was collected, dried over anhydrous $Na_2SO_4$ and filtered. The filtrate was rotoevaporated to dryness under vacuum. The crude phosphoramidite was purified by chromatography on silica gel using $C_6H_6$:$Et_3N$ (9:1 v/v) as the eluent. Fractions containing the pure product were pooled together and rotoevaporated to dryness under low pressure. The material left was dissolved in dry $C_6H_6$ (3 mL); the resulting solution was added to cold (−78° C.) stirred hexane (100 mL). The pure phosphoramidite precipitated immediately as a white solid. Hexane was removed by decantation; the wet precipitate was dissolved in dry $C_6H_6$ (5 mL) and lyophilized under high vacuum. $Et_3N$-free 21 was isolated as a white powder (1.95 g, 2.20 mmol) in a yield of 88%.

$^{31}$P NMR (121 MHz, $C_6D_6$): δ150.5, 149.5.+ESI-HRMS: Calcd for $C_{45}H_{56}N_5O_{12}P$ (M+H)$^+$890.3736, Found 890.3744.

Solid-Phase Synthesis of Chimeric Polyuridylic Acid Sequences.

The solid phase synthesis of 5'-r(UUUUUUUUUUUUUUUUUU-UU)dTRU$_p$)$_{20}$dTπ was conducted on a scale of 0.2 µmole in the "trityl-off" mode using a succinyl long chain alkylamine controlled-pore glass (CPG) support functionalized with 2'-deoxythymidine as the leader nucleoside. The synthesis was carried out using a DNA/RNA synthesizer and the ribonucleoside phosphoramidite monomer 21, which was dissolved in dry MeCN to a concentration of 0.1 M. 5-Benzylthio-1H-tetrazole (0.25 M in MeCN) and all other ancillary reagents necessary for solid-phase RNA synthesis were obtained from commercial sources. The reaction time for each phosphoramidite coupling step was set to 3 min. The stepwise coupling efficiency was determined to be 99±5% by measuring, spectrophotometrically at 498 nm, the ratio of the molar amount of trityl cation released after the second and last synthesis cycles. The dedimethoxytritylation, capping and oxidation steps of any synthesis cycle were each performed over a period of 60 s. The control chimeric RNA sequence (U$_p$)$_{20}$dT was synthesized using commercial 2'-O-(tert-butyldimethylsilyl)uridine phosphoramidite monomer under the control of the same automated synthetic protocol.

Deprotection and Characterization of the Chimeric RNA Sequences.

The solid-phase-linked 5'-dedimethoxytritylated RNA sequence was placed into a 4-mL screw-capped glass vial and subjected to treatment with 0.5 M tetra-n-butylammonium hydroxide 100 µL) for 3 h at 25° C. in order to de-esterify the 2'-O-protecting groups, remove the 2-cyanoethyl phosphate protective groups and release the RNA sequence from the solid support. The solution was neutralized by addition of 1 M acetic acid (200 µL) and then evaporated to dryness using a stream of air. Without isolation or further purification, the de-esterified 2'-O-protected RNA sequence was dissolved in a 0.5 M TBAF or TBACl solution in dry DMSO (500 µL) and heated to 55° C. over a period of 3 h to achieve complete decarboxylation of the 2'-O-imminooxypropanoate groups. The solution was concentrated to a volume of about 100 µL, diluted with about 900 µL of DEPC-treated water and desalted using a PD-10 (Sephadex G-25M) column. Unpurified and desalted (U$_p$)$_{20}$dT was eluted from the column using DEPC-treated $H_2O$ as the eluent. Fractions (1 mL) were collected and those containing the RNA sequence (A$_{260}$) were pooled together for analysis by RP-HPLC (FIG. 15B), polyacrylamide gel electrophoresis (FIG. 16, lane 2) and for characterization by ESI mass spectrometry. The control RNA sequence (U$_p$)$_{20}$dT was released from the support and fully deprotected according to published protocols. -ESI-MS analysis of de-esterified of 2'-O-protected (U$_p$)$_{20}$dT: Calcd. for $C_{270}H_{294}N_{62}O_{225}P_{20}$[M-20H]$^-$8647, Found 8650. –ESI-MS analysis of fully 2'-O-deprotected (U$_p$)$_{20}$dT: Calcd. for $C_{190}H_{214}N_{42}O_{165}P_{20}$ [M-4H]$^{4-}$6342, Found 6342.

Enzymatic Hydrolysis of the Chimeric RNA Sequences.

Figure 17A:
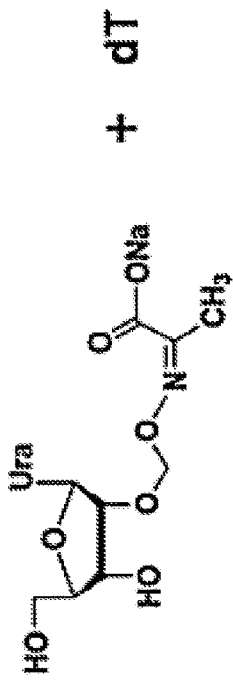
FIGS. 17A-17C provide RP-HPLC analysis of SVP/BAP hydrolysates. SVP: snake venom phosphodiesterase; BAP: bacterial alkaline phosphatase; Ura: uracil-1-yl; T: thymin-1-yl.
Figure 17B:
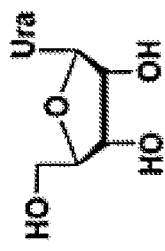
Figure 17C:
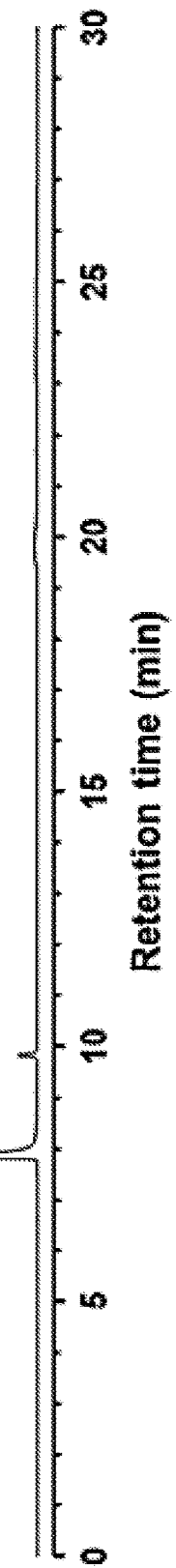

One OD$_{260}$ unit of each of the unpurified and desalted chimeric RNA sequence and control RNA sequence (U$_p$)$_{20}$dT was pipetted into separate microcentrifuge tubes. The RNA solution of each tube was evaporated to dryness using a stream of air. To each tube was added 1.0 M Tris.Cl buffer pH 9.0 (6 µL), 1.0 M MgCl$_2$ (8 µL) and water (75 µL) followed by, after mixing, snake venom phosphodiesterase (*Crotallus adamanteus*, 0.015 U, 5 µL) and bacterial alkaline phosphatase (*E. coli*, 0.7 U, 6 µL). The enzymatic reactions were allowed to proceed at 37° C. for 16 h. Deactivation of the enzymes was carried out by heating the digests at 90° C. for 3 min. Each digest was centrifuged at 14,000 rpm for 5 min at 25° C. An aliquot (50 µL) of each digest was analyzed by RP-HPLC using a 5 µm Supelcosil LC-18S column under the following conditions: starting from 0.1 M triethylammonium acetate (pH 7.0), a linear gradient of 1% MeCN/min was pumped at a flow rate of 1 mL/min for 40 min. RP-HPLC chromatograms of the digests are shown in FIGS. 17A-17C.

V. Exemplary Embodiments

The following numbered paragraphs illustrate exemplary embodiments of the disclosed technology.

Paragraph 1. A method of purifying an oligonucleotide or an oligonucleotide analog composed of "b" nucleotides from a mixture comprising the oligonucleotide or oligonucleotide analog and at least one oligonucleotide or oligonucleotide analog composed of "a" nucleotides, wherein b≠a, the method comprising:

(i) providing a protected nucleoside or nucleoside analog of formula (I) or (Ia) functionalized with an activatable phosphorus-containing entity

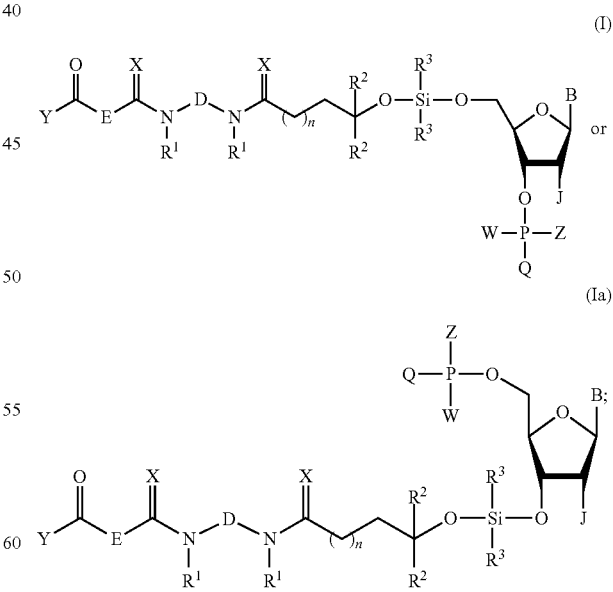

(ii) providing a mixture comprising an optionally protected first oligonucleotide or oligonucleotide analog V' composed of b-1 nucleotides or nucleotide analogs and having a free 5'-terminal OH group, wherein the first oligonucleotide V' comprises phosphate or phosphorothioate triester linkages, or a combination thereof, and wherein the first oligonucleotide V' is linked at its 3'-terminus to a solid support, wherein at least one oligonucleotide or oligonucleotide analog composed of "a" nucleotides is also linked to the solid support;

(iii) coupling the first oligonucleotide V' with the protected nucleoside or nucleoside analog of formula (I) or (Ia), to provide a second oligonucleotide of the formula (II) or (IIa)

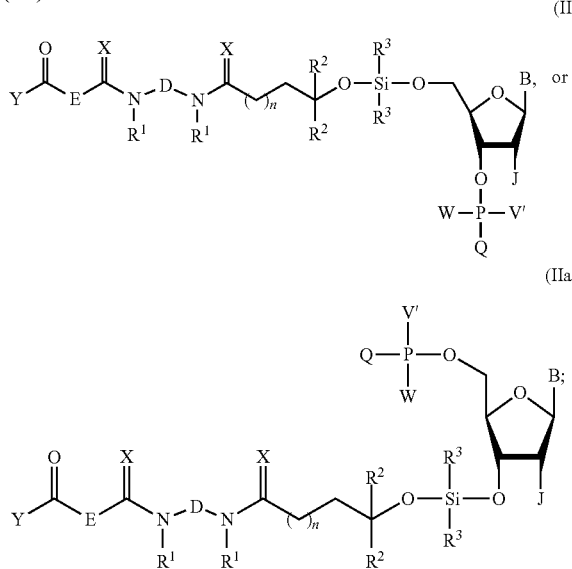

(iv) oxidizing or sulfurizing, optionally deprotecting, and cleaving the second oligonucleotide or oligonucleotide analog of the formula (II) or (IIa) from the solid support to form a mixture comprising a third oligonucleotide of the formula (III) or (IIIa)

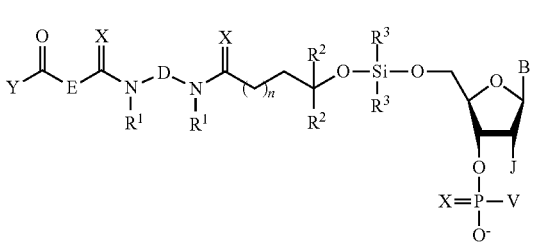

wherein V is the moiety resulting after optional deprotection of the second oligonucleotide or oligonucleotide analog and wherein V is not linked to the solid support;

(v) reacting the mixture comprising the third oligonucleotide or oligonucleotide analog of the formula (III) or (IIIa) with a silica-attached linker compound of the formula:

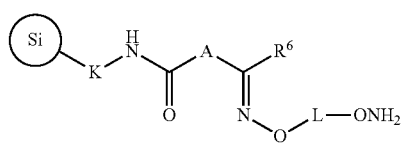

wherein A, K, and L are independently $C_2$-$C_{10}$ alkanediyl and $R^6$ is H or $C_1$-$C_6$ linear or branched alkyl or $C_3$-$C_8$ cycloalkyl, and wherein

is silica, to form a linker-attached oligonucleotide or oligonucleotide analog of the formula (IV) or (IVa)

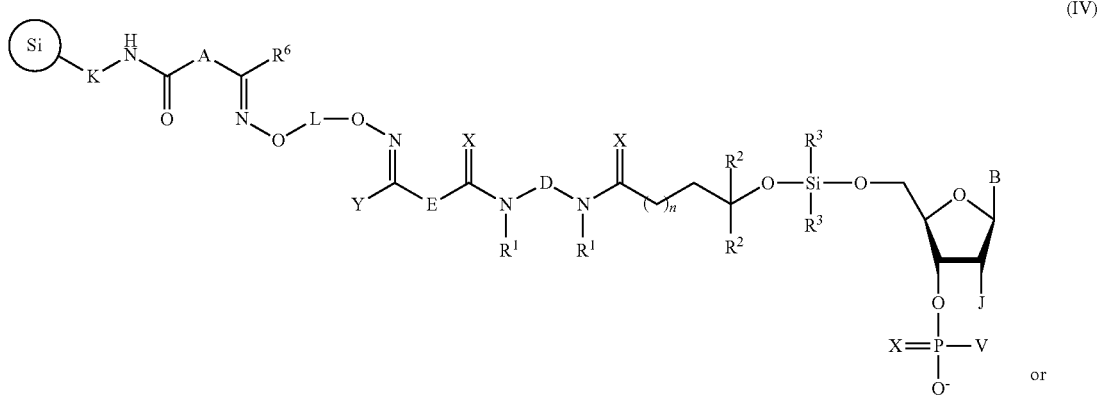

(IVa)

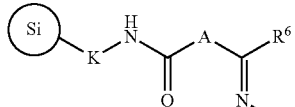 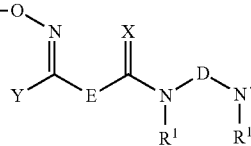

(vi) washing the linker-attached oligonucleotide of the formula (IV) or (IVa) with at least one solvent or a mixture of solvents to remove the oligonucleotide(s) or oligonucleotide analog(s) composed of "a" nucleotides;

(vii) treating the linker-attached oligonucleotide or oligonucleotide analog of formula (IV) or (IVa) with a desilylation agent; and (viii) isolating the purified oligonucleotide or oligonucleotide analog composed of "b" nucleotides from the product of step (vii);

wherein

B is an optionally protected nucleobase or an optionally protected nucleobase analog;

D and E are independently $C_2$-$C_{10}$ alkanediyl;

n is 1 to 4;

$R^1$ is $C_1$-$C_6$ linear or branched alkyl or $C_3$-$C_8$ cycloalkyl;

$R^2$ is hydrogen or linear or branched $C_1$-$C_6$ alkyl;

$R^3$ is linear or branched $C_3$-$C_6$ alkyl;

J is H or $OR^7$ wherein $R^7$ is a reversible or permanent hydroxyl protecting group;

X is O or S;

Y is H or $C_1$-$C_6$ linear alkyl;

W is a lone pair of electrons or an oxo function;

when W is a lone pair of electrons, Z is $NR^4R^5$ wherein $R^4$ and $R^5$ are individually $C_1$-$C_6$ alkyl, $C_6$-$C_{10}$ arylated $C_1$-$C_6$ alkyl, or $C_3$-$C_8$ cycloalkyl or $R^4$ and $R^5$ taken together with the nitrogen atom to which they are attached form a saturated 3-10 membered heterocyclic ring optionally including one or more additional heteroatoms selected from the group consisting of nitrogen, oxygen and sulfur, and Q is OT wherein T is a reversible or permanent hydroxyl protecting group; and when W is an oxo function, Z is H and Q is $O^-$.

Paragraph 2. The method of paragraph 1, wherein A is 1,5-pentanediyl.

Paragraph 3. The method of paragraph 1 or 2, wherein K is 1,3-propanediyl.

Paragraph 4. The method of any one of paragraphs 1-3, wherein L is 1,3-propanediyl.

Paragraph 5. The method of any one of paragraphs 1-4, wherein D is 1,2-ethanediyl.

Paragraph 6. The method of any one of paragraphs 1-5, wherein E is 1,5-pentanediyl.

Paragraph 7. The method of any one of paragraphs 1-6, wherein n is 1.

Paragraph 8. The method of any one of paragraphs 1-7, wherein $R^2$ is methyl.

Paragraph 9. The method of any one of paragraphs 1-8, wherein $R^3$ is 2-propyl.

Paragraph 10. The method of any one of paragraphs 1-9, wherein $R^6$ is methyl.

Paragraph 11. The method of any one of paragraphs 1-10, wherein J is H.

Paragraph 12. The method of any one of paragraphs 1-10, wherein J is $OR^7$.

Paragraph 13. The method of paragraph 12, wherein J is an acetal, ketal, thioacetal, or acetalester.

Paragraph 14. The method of paragraph 12, wherein $R^7$ has a formula

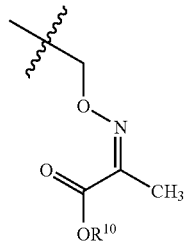

wherein $R^{10}$ is H, alkyl, cycloalkyl, or $OR^{10}$ is $O^-M^+$.

Paragraph 15. The method of paragraph 13, wherein $R^{10}$ is $C_{1-6}$alkyl.

Paragraph 16. The method of paragraph 14, wherein $R^{10}$ is ethyl.

Paragraph 17. The method of any one of paragraphs 1-16, wherein Y is methyl.

Paragraph 18. The method of any one of paragraphs 1-17, wherein the desilylation agent comprises fluoride ion.

Paragraph 19. The method of any one of paragraphs 1-18, wherein the protected nucleoside or nucleoside analog is of formula (I).

Paragraph 20. The method of any one of paragraphs 1-19, wherein W is a lone pair of electrons.

Paragraph 21. The method of any one of paragraphs 1-20, wherein Z is $NR^4R^5$ wherein $R^4$ and $R^5$ are individually $C_1$-$C_6$ alkyl, $C_6$-$C_{10}$ arylated $C_1$-$C_6$ alkyl, and $C_3$-$C_8$ cycloalkyl containing 1 to 10 carbon atoms or $R^4$ and $R^5$ taken together with the nitrogen atom to which they are attached form a saturated 3-10 membered heterocyclic ring optionally including one or more additional heteroatoms selected from the group consisting of nitrogen, oxygen and sulfur.

Paragraph 22. The method of any one of paragraphs 1-21, wherein Q is OT wherein T is a reversible or permanent hydroxyl protecting group.

Paragraph 23. The method of any one of paragraphs 1-22, wherein the optionally protected first oligonucleotide or oligonucleotide analog is synthesized by a solid-phase protocol.

Paragraph 24. A compound of the formula:

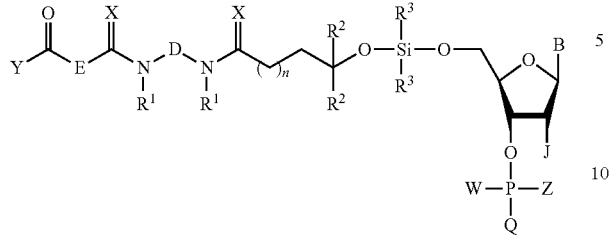

wherein B is an optionally protected nucleobase or nucleobase analog,

D and E are independently $C_2$-$C_{10}$ alkanediyl, n is 1 to 4, $R^1$ is $C_1$-$C_6$ linear or branched alkyl or $C_3$-$C_8$ cycloalkyl, $R^2$ is hydrogen or $C_1$-$C_6$ linear or branched alkyl or $C_3$-$C_8$ cycloalkyl, $R^3$ is linear or branched $C_3$-$C_6$ alkyl, J is H or $OR^7$ wherein $R^7$ is a reversible or permanent hydroxyl protecting group, X is O or S, Y is H or linear $C_1$-$C_6$ alkyl, W is a lone pair of electrons, and Z is $NR^4R^5$ wherein $R^4$ and $R^5$ are individually $C_1$-$C_6$ alkyl, $C_6$-$C_{10}$ arylated $C_1$-$C_6$ alkyl, or $C_3$-$C_8$ cycloalkyl containing 1 to 10 carbon atoms or $R^4$ and $R^5$ taken together with the nitrogen atom to which they are attached form a saturated 3-10 membered heterocyclic ring optionally including one or more additional heteroatoms selected from the group consisting of nitrogen, oxygen and sulfur, and Q is OT wherein T is a reversible or permanent hydroxyl protecting group.

Paragraph 25. The compound of paragraph 24, wherein $R^1$ is methyl.

Paragraph 26. The compound of paragraph 24 or paragraph 25, wherein $R^2$ is methyl.

Paragraph 27. The compound of any one of paragraphs 24-26, wherein $R^3$ is 2-propyl.

Paragraph 28. The compound of any one of paragraphs 24-27, wherein D is 1,2-ethanediyl.

Paragraph 29. The compound of any one of paragraphs 24-28, wherein E is 1,5-pentanediyl.

Paragraph 30. The compound of any one of paragraphs 24-29, wherein n is 1.

Paragraph 31. The compound of any one of paragraphs 24-30, wherein J is H.

Paragraph 32. The compound of any one of paragraphs 24-31 wherein J is $OR^7$ and $R^7$ is a reversible or permanent hydroxyl protecting group stable to the alkaline conditions utilized in nucleobase and optional phosphate/thiophosphate deprotection.

Paragraph 33. The compound of any one of paragraphs 24-32, wherein J is an acetal, ketal, thioacetal, or acetalester.

Paragraph 34. The compound of any one of paragraphs 24-33, wherein J is $OR^7$, and $R^7$ has a formula

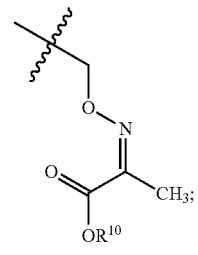

wherein $R^{10}$ is H, alkyl, cycloalkyl, or $OR^{10}$ is $O^+M^+$.

Paragraph 35. The method of paragraph 34, wherein $R^{10}$ is $C_{1-6}$alkyl.

Paragraph 36. The method of paragraph 35, wherein $R^{10}$ is ethyl.

Paragraph 37. The compound of any one of paragraphs 24-36, wherein Z is diisopropylamino.

Paragraph 38. A method of preparing the compound of any one of paragraphs 24-37 wherein W is a lone pair of electrons, Z is $NR^4R^5$, and Q is OT wherein T is 2-cyanoethyl, comprising:

(i) providing a compound of the formula (1):

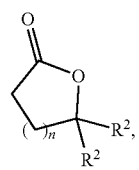

(1)

(ii) reacting the compound of step (i) with a compound of the formula:

$R^1HN\text{-}D\text{-}NHR^1$ to provide a compound of the formula (2):

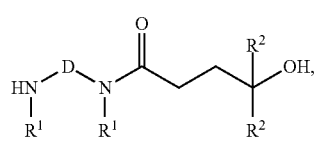

(2)

(iii) reacting the compound of formula (2) with a compound of the formula:

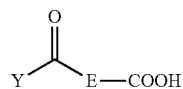

to provide a compound of formula (3):

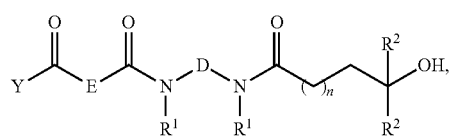

(3)

(iv) reacting the compound of formula (3) with a compound of the formula: $(R^3)_2SiX_2$, wherein X is a leaving group, to provide a compound of formula (4):

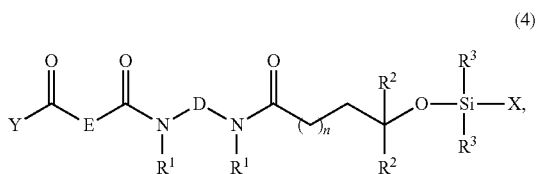
(4)

(v) reacting the compound of formula (4) with a nucleobase protected 2'-deoxyribonucleoside or nucleobase-protected 2'-O-protected ribonucleoside or a nucleobase-protected and carbohydrate modified analog thereof to provide a compound of the formula (5):

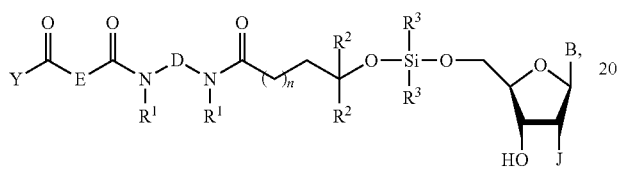
(5)

and (vi) reacting the compound of formula (5) with $[(R^4R^5)]_2$NPOCH$_2$CH$_2$CN or $R^4R^5$NP(X')OCH$_2$CH$_2$CN wherein X' is a monovalent leaving group to provide a compound of the formula (6):

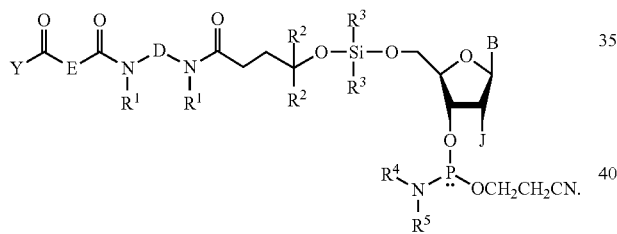
(6)

Paragraph 39. A capture support of the formula (9):

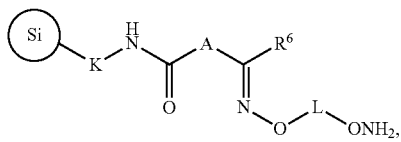
(9)

wherein A, K, and L are independently $C_2$-$C_{10}$ alkanediyl and $R^6$ is H or $C_1$-$C_6$ linear or branched alkyl or $C_1$-$C_6$ cycloalkyl, and wherein

is silica.

Paragraph 40. The capture support of paragraph 39, wherein $R^6$ is methyl.

Paragraph 41. The capture support of paragraph 39 or 40, wherein A is 1,5-pentanediyl.

Paragraph 42. The capture support of any one of paragraphs 39-41, wherein K and L are individually 1,3-propanediyl.

Paragraph 43. A method of preparing the capture support of any one of paragraphs 39-42, comprising:

(i) providing a functionalized silica gel of the formula (10):

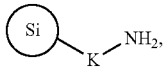
(10)

(ii) reacting the functionalized silica gel of the formula (10) with a compound of the formula:

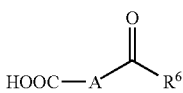

to provide a compound of formula (11):

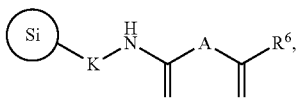
(11)

and (iii) reacting the compound of formula (11) with a compound of the formula:

H$_2$NO-L-ONH$_2$ to provide the capture support of any one of paragraphs 39-42.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of purifying an oligonucleotide or an oligonucleotide analog composed of "b" nucleotides from a mixture comprising the oligonucleotide or oligonucleotide analog and at least one oligonucleotide or oligonucleotide analog composed of "a" nucleotides, wherein b≠a, the method comprising:

(i) providing a protected nucleoside or nucleoside analog of formula (I) or (Ia) functionalized with an activatable phosphorus-containing entity

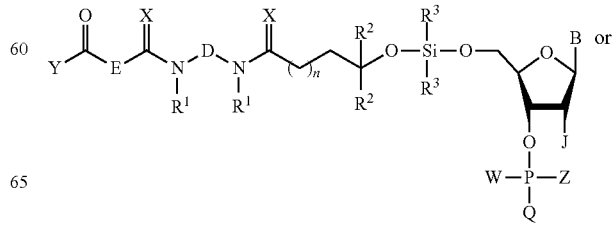

(Ia)

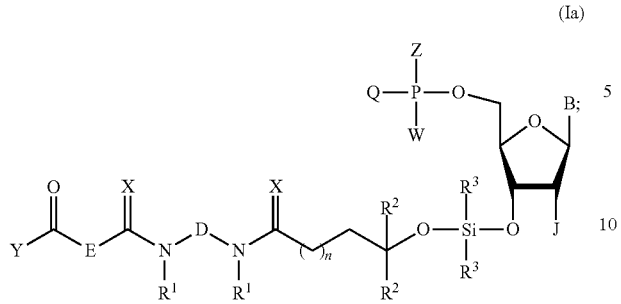

(ii) providing a mixture comprising an optionally protected first oligonucleotide or oligonucleotide analog V' composed of b-1 nucleotides or nucleotide analogs and having a free 5'-terminal OH group, wherein the first oligonucleotide V' comprises phosphate or phosphorothioate triester linkages, or a combination thereof, and wherein the first oligonucleotide V' is linked at its 3'-terminus to a solid support, wherein at least one oligonucleotide or oligonucleotide analog composed of "a" nucleotides is also linked to the solid support;

(iii) coupling the first oligonucleotide V' with the protected nucleoside or nucleoside analog of formula (I) or (Ia), to provide a second oligonucleotide of the formula (II) or (IIa)

(II)

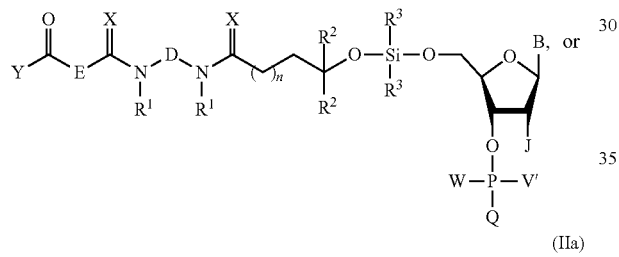

(IIa)

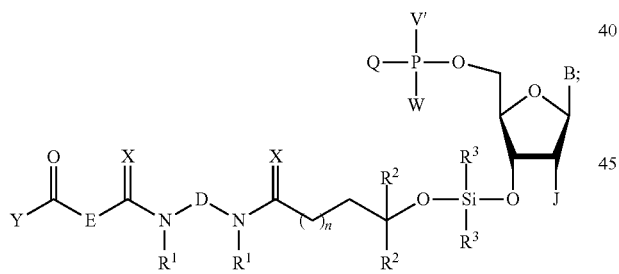

(iv) oxidizing or sulfurizing, optionally deprotecting, and cleaving the second oligonucleotide or oligonucleotide analog of the formula (II) or (IIa) from the solid support to form a mixture comprising a third oligonucleotide of the formula (III) or (IIIa)

(III)

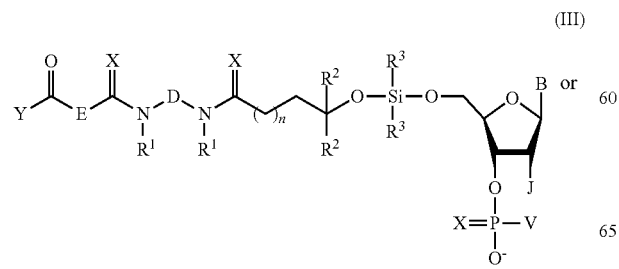

(IIIa)

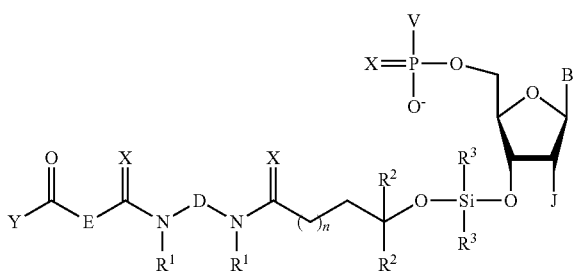

wherein V is the moiety resulting after optional deprotection of the second oligonucleotide or oligonucleotide analog and wherein V is not linked to the solid support;

(v) reacting the mixture comprising the third oligonucleotide or oligonucleotide analog of the formula (III) or (IIIa) with a silica-attached linker compound of the formula:

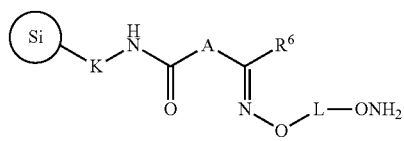

wherein A, K, and L are independently $C_2$-$C_{10}$ alkanediyl and $R^6$ is H or $C_1$-$C_6$ linear or branched alkyl or $C_3$-$C_8$ cycloalkyl, and wherein

is silica, to form a linker-attached oligonucleotide or oligonucleotide analog of the formula (IV) or (IVa)

(IV)

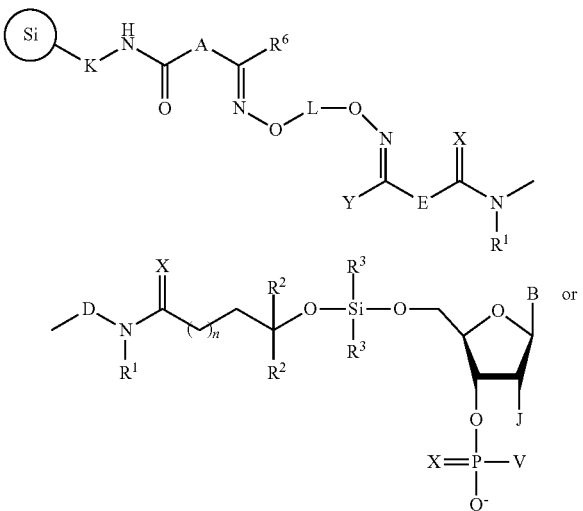

-continued (IVa)

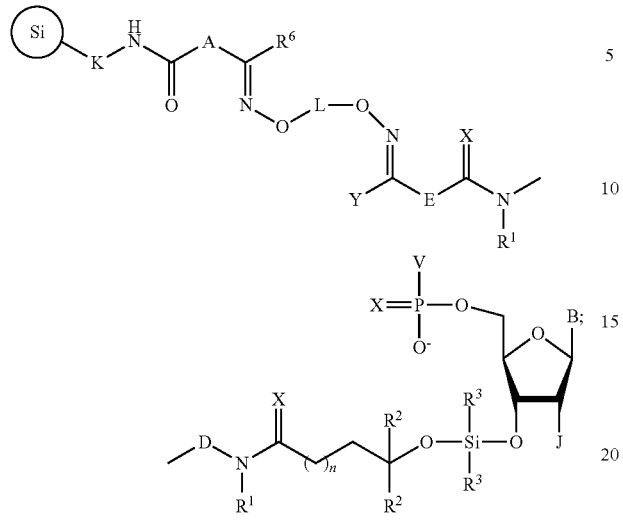

(vi) washing the linker-attached oligonucleotide of the formula (IV) or (IVa) with at least one solvent or a mixture of solvents to remove the oligonucleotide(s) or oligonucleotide analog(s) composed of "a" nucleotides;
(vii) treating the linker-attached oligonucleotide or oligonucleotide analog of formula (IV) or (IVa) with a desilylation agent; and
(viii) isolating the purified oligonucleotide or oligonucleotide analog composed of "b" nucleotides from the product of step (vii);
wherein
B is an optionally protected nucleobase or an optionally protected nucleobase analog;
D and E are independently $C_2$-$C_{10}$ alkanediyl;
n is 1 to 4;
$R^1$ is $C_1$-$C_6$ linear or branched alkyl or $C_3$-$C_8$ cycloalkyl;
$R^2$ is hydrogen or linear or branched $C_1$-$C_6$ alkyl;
$R^3$ is linear or branched $C_3$-$C_6$ alkyl;
J is H or $OR^7$ wherein $R^7$ is a reversible or permanent hydroxyl protecting group;
X is O or S;
Y is H or $C_1$-$C_6$ linear alkyl;
W is a lone pair of electrons or an oxo (=O) function;
when W is a lone pair of electrons, Z is $NR^4R^5$ wherein $R^4$ and $R^5$ are individually $C_1$-$C_6$ alkyl, $C_6$-$C_{10}$ arylated $C_1$-$C_6$ alkyl, or $C_3$-$C_8$ cycloalkyl or $R^4$ and $R^5$ taken together with the nitrogen atom to which they are attached form a saturated 3-10 membered heterocyclic ring optionally including one or more additional heteroatoms selected from the group consisting of nitrogen, oxygen and sulfur, and Q is OT wherein T is a reversible or permanent hydroxyl protecting group; and
when W is an oxo function, Z is H and Q is O⁻.
2. The method of claim 1, wherein:
A is 1,5-pentanediyl;
K is 1,3-propanediyl;
L is 1,3-propanediyl;
D is 1,2-ethanediyl;
E is 1,5-pentanediyl;
$R^2$ is methyl;
$R^3$ is 2-propyl;
$R^6$ is methyl;
Y is methyl;
n is 1; or
a combination thereof.
3. The method of claim 1, wherein A is 1,5-pentanediyl, K is 1,3-propanediyl, L is 1,3-propanediyl, D is 1,2-ethanediyl, E is 1,5-pentanediyl, n is 1, $R^2$ is methyl, $R^3$ is 2-propyl, $R^6$ is methyl, and Y is methyl.
4. The method of claim 1, wherein J is H.
5. The method of claim 1, wherein J is $OR^7$.
6. The method of claim 5, wherein J is an acetal, ketal, thioacetal, or acetalester.
7. The method of claim 6, wherein $R^7$ has a formula

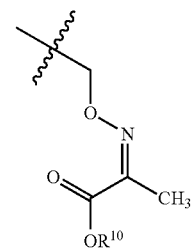

wherein $R^{10}$ is H, alkyl, cycloalkyl, or $OR^{10}$ is O⁻M⁺.
8. The method of claim 7, wherein $R^{10}$ is $C_{1-6}$alkyl.
9. The method of claim 7, wherein $R^{10}$ is ethyl.
10. The method of claim 1, wherein the desilylation agent comprises fluoride ion.
11. The method of claim 1, wherein the protected nucleoside or nucleoside analog is of formula (I).
12. The method of claim 11, wherein W is a lone pair of electrons.
13. The method of claim 12, wherein Z is $NR^4R^5$ wherein $R^4$ and $R^5$ are individually $C_1$-$C_6$ alkyl, $C_6$-$C_{10}$ arylated $C_1$-$C_6$ alkyl, and $C_3$-$C_8$ cycloalkyl containing 1 to 10 carbon atoms or $R^4$ and $R^5$ taken together with the nitrogen atom to which they are attached form a saturated 3-10 membered heterocyclic ring optionally including one or more additional heteroatoms selected from the group consisting of nitrogen, oxygen and sulfur.
14. The method of claim 13, wherein Q is OT wherein T is a reversible or permanent hydroxyl protecting group.
15. The method of claim 1, wherein the optionally protected first oligonucleotide or oligonucleotide analog is synthesized by a solid-phase protocol.
16. A compound of the formula:

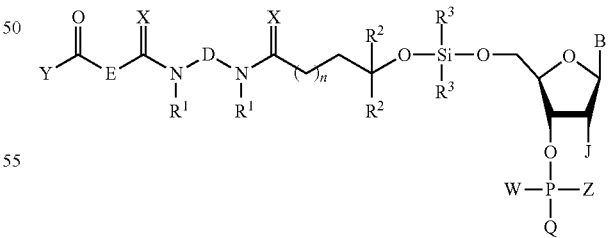

wherein B is an optionally protected nucleobase or nucleobase analog,
D and E are independently $C_2$-$C_{10}$ alkanediyl,
n is 1 to 4,
$R^1$ is $C_1$-$C_6$ linear or branched alkyl or $C_3$-$C_8$ cycloalkyl,
$R^2$ is hydrogen or $C_1$-$C_6$ linear or branched alkyl or $C_3$-$C_8$ cycloalkyl,
$R^3$ is linear or branched $C_3$-$C_6$ alkyl, J is H or OR[7] wherein R[7] is a reversible or permanent hydroxyl protecting group,
X is O or S,
Y is H or linear $C_1$-$C_6$ alkyl,
W is a lone pair of electrons, and
Z is $NR^4R^5$ wherein $R^4$ and $R^5$ are individually $C_1$-$C_6$ alkyl, $C_6$-$C_{10}$ arylated $C_1$-$C_6$ alkyl, or $C_3$-$C_8$ cycloalkyl containing 1 to 10 carbon atoms or $R^4$ and $R^5$ taken together with the nitrogen atom to which they are attached form a saturated 3-10 membered heterocyclic ring optionally including one or more additional heteroatoms selected from the group consisting of nitrogen, oxygen and sulfur, and Q is OT wherein T is a reversible or permanent hydroxyl protecting group.

17. The compound of claim 16, wherein:
$R^1$ is methyl;
$R^2$ is methyl;
$R^3$ is 2-propyl; or
a combination thereof.

18. The compound of claim 16, wherein:
D is 1,2-ethanediyl;
E is 1,5-pentanediyl; or
a combination thereof.

19. The compound of claim 16, wherein n is 1.

20. The compound of claim 16, wherein Z is diisopropylamino.

21. The compound of claim 16, wherein $R^1$ is methyl, $R^2$ is methyl, $R^3$ is 2-propyl, D is 1,2-ethanediyl, E is 1,5-pentanediyl, n is 1, and Z is diisopropylamino.

22. The compound of claim 16, wherein J is H.

23. The compound of claim 16 wherein J is OR[7] and R[7] is a reversible or permanent hydroxyl protecting group stable to the alkaline conditions utilized in nucleobase and optional phosphate/thiophosphate deprotection.

24. The compound of claim 23, wherein J is an acetal, ketal, thioacetal, or acetalester.

25. The compound of claim 23, wherein J is OR[7], and R[7] has a formula

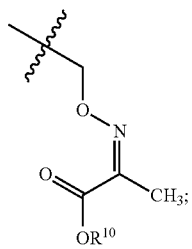

wherein $R^{10}$ is H, alkyl, cycloalkyl, or $OR^{10}$ is $O^-M^+$.

26. The method of claim 25, wherein $R^{10}$ is $C_{1-6}$alkyl.

27. The method of claim 26, wherein $R^{10}$ is ethyl.

28. A method of preparing the compound of claim 1 wherein W is a lone pair of electrons, Z is $NR^4R^5$, and Q is OT wherein T is 2-cyanoethyl, comprising:
(i) providing a compound of the formula (1):

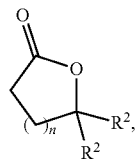

(ii) reacting the compound of step (i) with a compound of the formula:

to provide a compound of the formula (2):

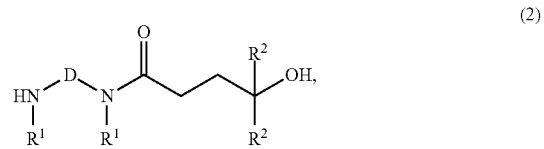

(iii) reacting the compound of formula (2) with a compound of the formula:

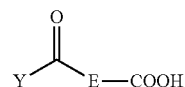

to provide a compound of formula (3):

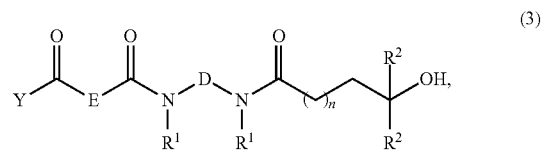

(iv) reacting the compound of formula (3) with a compound of the formula: $(R^3)_2SiX_2$, wherein X is a leaving group, to provide a compound of formula (4):

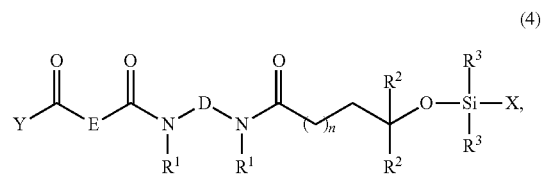

(v) reacting the compound of formula (4) with a nucleobase protected 2'-deoxyribonucleoside or nucleobase-protected 2'-O-protected ribonucleoside or a nucleobase-protected and carbohydrate modified analog thereof to provide a compound of the formula (5):

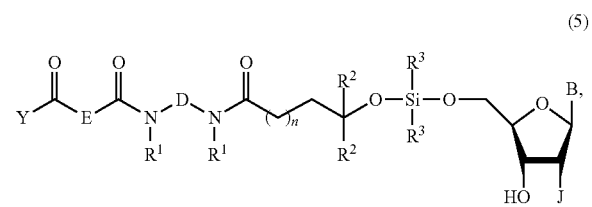

and
(vi) reacting the compound of formula (5) with [($R^4R^5$)]$_2$NPOCH$_2$CH$_2$CN or $R^4R^5$NP(X')OCH$_2$CH$_2$CN wherein X' is a monovalent leaving group to provide a compound of the formula (6):

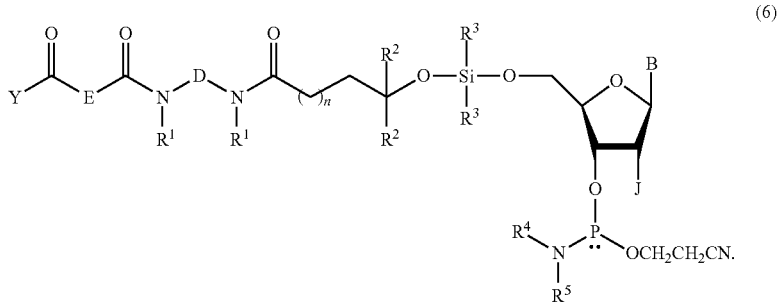

(6)

29. A capture support of the formula (9):

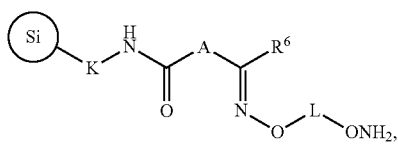

(9)

wherein A, K, and L are independently $C_2$-$C_{10}$ alkanediyl and $R^6$ is H or $C_1$-$C_6$ linear or branched alkyl or $C_1$-$C_6$ cycloalkyl, and wherein

is silica.

30. A method of preparing the capture support of claim 29, comprising:

(i) providing a functionalized silica gel of the formula (10):

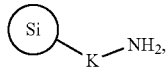

(10)

(ii) reacting the functionalized silica gel of the formula (10) with a compound of the formula:

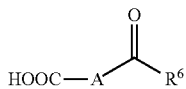

to provide a compound of formula (11):

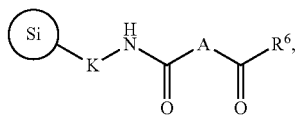

(11)

and (iii) reacting the compound of formula (11) with a compound of the formula:

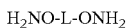

to provide the capture support of claim 29.

* * * * *